United States Patent [19]

Markley et al.

[11] Patent Number: 5,780,465
[45] Date of Patent: Jul. 14, 1998

[54] 4-SUBSTITUTED 5-POLYCYCLYLPYRIMIDINE HERBICIDES

[75] Inventors: Lowell D. Markley, Zionsville; Kim E. Arndt, Indianapolis; Patricia G. Ray, Carmel; Terry W. Balko, Greenfield; Erik N. K. Cressman, Indianapolis; David G. Ouse, Indianapolis; Johnny L. Jackson, Indianapolis; Jacob Secor, Zionsville, all of Ind.

[73] Assignee: Dow AgroSciences LLC, Indianapolis, Ind.

[21] Appl. No.: 833,065

[22] Filed: Apr. 3, 1997

[51] Int. Cl.$^6$ .................... A01N 43/54; C07D 239/04
[52] U.S. Cl. .................. 514/224.2; 514/247; 514/269; 544/242; 544/315; 544/333; 544/334; 544/2; 544/47
[58] Field of Search ............ 514/224.2, 247, 514/269; 544/242, 315, 333, 334, 2, 47

[56] References Cited

U.S. PATENT DOCUMENTS

| | | | |
|---|---|---|---|
| 3,818,009 | 6/1974 | Taylor et al. | |
| 4,518,600 | 5/1985 | Holmwood et al. | 514/256 |
| 4,769,378 | 9/1988 | Hirsch et al. | 514/267 |
| 4,877,496 | 10/1989 | Elbe et al. | 544/225 |
| 4,898,968 | 2/1990 | McDonald et al. | 560/124 |
| 5,073,187 | 12/1991 | Elliot | 544/335 |
| 5,484,787 | 1/1996 | Shaber et al. | 514/256 |

FOREIGN PATENT DOCUMENTS

| | | |
|---|---|---|
| 0 713 872 A1 | 8/1994 | European Pat. Off. |
| 2406799 | 2/1974 | Germany |
| 07033748 | 2/1995 | Japan |
| PCT/JP94/01847 | 5/1995 | WIPO |

OTHER PUBLICATIONS

Tsatsaronis et al., J. Org.Chem. 35(2), pp. 438–441, 1970.
Kreutzberger et al., Justus Liebigs Ann. Chem. (4) pp. 537–544, 1977.
Koyama et al., Yakugaku Zasshi, 93(11), pp. 1481–1483, 1973.

*Primary Examiner*—Jeffrey C. Mullis
*Attorney, Agent, or Firm*—D. Wendell Osborne

[57] ABSTRACT

4-Substituted 5-polycyclylpyrimidine compounds in which the 5-substituent is polycyclic and is attached to the pyrimidine moiety through an aliphatic carbon atom, such as 5-(2,2-dimethylindan-1-yl)-4-methylthiopyrimidine, were prepared and found to possess excellent herbicidal activity. The compounds are especially useful for the control of undesirable vegetation in paddy rice.

47 Claims, No Drawings

4-SUBSTITUTED 5-POLYCYCLYLPYRIMIDINE HERBICIDES

BACKGROUND OF THE INVENTION

The present invention relates to substituted pyrimidine compounds, to herbicidal compositions containing the compounds, and to the utility of the compounds for the control of unwanted vegetation.

The control of unwanted vegetation by means of chemical agents known as herbicides is an important aspect of modern agriculture and land management. While many chemicals that are useful for the control of unwanted vegetation are known, new compounds that are more effective generally, are more effective for specific plant species, are less damaging to desirable vegetation, are safer to man or the environment, are less expensive to use, are chemically diverse, or have other advantageous attributes are desirable.

Certain pyrimidine compounds that are substituted in the 5-position with a substituent that is primarily hydrocarbon in nature are known. For example, pyrimidine compounds possessing certain bis(hydrocarbyl)hydroxymethyl substituents in the 5-position as the only substituent are disclosed in U.S. Pat. No. 3,818,009. Certain compounds of this type are known to possess fungicidal and plant growth regulator activity and a few, including ancymidol, fenarimol, flurprimidol, and nuarimol, have achieved commercial status. Certain 4,5-disubstituted pyrimidine compounds wherein the 4-position substituent is a halodifluoromethyl group and the 5-position substituent is inter alia a benzyl moiety were disclosed in PCT Application WO 95/12582. Such compounds wherein the 4-position substituent is more broadly described as $C_1-C_6$ alkyl or haloalkyl or substituted phenyl were disclosed in PCT Application WO 95/04725.

SUMMARY OF THE INVENTION

It has now been found that many novel 4-substituted 5-polycyclylpyrimidine compounds in which the 5-substituent is polycyclic and is attached to the pyrimidine moiety through an aliphatic carbon atom possess excellent herbicidal activity and can be employed to control undesirable vegetation.

The invention includes 5-polycyclylpyrimidine compounds of Formula I:

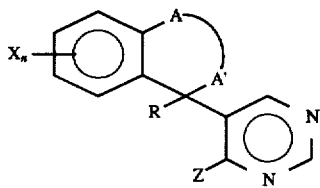

wherein
the moiety

represents a 2 or 3 unit chain having a maximum of 3 chain atoms, the units of which are selected from —CR'$_2$— (which may comprise up to 3 units) and —CR'=CR'—, —O—, —S—, —NH—, —N($C_1-C_4$ alkyl)-, —C(O)—, or —S(O)$_2$— (which may comprise up to 1 unit) or represents a chain of the formula:

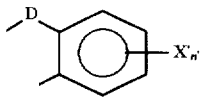

wherein D represents —O—CR'$_2$—O— or —CR'$_2$—CR'$_2$—;

each R' independently represents H, $C_1-C_3$ alkyl or phenyl or two R' located on the same carbon atom or on adjacent carbons together represent —(CH$_2$)(2-5)-;

R represents H, OH, F, Cl, Br, $C_1-C_3$ alkyl, or $C_1-C_3$ alkoxy;

Z represents L($C_1-C_4$ alkyl) optionally substituted with one or two substituents selected from Cl, Br, CN, OH, O($C_1-C_3$ alkyl), SO$_m$($C_1-C_3$ alkyl), N($C_1-C_3$ alkyl)$_2$, CO$_2$($C_1-C_4$ alkyl), CO$_2$H, or with up to the maximum possible number of F, or with a phenyl or pyridinyl moiety each optionally substituted with up to 3 compatible substituents selected from F, Cl, Br, NO$_2$, CF$_3$, CH$_3$, OCH$_3$, SO$_m$CH$_3$, CN, and CO$_2$($C_1-C_4$ alkyl); L($C_3-C_4$ alkenyl) optionally substituted with one or two substituents selected from Cl, Br, CN, O($C_1-C_3$ alkyl), SO$_m$($C_1-C_3$ alkyl), CO$_2$($C_1-C_4$ alkyl), CO$_2$H, and phenyl or with up to the maximum possible number of F; L($C_3-C_4$ alkynyl) optionally mono-substituted with CO$_2$($C_1-C_4$ alkyl) or C$_6$H$_5$; L(phenyl) optionally substituted with up to 3 compatible substituents selected from F, Cl, Br, NO$_2$, CF$_3$, CH$_3$, OCH$_3$, SO$_m$CH$_3$, CN, and CO$_2$($C_1-C_4$ alkyl); CN, CO$_2$($C_1-C_4$ alkyl), CONH$_2$, CONH($C_1-C_4$ alkyl), CON($C_1-C_4$ alkyl)$_2$, CO$_2$H, NH$_2$, NHSO$_2$($C_1-C_4$ alkyl), N($C_1-C_4$ alkyl)-SO$_2$($C_1-C_4$ alkyl), SH, F, Cl, or Br;

L represents -, O, SO$_m$, SO$_2$NH, SO$_2$N($C_1-C_4$ alkyl), NH, or N($C_1-C_4$ alkyl);

X and X' each independently represents F, Cl, Br, CN, CO$_2$($C_1-C_4$ alkyl), NO$_2$, NH($C_1-C_3$ alkyl), N($C_1-C_3$ alkyl)$_2$, NH$_2$, NHCO($C_1-C_3$ alkyl), NHSO$_2$($C_1-C_3$ alkyl), or N(SO$_2$($C_1-C_3$ alkyl))$_2$; or represents $C_1-C_3$ alkyl, O($C_1-C_3$ alkyl), SO$_m$($C_1-C_3$ alkyl), or CO($C_1-C_3$ alkyl) each alkyl of which is optionally singly to completely fluorinated; or two adjacent X or X' together represent —OCH$_2$O— optionally substituted with one or two fluorine atoms;

n and n' each independently represents 0, 1, 2, or 3; and each m independently represents 0, 1, or 2; or an N-oxide derivative thereof.

The compounds of Formula I are herbicides that can be employed to control undesirable vegetation. They are especially useful for the control of common weeds in paddy rice. The compounds are typically employed to control undesirable vegetation in the form of a herbicidal composition containing an effective amount of a compound of Formula I in admixture with one or more agriculturally acceptable adjuvants or carriers.

DETAILED DESCRIPTION OF THE INVENTION

The 4-substituted 5-polycyclylpyrimidine compounds of the present invention, which include compounds of Formula I:

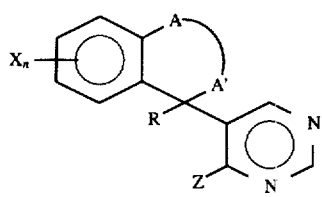

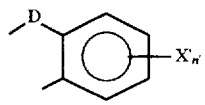

and their N-oxide derivatives can be described as pyrimidine compounds substituted in the 5-position with a polycyclic substituent, which substituent may contain oxygen, sulfur, or nitrogen heteroatoms and which may be substituted, and in the 4-position with one of a selected group of substituents.

The 5-position polycyclic substituents of the compounds of Formula I, which have the formula:

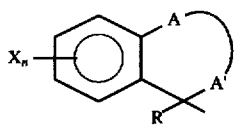

are all polycyclic moieties, one ring of which is generally aliphatic in nature and is attached directly to the pyrimidine ring of said compound through a tetrasubstituted carbon atom (a saturated aliphatic carbon atom) and one or two rings of which are benzenoid in nature and have a common side (fused ring orientation) with the directly attached, generally aliphatic ring. The polycyclic moiety may further have a second generally aliphatic ring which is attached to the required generally aliphatic ring at two adjacent carbon atoms (common side; fused ring orientation) or is attached to a single carbon atom (common carbon atom; spiro orientation). The directly attached, generally aliphatic ring is a 5 to 8 atom ring, some atoms of which may be oxygen, sulfur, or nitrogen atoms in specified circumstances. The sulfur heteroatom may be in an oxidized sulfoxide or sulfone form. The directly attached, generally aliphatic ring is partially unsaturated having at least the unsaturation of one benzene ring that is fused to it and may be further unsaturated due to the presence of a second fused benzene ring or of an aliphatic double bond. One carbon atom of this ring may also be in the keto form.

The 5-position polycyclic substituent moiety:

(—A–A'—) represents a fragment from one of the following subsets: a) a 2 or 3 atom chain composed of 2 or 3 units selected from —CR'$_2$—, —O—, —S—, —C(O)—, —S(O)$_2$—, and —CR'=CR'— provided that no more than one of the units is —O—, —S—, —C(O)—, —S(O)$_2$—, or —CR'=CR'—, or b) a fragment of the formula wherein D represents —O—CR'$_2$—O— or —CR'$_2$—CR'$_2$—. In the foregoing, each R' independently represents hydrogen, methyl, ethyl, 1-methylethyl, propyl, or phenyl or two R' located on the same carbon atom or on adjacent carbon atoms together represent a di-, tri-, tetra-, or pentamethylene fragment. Compounds wherein R' represents hydrogen or methyl are often preferred. Compounds wherein the two R' substituents on the same carbon atom are both methyl or are both hydrogen are more preferred. Representative polycyclic substituents include substituents based on the following ring systems wherein the dotted line bond represents the point of attachment:

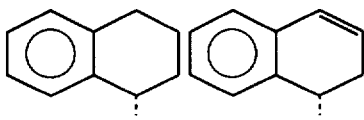

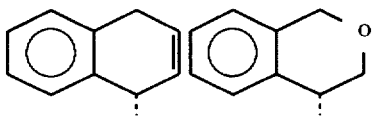

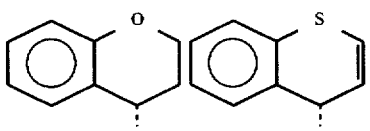

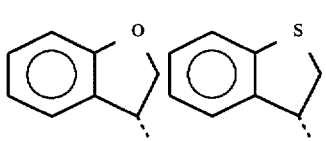

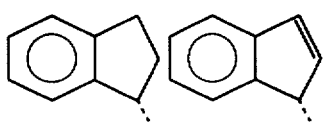

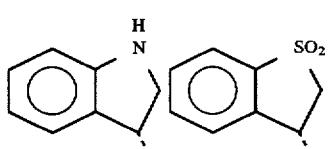

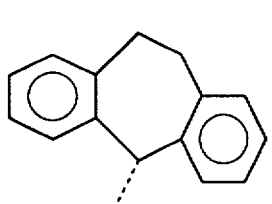

-continued

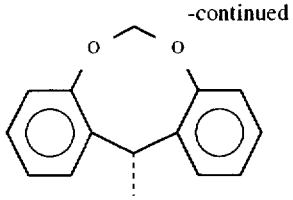

Polycyclic 5-position substituents wherein the moiety:

(—A–A'—) represents a two or three unit chain are sometimes preferred. Such compounds wherein the unit attached to the carbon atom that is also attached to the pyrimidinyl moiety (the A' terminus of —A–A'—) is a —CR'$_2$— unit are often more preferred, and of those, compounds wherein each R' represents methyl are typically most preferred. Compounds wherein —A–A'— represents —CH$_2$C(CH$_3$)$_2$—, —CH$_2$CH$_2$C(CH$_3$)$_2$—, and —OCH$_2$C(CH$_3$)$_2$— are often of special interest. Compounds wherein —A–A'— represents:

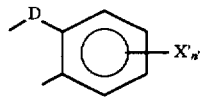

and D represents —OCR'$_2$O— are sometimes preferred, and of those, compounds wherein D represents —OCH$_2$O— are often more preferred.

R in the polycyclic substituent of Formula I, which is the substituent on the carbon atom at the point of attachment of the substituent to the pyrimidine ring, represents one of hydrogen, hydroxyl, fluorine, chlorine, bromine, methyl, ethyl, propyl, methoxy, ethoxy, and propoxy. Compounds wherein R represents hydrogen, hydroxy, methoxy, or ethoxy, are generally preferred. Compounds wherein R represents hydrogen are usually more preferred.

Each of the benzene rings of the polycyclic 5-position substituents of Formula I may also be mono, di, or trisubstituted. X and X', for example, may each independently represent fluoro, chloro, bromo, cyano, nitro, amino, (C$_1$–C$_3$ alkyl)amino, di(C$_1$–C$_3$ alkyl)amino, ((C$_1$–C$_3$ alkyl)carbonyl)amino, ((C$_1$–C$_3$ alkyl)sulfonyl)amino, di((C$_1$–C$_3$ alkyl)sulfonyl)amino, (C$_1$–C$_4$ alkoxy)carbonyl, or C$_1$–C$_3$ alkyl, C$_1$–C$_3$ alkoxy, C$_1$–C$_3$ alkylthio, C$_1$–C$_3$ alkylsulfinyl, C$_1$–C$_3$ alkylsulfonyl, or (C$_1$–C$_3$ alkyl)carbonyl, each alkyl of which may be optionally singly to completely substituted with fluorine. Two adjacent X or X' together may also represent —OCH$_2$O— which is optionally mono or disubstituted with fluorine. Compounds in which each of the benzene rings independently is either unsubstituted or is substituted with one or two substituents selected from fluoro, chloro, and methyl are often preferred.

The pyrimidine ring of the compounds of Formula I is substituted in the 4-position (Z) with one of a variety of substituents. Typically Z represents an alkyl, alkoxy, alkylthio, alkylsulfinyl, alkylsulfonyl, monoalkylamino, dialkylamino, or N-alkylaminosulfonyl moiety wherein each alkyl group contains 1 to 4 carbon atoms and is optionally substituted with one or two substituents selected from chloro, bromo, cyano, hydroxy, (C$_1$–C$_4$ alkoxy)carbonyl, hydroxycarbonyl, or a 1 to 3 carbon alkoxy, alkylthio, alkylsulfinyl, alkylsulfonyl, or dialkylamino group; or with up to the maximum possible number of fluoro substituents (C$_n$F$_{2n+1}$); or with a phenyl or pyridinyl moiety each optionally substituted with up to 3 compatible substituents selected from F, Cl, Br, NO$_2$, CF$_3$, CH$_3$, OCH$_3$, SO$_m$CH$_3$, CN, and CO$_2$(C$_1$–C$_4$ alkyl). Z further represents an alkenyl, alkenyloxy, alkenylthio, alkenylsulfinyl, alkenylsulfonyl, alkenylamino, or N-alkenylaminosulfonyl moiety wherein each alkenyl group contains three or four carbon atoms and is optionally substituted with one or two substituents selected from chloro, bromo, cyano, lower alkoxycarbonyl, hydroxycarbonyl, aminocarbonyl, alkylaminocarbonyl, phenyl, or a 1 to 3 carbon alkoxy, alkylthio, alkylsulfinyl, or alkylsulfonyl group; or with up to the maximum possible number of fluoro substituents (C$_n$F$_{2n-1}$) or represents an alkynyl, alkynoxy, alkynylthio, alkynylsulfinyl, alkynylsulfonyl alkynylamino, or N-alkynylaminosulfonyl moiety wherein each alkynyl group contains three or four carbon atoms and is optionally substituted with a lower alkoxycarbonyl, hydroxycarbonyl, or phenyl group. Z additionally represents a phenyl, phenoxy, phenylthio, phenylsulfinyl, phenylsulfonyl, phenylamino, or N-phenylaminosulfonyl group each optionally substituted with up to 3 compatible substituents selected from F, Cl, Br, NO$_2$, CF$_3$, CH$_3$, OCH$_3$, SO$_m$CH$_3$, CN, and CO$_2$(C$_1$–C$_4$ alkyl). Z still further represents a cyano, amino, (C$_1$–C$_4$ alkyl)sulfonylamino, (C$_1$–C$_4$ alkyl)sulfonyl(C$_1$–C$_4$ alkyl) amino, lower alkoxycarbonyl, hydroxycarbonyl, thiol, fluoro, chloro, or bromo group. Compounds wherein Z is a substituent described hereinabove that has an oxygen, sulfur, or nitrogen atom at the point of attachment to the pyrimidine ring are often preferred. Those having a sulfur atom at the point of attachement are typically more preferred. Compounds wherein Z represents methoxy, methylthio, ethylthio, monofluoromethylthio, difluoromethylthio, benzylthio, or allylthio are typically more preferred and those wherein Z represents methylthio or monofluoromethylthio are typically most preferred.

The N-oxide derivatives of the compounds of Formula I are those in which one of the nitrogen atoms of the pyrimidine ring is oxidized to an N-oxide. While it is not certain which of the two pyrimidine nitrogen atoms is in the oxidized form in these derivatives, nuclear magnetic resonance data suggests that the oxygen is on the 3-position nitrogen atom. This assignment is further supported by the fact that treatment of the N-oxide of 5-(2,2-dimethylindane-1-yl)-4-methylthiopyrimidine with phosphoryl chloride produces 2-chloro-5-(2,2-dimethylindane-1-yl)-4-methylthiopyrimidine. Compounds that are in the reduced form (are not oxidized in this manner) are generally preferred.

Table 1 lists some typical compounds of the invention. Compounds of special interest include 5-(2,2-dimethyl-1-indan-1-yl)-4-methylthiopyrimidine, 5-(2,2-dimethylindan-1-yl)-4-monofluoromethylthiopyrimidine, 5-(2,2,6-trimethylindan-1-yl)-4-methylthiopyrimidine, 5-(2,2-dimethyltetralin-1-yl)-4-methylthiopyrimidine and 5-(2,2,7-trimethyltetralin-1-yl)-4-methylthiopyrimidine.

TABLE 1

4,5-DISUBSTITUTED PYRIMIDINE COMPOUNDS

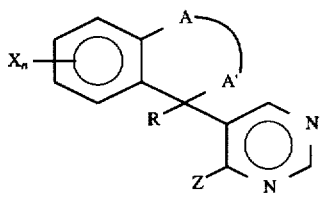

| Cpd No. | —A—A'— | $X_n$ | R | Z | Appearance | Melting Point °C. | Elem. Anal. calculated / found % C | % H | % N |
|---|---|---|---|---|---|---|---|---|---|
| 1 | —CH$_2$—C(CH$_3$)$_2$— | n = 0 | H | SCH$_3$ | white crystals | 92–95 | 71.1 / 71.0 | 6.71 / 6.68 | 10.4 / 10.6 |
| 2 | —CH$_2$—C(CH$_3$)$_2$— | n = 0 | OH | SCH$_3$ | white crystals | 189–190.5 | 67.1 / 67.0 | 6.33 / 6.53 | 9.78 / 9.97 |
| 3 | —CH$_2$—C(CH$_3$)$_2$— | n = 0 | H | OCH$_3$ | colorless oil |  | 75.6 / 75.8 | 7.13 / 7.04 | 11.0 / 11.1 |
| 4 | —CH$_2$—C(CH$_3$)$_2$— | n = 0 | OH | OCH$_3$ | colorless oil |  |  |  |  |
| 5 | —CH$_2$—C(CH$_3$)$_2$— | 5-Cl | H | SCH$_3$ | white crystals | 94–96 | 63.3 / 63.2 | 5.27 / 5.40 | 9.23 / 9.16 |
| 6 | —CH$_2$—C(CH$_3$)$_2$— | n = 0 | H | SC$_2$H$_5$ | colorless oil |  | 71.2 / 71.7 | 7.09 / 7.07 | 9.85 / 9.84 |
| 7 | —CH$_2$—C(CH$_3$)$_2$— | 5-F | H | SCH$_3$ | white solid | 110–112 | 66.6 / 66.5 | 5.94 / 6.20 | 9.71 / 9.76 |
| 8 | —CH$_2$—C(CH$_3$)$_2$— | 5-F | OH | SCH$_3$ | white solid | 160–162 | 63.1 / 62.8 | 5.58 / 5.60 | 9.20 / 9.70 |
| 9 | —CH$_2$—C(CH$_3$)$_2$— | 4-F | H | SCH$_3$ | white solid | 90–92 | 66.6 / 66.9 | 5.94 / 5.96 | 9.71 / 9.59 |
| 10 | —CH$_2$—C(CH$_3$)$_2$— | n = 0 | H | OC$_2$H$_5$ | clear oil |  | 76.1 / 75.9 | 7.51 / 7.46 | 9.85 / 10.1 |
| 11 | —CH$_2$—C(CH$_3$)$_2$— | 4-CH$_3$ | H | SCH$_3$ | white solid | 116 | 71.8 / 71.4 | 7.09 / 6.85 | 9.85 / 9.80 |
| 12 | —CH$_2$—C(CH$_3$)$_2$— | 4-CH$_3$ | OH | SCH$_3$ | white solid |  | 68.0 / 67.9 | 6.71 / 6.27 | 9.32 / 9.18 |
| 13 | —CH$_2$—C(CH$_3$)$_2$— | 6-CH$_3$ | H | SCH$_3$ | white solid |  | 71.8 / 71.9 | 7.09 / 6.93 | 9.85 / 9.92 |
| 14 | —CH$_2$—C(CH$_3$)$_2$— | 6-CH$_3$ | OH | SCH$_3$ | white solid | 179–180 | 68.0 / 67.5 | 6.71 / 7.25 | 9.32 / 9.36 |
| 15 | —CH$_2$—C(CH$_3$)$_2$— | 6-CH$_3$ | OCH$_3$ | SCH$_3$ | off-white solid |  | 68.7 / 67.8 | 7.00 / 7.04 | 8.90 / 8.88 |
| 16 | —CH$_2$—C(CH$_3$)$_2$— | 5-Br | H | SCH$_3$ | white solid | 100–102 | 55.2 / 55.2 | 4.64 / 4.87 | 8.04 / 8.02 |
| 17 | —CH$_2$—C(CH$_3$)$_2$— | 5-Br | OH | SCH$_3$ | white solid | 179–180 | 52.6 / 52.0 | 4.65 / 4.65 | 7.45 / 7.67 |
| 18 | —CH$_2$—C(CH$_3$)$_2$— | 7-CH$_3$ | H | SCH$_3$ | white solid | 126 | 71.8 / 71.7 | 7.09 / 6.96 | 9.85 / 9.85 |
| 19 | —CH$_2$—C(CH$_3$)$_2$— | 7-CH$_3$ | OH | SCH$_3$ | white powder |  |  |  |  |
| 20 | —CH$_2$—C(CH$_3$)$_2$— | 5-OCH$_3$ | H | SCH$_3$ | thick oil |  | 68.0 / 68.1 | 6.71 / 6.86 | 9.32 / 9.22 |
| 21 | —CH$_2$—C(CH$_3$)$_2$— | 6-CH$_3$ | H | OCH$_3$ | colorless solid |  | 76.1 / 76.0 | 7.51 / 7.39 | 10.4 / 10.5 |
| 22 | —CH$_2$—C(CH$_3$)$_2$— | 6-CH(CH$_3$)$_2$ | H | SCH$_3$ | yellow solid | 75–77 |  |  |  |
| 23 | —CH$_2$—C(CH$_3$)$_2$— | 6-CH(CH$_3$)$_2$ | OH | SCH$_3$ | white crystals | 157–159 | 69.4 / 69.4 | 7.31 / 8.52 | 8.52 / 8.54 |
| 24 | —CH$_2$—C(CH$_3$)$_2$— | 5-OCH$_3$, 6-OCH$_3$ | H | SCH$_3$ | off-white solid | 122–124 | 65.4 / 65.2 | 6.66 / 6.63 | 8.47 / 8.60 |
| 25 | —CH$_2$—C(CH$_3$)$_2$— | 4-NO$_2$, 5-OCH$_3$ | OH | SCH$_3$ | yellow solid | 216–218 |  |  |  |
| 26 | —CH$_2$—C(CH$_3$)$_2$— | 4-OCH$_3$ | H | SCH$_3$ | lt yellow solid | 99–100 |  |  |  |
| 27 | —CH$_2$—C(CH$_3$)$_2$— | 4-OCH$_3$, | OH | SCH$_3$ | white solid | 130–132 | 64.5 / 64.3 | 6.32 / 6.25 | 8.85 / 8.90 |
| 28 | —CH$_2$—C(CH$_3$)$_2$— | 6-C$_2$H$_5$ | H | SCH$_3$ | clear oil |  | 72.4 / 72.7 | 7.43 / 7.45 | 9.39 / 9.29 |
| 29 | —CH$_2$—C(CH$_3$)$_2$— | 6-C$_2$H$_5$ | OH | SCH$_3$ | white solid |  | 68.8 / 68.8 | 7.00 / 7.11 | 8.90 / 9.00 |
| 30 | —CH$_2$—C(CH$_3$)$_2$— | 5-CH$_3$, 7-CH$_3$ | H | SCH$_3$ | pale oil |  | 72.4 / 72.5 | 7.43 / 7.43 | 9.39 / 9.39 |

TABLE 1-continued

4,5-DISUBSTITUTED PYRIMIDINE COMPOUNDS

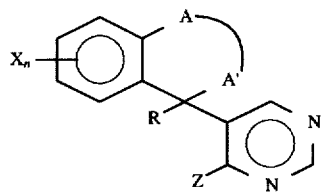

| Cpd No. | —A—A'— | $X_n$ | R | Z | Appearance | Melting Point °C. | Elem. Anal. calculated found %C | %H | %N |
|---|---|---|---|---|---|---|---|---|---|
| 31 | —CH$_2$—C(CH$_3$)$_2$— | 5-CH$_3$, 7-CH$_3$ | OH | SCH$_3$ | off-white solid | | | | |
| 32 | —CH$_2$—C(CH$_3$)$_2$— | 6-Br | H | SCH$_3$ | white solid | 118–123 | 55.0 55.1 | 4.87 5.00 | 8.25 8.02 |
| 33 | —CH$_2$—C(CH$_3$)$_2$— | 5-CH$_3$ | H | SCH$_3$ | colorless oil | | | | |
| 34 | —CH$_2$—C(CH$_3$)$_2$— | 5-CH$_3$ | OH | SCH$_3$ | white powder | | | | |
| 35 | —CH$_2$—C(CH$_3$)$_2$— | 4-F, 7-F | OH | SCH$_3$ | yellow solid | 181–183 | 60.0 59.4 | 4.96 5.08 | 8.69 8.57 |
| 36 | —CH$_2$—C(CH$_3$)$_2$— | n = 0 | OH | N(CH$_3$)$_2$ | yellow oil | | | | |
| 37 | —CH$_2$—C(CH$_3$)$_2$— | 6-CF$_3$ | OH | SCH$_3$ | yellow solid | 203–205 | 57.6 56.4 | 4.84 4.78 | 7.90 7.85 |
| 38 | —CH$_2$—C(CH$_3$)$_2$— | 5-CH$_3$, 6-OCH$_3$ | H | SCH$_3$ | thick oil | | 68.8 68.7 | 7.09 7.11 | 8.91 8.79 |
| 39 | —CH$_2$—C(CH$_3$)$_2$— | 5-CH$_3$, 6-OCH$_3$ | OH | SCH$_3$ | white solid | 157–158 | 65.4 65.5 | 6.66 6.69 | 8.47 8.61 |
| 40 | —CH$_2$—C(CH$_3$)$_2$— | 6-OC$_2$H$_5$ | H | SCH$_3$ | thick oil | | 68.8 68.7 | 7.09 7.31 | 8.91 8.77 |
| 41 | —CH$_2$—C(CH$_3$)$_2$— | n = 0 | H | N(CH$_3$)$_2$ | clear oil | | | | |
| 42 | —CH$_2$—C(CH$_3$)$_2$— | 6-OCH$_3$ | H | SCH$_3$ | oil | | 67.9 68.0 | 6.65 6.63 | 9.32 9.32 |
| 43 | —CH$_2$—C(CH$_3$)$_2$— | 6-OCH$_3$ | OH | SCH$_3$ | white solid | 140–142 | | | |
| 44 | —CH$_2$—C(CH$_3$)$_2$— | 6-F | H | SCH$_3$ | white solid | 105–115 | 66.6 66.3 | 5.94 5.94 | 9.72 9.61 |
| 45 | —CH$_2$—C(CH$_3$)$_2$— | 6-F | OH | SCH$_3$ | white solid | 172.5–174 | 63.1 63.0 | 5.63 5.63 | 9.21 9.17 |
| 46 | —CH$_2$—C(CH$_3$)$_2$— | 7-Cl | H | SCH$_3$ | tan solid | 122–123 | 63.0 62.8 | 5.62 5.76 | 9.19 9.29 |
| 47 | —CH$_2$—C(CH$_3$)$_2$— | 7-Cl | OH | SCH$_3$ | white solid | 171–172 | 59.9 59.6 | 5.34 5.52 | 8.73 8.79 |
| 48 | —CH$_2$—C(CH$_3$)$_2$— | 4-Cl | H | SCH$_3$ | off-white solid | 108–110 | 63.0 63.3 | 5.62 5.26 | 9.19 9.14 |
| 49 | —CH$_2$—C(CH$_3$)$_2$— | 4-Cl | OH | SCH$_3$ | white solid | 172–173 | 59.9 57.0 | 5.34 5.29 | 8.73 8.99 |
| 50 | —CH$_2$—C(CH$_3$)$_2$— | 6-Cl | H | SCH$_3$ | white solid | 134–136 | 63.0 62.7 | 5.62 5.55 | 9.19 9.17 |
| 51 | —CH$_2$—C(CH$_3$)$_2$— | 6-Cl | OH | SCH$_3$ | white solid | 151–153 | 59.9 59.6 | 5.34 5.37 | 8.73 8.80 |
| 52 | —CH$_2$—C(CH$_3$)$_2$— | 4-CH$_3$, 6-CH$_3$ | H | SCH$_3$ | white solid | 99–100 | 72.4 72.4 | 7.43 7.42 | 9.39 9.37 |
| 53 | —CH$_2$—C(CH$_3$)$_2$— | 4-CH$_3$, 6-CH$_3$ | OH | SCH$_3$ | white solid | 171–172 | 68.8 68.7 | 6.94 7.01 | 8.88 8.91 |
| 54 | —CH(CH$_3$)C(CH$_3$)$_2$— | n = 0 | H | SCH$_3$ | white semisolid | | 71.8 71.7 | 7.09 6.99 | 9.85 9.78 |
| 55 | —CH(CH$_3$)C(CH$_3$)$_2$— | n = 0 | OH | SCH$_3$ | white solid | 172.5–175 | 67.1 67.0 | 6.88 6.99 | 9.35 9.26 |
| 56 | —CH$_2$—C(CH$_3$)$_2$— | n = 0 | OCH$_3$ | SCH$_3$ | white solid | 130–132 | 68.0 68.0 | 6.71 6.57 | 9.32 9.21 |
| 57 | —CH$_2$—C(CH$_3$)$_2$— | n = 0 | OCH$_3$ | SO$_2$CH$_3$ | white solid | 125–127 | 61.4 61.9 | 6.06 6.25 | 8.43 8.55 |
| 58 | —CH$_2$—C(CH$_3$)$_2$— | 6-C$_3$H$_7$(n) | H | SCH$_3$ | off-white solid | 47–48 | 73.0 73.0 | 7.74 7.69 | 8.96 9.00 |
| 59 | —CH$_2$—C(CH$_3$)$_2$— | 6-C$_3$H$_7$(n) | OH | SCH$_3$ | white solid | 121–122 | 69.5 69.3 | 7.36 7.08 | 8.53 8.71 |
| 60 | —CH$_2$—C(CH$_3$)$_2$— | 5-NO$_2$ | H | SCH$_3$ | white solid | 153–154.5 | 60.9 61.2 | 5.93 5.61 | 13.3 13.4 |
| 61 | —CH$_2$—C(CH$_3$)$_2$— | 6-NH$_2$ | H | SCH$_3$ | colorless solid | 114–115 | 67.6 67.6 | 6.38 6.58 | 14.8 14.7 |

TABLE 1-continued 4,5-DISUBSTITUTED PYRIMIDINE COMPOUNDS

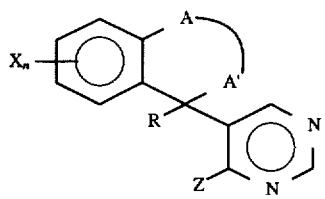

| Cpd No. | −A−A'− | $X_n$ | R | Z | Appearance | Melting Point °C. | Elem. Anal. calculated found %C | %H | %N |
|---|---|---|---|---|---|---|---|---|---|
| 62 | −CH$_2$−C(CH$_3$)$_2$− | 6-NO$_2$ | H | SCH$_3$ | white solid | 167–168 | 60.9 61.1 | 5.93 5.73 | 13.3 13.3 |
| 63 | −CH$_2$−C(CH$_3$)$_2$− | 6-NO$_2$ | OH | SCH$_3$ | white solid | 223–226 | | | |
| 64 | −CH$_2$−C(CH$_3$)$_2$− | 6-NH$_2$.HCl | H | SCH$_3$ | tan solid | 177–180 | 59.7 59.5 | 6.22 6.30 | 13.0 12.4 |
| 65 | −CH$_2$−C(CH$_3$)$_2$− | 6-N(SO$_2$CH$_3$)$_2$ | H | SCH$_3$ | white plates | 238–239 | 49.1 48.9 | 5.03 5.29 | 9.54 9.48 |
| 66 | −CH$_2$−C(CH$_3$)$_2$− | n = 0 | H | SO$_2$CH$_3$ | white crystals | 62–63 | 63.6 63.4 | 6.00 6.10 | 9.26 9.38 |
| 67 | −CH$_2$−C(CH$_3$)$_2$− | n = 0 | H | SOCH$_3$ | pale solid | | | | |
| 68 | −OCH$_2$O− (phenyl) | n = 0 | H | OCH$_3$ | white solid | 129–153 | 71.2 71.5 | 5.04 5.19 | 8.75 8.79 |
| 69 | −OCH$_2$O− (phenyl) | n = 0 | OH | OCH$_3$ | white solid | 191–194 | 67.9 68.1 | 4.80 4.87 | 8.33 8.59 |
| 70 | −OCH$_2$O− (phenyl) | n = 0 | H | SCH$_3$ | white crystals | 154.5–157 | 67.8 67.7 | 4.78 4.85 | 8.33 8.45 |
| 71 | −OCH$_2$O− (phenyl) | n = 0 | OH | SCH$_3$ | creamy white solid | 189–191.5 | 64.8 64.4 | 4.58 4.55 | 7.95 7.76 |
| 72 | −OCH$_2$O− (phenyl) | 2-CH$_3$ | H | OCH$_3$ | clear oil | | 71.8 72.0 | 5.43 7.73 | 8.38 8.06 |
| 73 | −OCH$_2$O− (phenyl) | 2-CH$_3$ | OH | OCH$_3$ | white solid | 87–89 | | | |
| 74 | −OCH$_2$O− (phenyl) | 2-CH$_3$, 3-CH$_3$ | H | OCH$_3$ | white solid | 123–125 | 72.8 72.9 | 5.24 5.17 | 8.09 8.08 |
| 75 | −OCH$_2$O− (phenyl) | 2-CH$_3$, 3-CH$_3$ | OH | OCH$_3$ | thick oil | | 69.2 69.1 | 5.53 5.52 | 7.69 7.62 |
| 76 | −OCH$_2$O− (phenyl-CH$_3$) | 2-CH$_3$ | H | OCH$_3$ | white solid | 160–163 | 72.4 72.3 | 5.80 5.82 | 8.04 8.09 |

TABLE 1-continued

4,5-DISUBSTITUTED PYRIMIDINE COMPOUNDS

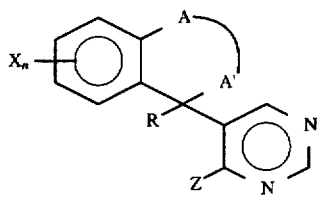

| Cpd No. | —A—A'— | $X_n$ | R | Z | Appearance | Melting Point °C. | Elem. Anal. calculated/found %C | %H | %N |
|---|---|---|---|---|---|---|---|---|---|
| 77 | —OCH₂O-(2-CH₃,4-CH₃-phenyl) | 2-CH₃ | OH | OCH₃ | thick oil | | | | |
| 78 | —OCH₂O-phenyl | n = 0 | F | OCH₃ | white solid | | | | |
| 79 | —OCH₂O-phenyl | 3-F | F | OCH₃ | white solid | 164–166 | | | |
| 80 | —OCH₂O-(2-CH₃,4-CH₃-phenyl) | 2-CH₃ | H | SCH₃ | white solid | 198.5–200 | 69.2 / 69.5 | 5.53 / 5.69 | 7.69 / 7.84 |
| 81 | —OCH₂O-(2-CH₃,4-CH₃-phenyl) | 2-CH₃ | OH | SCH₃ | white solid | 243.5–245 | | | |
| 82 | —OCH₂O-phenyl | 3-CH₃ | H | OCH₃ | white solid | 150–152 | | | |
| 83 | —OCH₂O-phenyl | 1-F | OH | OCH₃ | solid white foam | | | | |
| 84 | —OCH₂O-phenyl | 4-F | H | OCH₃ | | | | | |
| 85 | —OCH₂O-phenyl | 4-F | OH | OCH₃ | | | | | |
| 86 | —OCH₂O-phenyl | 4-CH₃ | H | OCH₃ | colorless foam | | | | |
| 87 | —OCH₂O-phenyl | 4-CH₃ | OH | OCH₃ | white solid | 200–203(d) | | | |

TABLE 1-continued 4,5-DISUBSTITUTED PYRIMIDINE COMPOUNDS

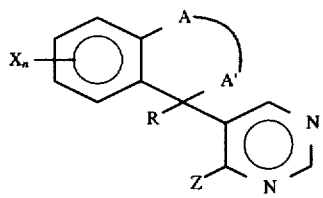

| Cpd No. | −A−A'− | $X_n$ | R | Z | Appearance | Melting Point °C. | Elem. Anal. calculated/found % C | % H | % N |
|---|---|---|---|---|---|---|---|---|---|
| 88 | −OCH₂O−(phenyl) | 4-F | H | SCH₃ | white solid | 159–159.5 | | | |
| 89 | −OCH₂O−(phenyl) | 4-F | OH | SCH₃ | white powder | 214–216 | | | |
| 90 | −OCH₂O−(phenyl) | n = 0 | H | SCH(CH₃)₂ | yellow solid | 130 | 69.2 / 69.2 | 5.53 / 5.74 | 7.69 / 7.77 |
| 91 | −OCH₂O−(phenyl) | n = 0 | OH | SCH(CH₃)₂ | off-white solid | 204 | | | |
| 92 | −OCH₂O−(phenyl) | n = 0 | H | SCH₂CH₃ | off-white powder | | 68.6 / 68.6 | 5.18 / 5.20 | 7.99 / 8.10 |
| 93 | −OCH₂O−(phenyl) | n = 0 | OH | SCH₂CH₃ | lt yellow solid | 183 | | | |
| 94 | −OCH₂O−(phenyl) | n = 0 | H | OCH₂CH=CH₂ | off-white powder | | 72.8 / 72.6 | 5.24 / 5.33 | 8.09 / 8.10 |
| 95 | −OCH₂O−(phenyl) | n = 0 | OH | OCH₂CH=CH₂ | cream solid | 184 | | | |
| 96 | −OCH₂O−(phenyl) | 2-CH₂CH₃ | H | OCH₃ | white solid | 135–137 | 72.4 / 72.0 | 5.79 / 5.87 | 8.09 / 8.11 |
| 97 | −OCH₂O−(phenyl) | 1-F | H | OCH₃ | off-white solid | | | | |
| 98 | −OCH₂O−(phenyl) | 1-CH₃ | H | OCH₃ | white solid | 130–135 | 71.8 / 72.1 | 5.43 / 5.49 | 8.38 / 8.47 |

TABLE 1-continued 4,5-DISUBSTITUTED PYRIMIDINE COMPOUNDS

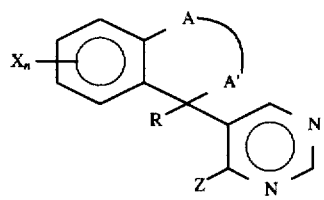

| Cpd No. | —A—A'— | $X_n$ | R | Z | Appearance | Melting Point °C. | Elem. Anal. calculated / found % C | % H | % N |
|---|---|---|---|---|---|---|---|---|---|
| 99 | —OCH₂O— (phenyl with F) | 2-CH₂CH₃ | H | OCH₃ | thick oil | | | | |
| 100 | —OCH₂O— (phenyl) | 3-F | H | OCH₃ | white solid | 144–148 | 67.5 / 67.5 | 4.47 / 4.76 | 8.28 / 8.28 |
| 101 | —OCH₂O— (phenyl) | 3-F | OH | OCH₃ | solid foam | | 64.8 / 64.5 | 5.17 / 4.93 | 7.56 / 7.47 |
| 102 | —OCH₂O— (phenyl) | 2-F | H | OCH₃ | lt yellow solid | 154–155 | | | |
| 103 | —CH₂CH₂— (phenyl) | n = 0 | H | OCH₃ | white crystals | 123–126 | 79.4 / 79.3 | 6.00 / 5.97 | 9.27 / 9.34 |
| 104 | —CH₂CH₂— (phenyl) | n = 0 | OH | OCH₃ | white crystals | 195–196.5 | 75.5 / 75.4 | 5.70 / 5.82 | 8.80 / 8.98 |
| 105 | —CH₂CH₂— (phenyl) | n = 0 | H | SCH₃ | white crystals | 129–129.5 | 75.4 / 75.3 | 5.70 / 5.71 | 8.80 / 8.92 |
| 106 | —CH₂CH₂— (phenyl) | n = 0 | OH | SCH₃ | white crystals | 208–209 | 71.8 / 72.1 | 5.42 / 5.94 | 8.35 / 8.32 |
| 107 | —CH₂CH₂— (phenyl) | 3-F | H | SCH₃ | white solid | 104–107 | 71.4 / 71.5 | 5.09 / 5.04 | 8.33 / 8.58 |
| 108 | —CH₂CH₂— (phenyl) | 3-F | OH | SCH₃ | tan solid | 211.5–213 | 68.2 / 68.1 | 4.86 / 4.69 | 7.95 / 7.93 |

TABLE 1-continued 4,5-DISUBSTITUTED PYRIMIDINE COMPOUNDS

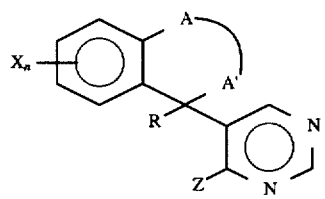

| Cpd No. | −A−A'− | $X_n$ | R | Z | Appearance | Melting Point °C. | Elem. Anal. calculated / found % C | % H | % N |
|---|---|---|---|---|---|---|---|---|---|
| 109 | −CH₂CH₂-[phenyl] | 2-Cl | H | SCH₃ | glassy solid | | 68.1 / 67.3 | 4.86 / 4.87 | 7.94 / 7.98 |
| 110 | −CH₂CH₂-[phenyl] | 2-Cl | OH | SCH₃ | white powder | 202–204 | | | |
| 111 | −CH₂CH₂-[phenyl] | n = 0 | H | SCH(CH₃)₂ | off-white powder | 133 | | | |
| 112 | −CH₂CH₂-[phenyl] | n = 0 | OH | SCH(CH₃)₂ | off-white powder | 200 | | | |
| 113 | −CH₂CH₂-[phenyl] | n = 0 | H | SCH₂CH₃ | yellow powder | 108 | 75.9 / 75.7 | 6.06 / 6.24 | 8.43 / 8.59 |
| 114 | −CH₂CH₂-[phenyl] | n = 0 | OH | SCH₂CH₃ | white powder | 159 | | | |
| 115 | −CH₂CH₂-[phenyl] | n = 0 | H | SOCH₃ | glassy solid | | | | |
| 116 | −CH₂CH₂-[phenyl] | n = 0 | H | SO₂CH₃ | oily solid | | | | |
| 117 | −CH₂C(CH₃)₂-[phenyl] | n = 0 | H | OCH₃ | cream solid | 152–156 | 80.0 / 79.9 | 6.71 / 6.79 | 8.48 / 8.38 |
| 118 | −O−C(CH₃)₂− | 5-CH₃ | H | OCH₃ | white solid | | 71.1 / 70.9 | 6.71 / 6.76 | 10.4 / 10.5 |
| 119 | −O−C(CH₃)₂− | 5-CH₃ | OH | OCH₃ | colorless oil | | 67.1 / 65.6 | 6.34 / 6.61 | 9.78 / 9.13 |
| 120 | −O−C(CH₃)₂− | 5-CH₃ | H | SCH₃ | colorless oil | | 67.1 / 66.8 | 6.34 / 6.42 | 9.78 / 9.20 |
| 121 | −O−C(CH₃)₂− | 5-CH₃ | OH | SCH₃ | white solid | | 63.6 / 63.0 | 6.00 / 5.80 | 9.26 / 9.01 |
| 122 | −O−C(CH₃)₂− | n = 0 | H | SCH₃ | white crystals | 95–96.5 | 66.1 / 66.2 | 5.92 / 9.82 | 10.3 / 10.5 |
| 123 | −O−C(CH₃)₂− | n = 0 | OH | SCH₃ | cream | 147– | 62.5 | 5.59 | 9.70 |

TABLE 1-continued 4,5-DISUBSTITUTED PYRIMIDINE COMPOUNDS

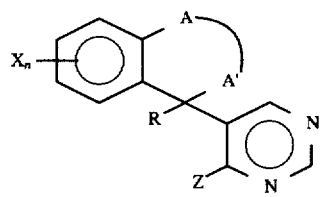

| Cpd No. | −A−A'− | $X_n$ | R | Z | Appearance | Melting Point °C. | % C calc/found | % H calc/found | % N calc/found |
|---|---|---|---|---|---|---|---|---|---|
| 124 | −O−CH₂C(CH₃)₂− | n = 0 | H | SCH₃ | solid off-white solid | 150.5 | 62.6 67.1 66.8 | 5.69 6.34 6.42 | 10.0 9.78 9.20 |
| 125 | −O−CH₂C(CH₃)₂− | n = 0 | OH | SCH₃ | white solid | | 63.6 62.2 | 6.00 5.55 | 9.26 9.43 |
| 126 | −CH₂CH₂C(CH₃)₂− | n = 0 | H | SCH₃ | white crystals | 117–121 | 71.8 71.9 | 7.09 7.21 | 9.85 10.0 |
| 127 | −CH₂CH₂C(CH₃)₂− | n = 0 | OH | SCH₃ | white solid | 208–209 | 68.0 67.8 | 6.71 6.62 | 9.33 9.36 |
| 128 | −CH₂CH=C(CH₃)− | n = 0 | CH₃ | SCH₃ | white solid | 121–129 | | | |
| 129 | −CH₂CH₂C(CH₃)₂− | n = 0 | H | SCH₂F | tan solid | 126–128 | 67.5 66.8 | 6.33 6.47 | 9.26 9.22 |
| 130 | −CH₂CH₂C(CH₃)₂− | 7-CH₃ | H | SCH₃ | white solid | 95–97 | 72.4 72.4 | 7.43 7.43 | 9.39 9.37 |
| 131 | −CH₂CH₂C(CH₃)₂− | 7-CH₃ | OH | SCH₃ | white solid | 181–182 | 68.8 68.4 | 7.05 7.16 | 8.91 8.89 |
| 132 | −CH₂CH₂C(CH₃)₂− | 7-CH₃ | H | SCH₂F | thick oil | | | | |
| 133 | −CH₂CH=C(CH₃)− | 7-CH₃ | CH₃ | SCH₃ | white solid | 119–125.5 | 72.9 73.0 | 6.80 6.89 | 9.45 9.51 |
| 134 | −CH(CH₃)C(CH₃)− | n = 0 | CH₃ | SCH₃ | off-white solid | | | | |
| 135 | −CH₂CH₂− | n = 0 | OH | SCH₃ | brown gum | | | | |
| 136 | −CH₂−C(CH₂CF₃)₂− | n = 0 | OH | SCH₃ | white crystals | 102–105 | | | |
| 137 | −CH₂−C(CH₂CH₃)₂− | n = 0 | H | SCH₃ | white solid | 102–105 | | | |
| 138 | −CH₂−CH(CH₂CH₃)− | n = 0 | C₂H₅ | SCH₃ | thick oil | | | | |
| 139 | −CH₂−(cyclopentyl) | n = 0 | H | SCH₃ | waxy yellow solid | | | | |
| 140 | −CH₂−(cyclopentyl) | n = 0 | OH | SCH₃ | white powder | | | | |
| 141 | −C(=O)CH₂− | n = 0 | H | SCH₃ | red solid | | | | |
| 142 | −C(=O)C(CH₃)₂− | 7-F | H | SCH₃ | colorless solid | 111.5–113 | 63.6 63.9 | 5.00 5.06 | 9.26 9.24 |
| 143 | −CH₂−C(CH₃)₂− | n = 0 | H | −SCH₂−(2-F-phenyl) | yellow oil | | 72.5 72.2 | 5.80 5.67 | 7.68 7.63 |
| 144 | −CH₂−C(CH₃)₂− | n = 0 | H | −SCH₂−(4-F-phenyl) | white solid | 92–94 | 72.5 72.7 | 5.80 5.79 | 7.68 7.72 |
| 145 | −CH₂−C(CH₃)₂− | n = 0 | H | −SCH₂−(2-CH₃-phenyl) | white solid | 84–86 | 76.6 76.5 | 6.70 6.73 | 7.77 7.79 |

TABLE 1-continued

4,5-DISUBSTITUTED PYRIMIDINE COMPOUNDS

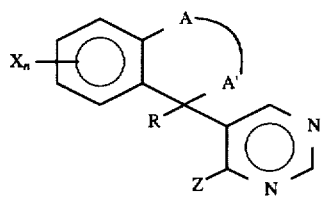

| Cpd No. | −A−A'− | $X_n$ | R | Z | Appearance | Melting Point °C. | Elem. Anal. calculated found % C | % H | % N |
|---|---|---|---|---|---|---|---|---|---|
| 146 | −CH₂−C(CH₃)₂− | n = 0 | H | −SCH₂−C₆H₄−CH₃ (para) | white solid | 89–91 | 76.6 76.7 | 6.70 6.84 | 7.77 7.81 |
| 147 | −CH₂−C(CH₃)₂− | n = 0 | H | −SCH₂−C₆H₄−CF₃ (meta) | yellow oil | | 66.6 66.3 | 5.10 5.07 | 6.75 6.65 |
| 148 | −CH₂−C(CH₃)₂− | n = 0 | H | −SCH₂−C₆H₄−F (meta) | white solid | 60–62 | 72.5 72.6 | 5.80 5.79 | 7.68 7.73 |
| 149 | −CH₂−C(CH₃)₂− | n = 0 | H | −SCH₂−C₆H₄−CH₃ (meta) | oil | | 76.6 76.5 | 6.70 6.69 | 7.77 7.64 |
| 150 | −CH₂−C(CH₃)₂− | n = 0 | H | −SCH₂−C₆H₄−NO₂ (para) | white solid | 132–134 | 67.5 67.5 | 5.40 5.33 | 10.7 10.5 |
| 151 | −CH₂−C(CH₃)₂− | n = 0 | H | −SCH₂−C₆H₄−NO₂ (meta) | brown oil | | 67.5 65.9 | 5.40 5.33 | 10.7 10.3 |
| 152 | −CH₂−C(CH₃)₂− | n = 0 | H | −SCH₂−C₆H₄−NO₂ (ortho) | white solid | 111–113 | 67.5 67.7 | 5.40 5.18 | 10.7 10.8 |
| 153 | −CH₂−C(CH₃)₂− | n = 0 | H | −SCH₂−C₆H₄−CF₃ (para) | yellow oil | | 66.6 66.6 | 5.10 5.16 | 6.75 6.75 |
| 154 | −CH₂−C(CH₃)₂− | n = 0 | H | −SCH₂−C₆H₄−CF₃ (ortho) | yellow oil | | 66.6 69.8 | 5.10 5.42 | 6.75 7.18 |
| 155 | −CH₂−C(CH₃)₂− | n = 0 | H | −SCH₂−(2-Cl-pyridyl) | white solid | 126–128 | 66.0 66.0 | 5.23 5.27 | 11.0 11.0 |
| 156 | −CH₂−C(CH₃)₂− | n = 0 | H | −SCH₂OCH₃ | oil | | 68.0 67.9 | 6.71 6.63 | 9.32 9.41 |
| 157 | −CH₂−C(CH₃)₂− | n = 0 | H | SCH₂CH(OH)CH₂Cl | yellow oil | | | | |
| 158 | −CH₂−C(CH₃)₂− | n = 0 | H | SCHF₂ | white | 62– | 62.7 | 5.26 | 9.14 |

TABLE 1-continued 4,5-DISUBSTITUTED PYRIMIDINE COMPOUNDS

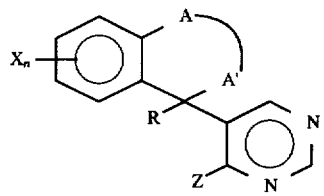

| Cpd No. | —A—A'— | $X_n$ | R | Z | Appearance | Melting Point °C. | Elem. Anal. calculated/found % C | % H | % N |
|---|---|---|---|---|---|---|---|---|---|
| | | | | | solid | 64 | 62.6 | 5.41 | 9.06 |
| 159 | —CH$_2$—C(CH$_3$)$_2$— | n = 0 | H | SCH$_2$C$_6$H$_5$ | white solid | 76–79 | 76.3 75.2 | 6.4. 6.27 | 8.09 8.00 |
| 160 | —CH$_2$—C(CH$_3$)$_2$— | n = 0 | OH | SCH$_2$CO$_2$CH$_3$ | lt. yellow solid | 139–140.5 | 62.8 62.5 | 5.85 6.00 | 8.13 8.14 |
| 161 | —CH$_2$—C(CH$_3$)$_2$— | n = 0 | H | SCH$_2$CO$_2$C$_2$H$_5$ | lt. yellow oil | | 66.6 66.7 | 6.48 6.81 | 8.18 8.34 |
| 162 | —CH$_2$—C(CH$_3$)$_2$— | n = 0 | OH | SCH$_2$CO$_2$H | lt. yellow powder | 128–130(d) | 61.8 61.7 | 5.49 5.47 | 8.48 8.46 |
| 163 | —CH$_2$—C(CH$_3$)$_2$— | n = 0 | H | OCH$_2$CO$_2$C$_2$H$_5$ | colorless oil | | 69.9 70.3 | 6.79 7.03 | 8.58 8.63 |
| 164 | —CH$_2$—C(CH$_3$)$_2$— | n = 0 | H | OCH$_2$CF$_3$ | colorless oil | | 63.4 63.0 | 5.32 5.35 | 8.69 8.63 |
| 165 | —CH$_2$—C(CH$_3$)$_2$— | n = 0 | H | OCH$_2$CH=CH$_2$ | colorless oil | | 77.1 77.0 | 7.19 7.26 | 9.99 10.2 |
| 166 | —CH$_2$—C(CH$_3$)$_2$— | n = 0 | H | OCH$_2$CH$_2$OCH$_3$ | colorless oil | | 72.5 72.7 | 7.43 7.78 | 9.39 9.59 |
| 167 | —CH$_2$—C(CH$_3$)$_2$— | n = 0 | H | OCH$_2$CH$_2$SCH$_3$ | oil | | | | |
| 168 | —CH$_2$—C(CH$_3$)$_2$— | n = 0 | H | OCH$_2$CH$_2$N(CH$_3$)$_2$ | oil | | 73.3 72.8 | 8.09 8.14 | 13.4 13.4 |
| 169 | —CH$_2$—C(CH$_3$)$_2$— | n = 0 | H | OCH$_2$CH$_2$SO$_2$CH$_3$ | pale oil | | | | |
| 170 | —CH$_2$—C(CH$_3$)$_2$— | n = 0 | H | NHCH$_3$ | oil | | | | |
| 171 | —CH$_2$—C(CH$_3$)$_2$— | n = 0 | H | NHC$_2$H$_5$ | oil | | | | |
| 172 | —CH$_2$—C(CH$_3$)$_2$— | n = 0 | H | NH$_2$ | tan powder | | | | |
| 173 | —CH$_2$—C(CH$_3$)$_2$— | n = 0 | H | NHCH$_2$CH$_2$OCH$_3$ | oil | | | | |
| 174 | —CH$_2$—C(CH$_3$)$_2$— | n = 0 | H | SC$_6$H$_5$ | oil | | 75.9 75.7 | 6.60 6.02 | 8.43 8.32 |
| 175 | —CH$_2$—C(CH$_3$)$_2$— | n = 0 | H | SCH$_2$CF$_3$ | white needles | | | | |
| 176 | —CH$_2$—C(CH$_3$)$_2$— | n = 0 | H | SCH$_2$CH=CH$_2$ | pale oil | | | | |
| 177 | —CH$_2$—C(CH$_3$)$_2$— | n = 0 | H | SCH$_2$F | tan solid | 67.5–69 | 66.6 66.8 | 5.94 6.03 | 9.71 9.86 |
| 178 | —CH$_2$—C(CH$_3$)$_2$— | n = 0 | H | SCF$_3$ | white solid | 60–62 | 59.3 59.1 | 4.67 4.67 | 8.64 8.68 |
| 179 | —CH$_2$—C(CH$_3$)$_2$— | n = 0 | H | SCH$_2$CH=CHC$_6$H$_5$ | yellow oil | | 77.7 77.0 | 6.78 6.45 | 7.29 7.39 |
| 180 | —CH$_2$—C(CH$_3$)$_2$— | n = 0 | H | SH | yellow solid | 184–186 | 70.3 70.0 | 6.28 6.20 | 10.9 10.8 |
| 181 | —CH$_2$—C(CH$_3$)$_2$— | 6-OCH$_3$ | H | SO$_2$CH$_3$ | yellow oil | | 61.4 61.4 | 6.02 5.99 | 8.42 8.30 |
| 182 | —CH$_2$—C(CH$_3$)$_2$— | 6-OCH$_3$ | H | SCH$_2$CH=CH$_2$ | yellow oil | | | | |
| 183 | —CH$_2$—C(CH$_3$)$_2$— | 6-OCH$_3$ | H | SCH$_2$C$_6$H$_5$ | off-white crystals | 100–102 | | | |
| 184 | —O—CH$_2$C(CH$_3$)$_2$— | n = 0 | H | SCH$_2$F | white solid | 117–118 | | | |
| 185 | —O—CH$_2$C(CH$_3$)$_2$— | 6-CH(CH$_3$)$_2$ | H | SCH$_2$F | off-white solid | | | | |
| 186 | —O—CH$_2$C(CH$_3$)$_2$— | 6-F | OH | SCH$_3$ | yellow solid | 168–170 | 59.2 59.3 | 5.35 5.31 | 8.74 8.86 |
| 187 | —O—CH$_2$C(CH$_3$)$_2$— | 6-F | H | SCH$_3$ | white solid | 121–123 | 63.1 63.1 | 5.63 5.95 | 9.26 9.06 |
| 188 | —O—CH$_2$C(CH$_3$)$_2$— | n = 0 | H | SCH$_2$C$_6$H$_5$ | thick oil | | 72.9 72.9 | 6.12 6.25 | 7.73 7.53 |
| 189 | —O—CH$_2$C(CH$_3$)$_2$— | n = 0 | H | SCH$_2$CH=CH$_2$ | thick oil | | 69.2 69.8 | 6.45 6.46 | 8.99 9.00 |
| 190 | —O—CH$_2$C(CH$_3$)$_2$— | 6-CH$_3$ | OH | SCH$_3$ | white solid | 156–158 | 64.6 64.4 | 6.40 6.18 | 9.04 9.02 |
| 191 | —O—CH$_2$C(CH$_3$)$_2$— | 6-CH$_3$ | H | SCH$_3$ | white crystals | 118–119 | 68.0 68.0 | 6.66 6.79 | 9.33 9.25 |
| 192 | —O—CH$_2$C(CH$_3$)$_2$— | 6-CH(CH$_3$)$_2$ | OH | SCH$_3$ | white | 163– | | | |

TABLE 1-continued 4,5-DISUBSTITUTED PYRIMIDINE COMPOUNDS

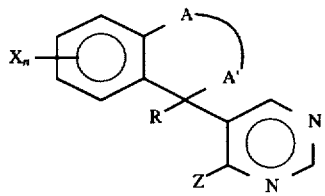

| Cpd No. | —A—A'— | $X_n$ | R | Z | Appearance | Melting Point °C. | Elem. Anal. calculated found % C | % H | % N |
|---|---|---|---|---|---|---|---|---|---|
| 193 | —O—CH$_2$C(CH$_3$)$_2$— | 6-CH(CH$_3$)$_2$ | H | SCH$_3$ | white solid | 118–120 | 69.5 / 69.5 | 7.36 / 7.42 | 8.53 / 8.46 |
| 194 | —O—CH$_2$C(CH$_3$)$_2$— | n = 0 | H | SO$_2$CH$_3$ | white solid | 128–130 | 72.9 / 72.9 | 6.12 / 6.25 | 7.73 / 7.53 |
| 195 | —O—CH$_2$C(CH$_3$)$_2$— | 6-CH(CH$_3$)$_2$ | H | SO$_2$CH$_3$ | off-white solid | 146–149 | | | |
| 196 | —O—CH$_2$C(CH$_3$)$_2$— | 6-CH$_2$CH$_3$ | OH | SCH$_3$ | yellow solid | 152–153 | 65.4 / 64.3 | 6.66 / 6.47 | 8.47 / 8.62 |
| 197 | —O—CH$_2$C(CH$_3$)$_2$— | 6-CH$_2$CH$_3$ | H | SCH$_3$ | white solid | 115–117 | 68.8 / 68.5 | 7.09 / 7.08 | 8.91 / 8.98 |
| 198 | —S—CH$_2$C(CH$_3$)$_2$— | n = 0 | OH | SCH$_3$ | yellow solid | 246–247 | | | |
| 199 | —S—CH$_2$C(CH$_3$)$_2$— | n = 0 | H | SCH$_3$ | white crystals | 124–126 | 63.4 / 63.0 | 6.00 / 6.08 | 9.26 / 9.25 |
| 200 | —SO$_2$—CH$_2$C(CH$_3$)$_2$— | n = 0 | H | SO$_2$CH$_3$ | yellow crystals | 202–208(d) | | | |
| 201 | —SO$_2$—CH$_2$C(CH$_3$)$_2$— | n = 0 | H | SCH$_3$ | white crystals | 222–224 | | | |
| 202 | —CH$_2$—C(CH$_3$)$_2$— | n = 0 | OH | SH | lt. yellow powder | 205–208 | | | |
| 203 | —CH$_2$—C(CH$_3$)$_2$— | 7-F | H | SCH$_3$ | white solid | 81–82 | 66.6 / 66.5 | 5.94 / 5.88 | 9.71 / 9.67 |
| 204 | —CH$_2$—C(CH$_3$)$_2$— | 6-SCH$_3$ | H | SCH$_3$ | lt. gold oil | | 64.5 / 64.3 | 6.37 / 6.20 | 8.85 / 9.04 |
| 205 | —O—CH$_2$C(CH$_3$)$_2$— | 8-Br 6-CH(CH$_3$)$_2$ | H | SCH$_3$ | thick semi-solid | | | | |
| 206 | —CH$_2$—C(CH$_3$)$_2$— | n = 0 | OH | SO$_2$CH$_3$ | colorless crystals | 152–156 | | | |
| 207 | —CH$_2$—C(CH$_3$)$_2$— | 6-NHSO$_2$CH$_3$ | H | SCH$_3$ | tan solid | 82–85 | 55.9 / 55.6 | 6.34 / 6.09 | 11.5 / 11.2 |
| 208 | —CH$_2$—C(CH$_3$)$_2$— | 6-NHSO$_2$C$_6$H$_5$ | H | SCH$_3$ | tan solid | 174–176 | 62.1 / 61.8 | 5.45 / 5.54 | 9.87 / 9.77 |
| 209 | —CH$_2$—C(CH$_3$)$_2$— | 6-CN | H | SCH$_3$ | lt. yellow solid | 157–158 | 69.1 / 69.1 | 5.80 / 5.89 | 14.2 / 14.3 |
| 210 | —CH$_2$—C(CH$_3$)$_2$— | n = 0 | H | CN | lt. tan solid | 55–56 | 77.1 / 77.0 | 6.06 / 5.91 | 16.9 / 16.8 |
| 211 | —CH$_2$—C(CH$_3$)$_2$— | n = 0 | OH | CN | tan gum | | | | |
| 212 | —CH$_2$—C(CH$_3$)$_2$— | n = 0 | H | CO$_2$CH$_3$ | colorless solid | 43.5–45 | 72.4 / 72.4 | 6.43 / 6.39 | 9.92 / 9.79 |
| 213 | —C(=O)—C(CH$_3$)(CH$_2$CH$_3$)— | n = 0 | H | SCH$_3$ | lt. brown oil | | | | |
| 214 | —C(=O)—C(CH$_3$)$_2$— | n = 0 | H | SCH$_3$ | colorless solid | 76–77 | 67.6 / 67.5 | 5.67 / 5.72 | 9.85 / 9.57 |
| 215 | —CH$_2$CH$_2$C(CH$_3$)$_2$— | n = 0 | H | SO$_2$CH$_3$ | colorless solid | 118.5–120 | 64.5 / 64.6 | 6.37 / 6.39 | 8.85 / 8.93 |
| 216 | —CH$_2$C(CH$_3$)(CH$_2$CH$_3$)— | n = 0 | H | SCH$_3$ | white solid | 75–84 | 71.6 / 71.3 | 7.04 / 6.59 | 9.85 / 9.69 |
| 217 | —O—CH$_2$C(CH$_3$)$_2$— | 6-CH$_2$CH$_3$ | H | SO$_2$CH$_3$ | white crystals | 120–122 | 62.4 / 62.5 | 6.35 / 6.41 | 8.09 / 8.09 |
| 218 | —O—CH$_2$C(CH$_3$)$_2$— | 6-F | H | SO$_2$CH$_3$ | white solid | 143–144 | 57.1 / 57.4 | 5.05 / 5.15 | 8.32 / 8.07 |
| 219 | —O—CH$_2$C(CH$_3$)$_2$— | 6-CH$_2$CH$_3$ | OCH$_3$ | SCH$_3$ | off-white crystals | 114–116 | 66.3 / 66.2 | 7.02 / 7.05 | 8.12 / 8.10 |
| 220 | —CH$_2$CH$_2$C(CH$_3$)$_2$— | n = 0 | H | OCH$_3$ | colorless solid | 65–66 | 76.1 / 76.1 | 7.51 / 7.70 | 10.4 / 10.4 |
| 221 | —CH$_2$C(CH$_3$)(CH$_2$CH$_3$)— | n = 0 | H | SO$_2$CH$_3$ | clear, thick oil | | 64.5 / 64.8 | 6.37 / 6.49 | 8.88 / 8.93 |
| 222 | —CH$_2$—C(CH$_3$)$_2$— | n = 0 | H | CONH$_2$ | tan solid | 140–143 | | | |

TABLE 1-continued 4,5-DISUBSTITUTED PYRIMIDINE COMPOUNDS

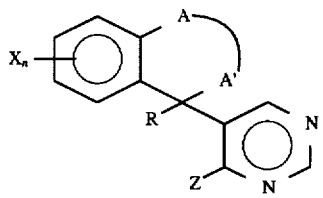

| Cpd No. | −A−A'− | X_n | R | Z | Appearance | Melting Point °C. | Elem. Anal. calculated found %C | %H | %N |
|---|---|---|---|---|---|---|---|---|---|
| 223 | −CH$_2$−C(CH$_3$)$_2$− | n = 0 | H | CO$_2$H | colorless solid | 172–173(d) | 71.6 71.3 | 6.01 5.98 | 10.4 10.3 |
| 224 | −CH$_2$−C(CH$_3$)$_2$− | n = 0 | OC$_2$H$_5$ | SCH$_3$ | yellow oil | oil | 68.8 68.8 | 6.98 7.05 | 8.94 8.90 |
| 225 | −CH$_2$−C(CH$_3$)$_2$− | n = 0 | OC$_2$H$_5$ | SO$_2$CH$_3$ | white solid | 96–98 | | | |
| 226 | −CH$_2$−C(CH$_3$)$_2$− | n = 0 | H | SCH$_2$CH$_2$C$_6$H$_5$ | colorless oil | oil | 76.3 76.1 | 6.71 6.86 | 7.77 7.87 |
| 227 | −CH$_2$−C(CH$_3$)$_2$− | n = 0 | H | N(CH$_3$)SO$_2$CH$_3$ | colorless solid | 176–177 | 57.6 57.3 | 4.43 4.35 | 11.2 11.0 |
| 228 | −CH$_2$−C(CH$_3$)$_2$− | n = 0 | H | SCH$_3$, N-oxide | colorless solid | 172–173 | 67.1 67.2 | 6.34 6.58 | 9.78 9.91 |
| 229 | −CH$_2$−C(CH$_3$)$_2$− | n = 0 | H | SO$_2$CH$_3$, N-oxide | colorless solid | 164–165 | 60.4 60.1 | 5.70 5.83 | 8.80 8.79 |
| 230 | −CH$_2$CH$_2$C(CH$_3$)$_2$− | n = 0 | H | SO$_2$CH$_3$, N-oxide | colorless solid | 154–155 | 61.4 61.4 | 6.06 6.06 | 8.43 8.39 |
| 231 | −CH$_2$−C(CH$_3$)$_2$− | n = 0 | H | SO$_2$NHCH$_3$ | white solid | 152–160 | 60.5 59.1 | 6.03 5.87 | 13.2 12.8 |
| 232 | −CH$_2$−C(CH$_3$)$_2$− | n = 0 | H | SO$_2$N(CH$_3$)$_2$ | white solid | 94–95 | 61.6 61.5 | 6.39 6.34 | 12.7 12.6 |
| 233 | −CH$_2$−C(CH$_3$)$_2$− | n = 0 | H | SO$_2$NH$_2$ | white powder | 116–136 | 59.4 61.4 | 5.65 5.64 | 13.9 12.4 |
| 234 | −CH$_2$−C(CH$_3$)$_2$− | n = 0 | H | SO$_2$NHCH(CH$_3$)$_2$ | white solid | | | | |

The carbon atom of the polycyclic substituent that is attached to the pyrimidine ring of the compounds of Formula I is an asymmetric carbon atom and, therefore, the compounds exist in two stereoisomeric forms. Other asymmetric carbon atoms are also present in certain of the compounds and, in those instances, multiple stereoisomers exist. Certain of the compounds can also exist in two or more geometric isomer forms. These optical and geometric isomers have different levels of herbicidal activity. Nevertheless, the invention and the compounds of Formula I expressly include each of these isomers independently as well as in mixtures with other isomers.

The term alkyl as used herein includes straight chain, branched chain, and cyclic moieties. Thus, typical alkyl groups are methyl, ethyl, 1-methylethyl, propyl, cyclopropyl and the like. Methyl and ethyl are often preferred. Typical alkyl groups substituted with up to the maximum number of fluorine atoms include trifluoromethyl, monofluoromethyl, 2,2,2-trifluoroethyl, 2,3-difluoropropyl, and the like; trifluoromethyl is often preferred.

The compounds of Formula I wherein R represents hydroxyl can generally be prepared by the reaction of a 5-bromo-4-substituted pyrimidine compound of Formula II:

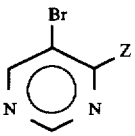

wherein Z is as defined for compounds of Formula I (except that chloro, bromo, fluoro, and alkanesulfonyl moieties are contraindicated), an alkyl lithium compound, and a polycyclic keto compound of Formula III:

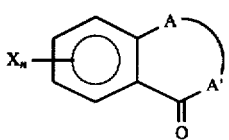

wherein X$_n$ and the fragment:

are as defined for compounds of Formula I. The reaction is typically carried out by preparing a solution of the 5-bromo-4-substituted pyrimidine compound and the polycyclic keto compound in anhydrous tetrahydrofuran, cooling the mixture to about −70° C., and then adding a hexane solution of an alkyl lithium compound (typically butyl lithium) slowly (typically by means of a syringe) with cooling and stirring. After a few minutes, the mixture is allowed to warm to about −20° C. and water is added. The resulting phases are separated and the organic phase is diluted with ether or dichloromethane and washed with water. The desired product can be obtained by removing the solvents by evaporation or distillation and can be purified by standard methods, such as recrystallization or chromatography.

Compounds of Formula I wherein R represents other than hydroxyl (i.e., hydrogen, fluorine, chlorine, bromine, methyl, ethyl, propyl, methoxy, ethoxy, or propoxy) can be prepared from corresponding compounds of Formula I wherein R represents hydroxyl by adaptations of known methods. Thus, compounds wherein R represents chlorine can be prepared by reaction of hydroxyl compounds with thionyl chloride under reaction conditions known in the art for related reactions. The chloro compounds of Formula I can be converted to compounds wherein R represents fluoro by treatment with potassium fluoride or antimony trifluoride and to compounds wherein R represent bromo by treatment with sodium bromide or boron tribromide. Compounds wherein R represents F can also be prepared by reaction of the corresponding compound wherein R represents hydroxyl with diethylaminosulfur trifluoride. Some compounds of Formula I wherein R represents methoxy, ethoxy, or propoxy can be prepared by treatment of chloro compounds of Formula I with the corresponding alkali metal alkoxide in alcohol solution, such as sodium methoxide in methanol or potassium ethoxide in ethanol. Compounds wherein R represents an alkoxy group can also be prepared by alkylation of the corresponding hydroxyl compounds with an alkyl halide, such as methyl bromide, ethyl iodide, or propyl bromide under reaction conditions known in the art for related reactions.

Compounds of Formula I wherein R represents hydrogen can be prepared from corresponding compounds wherein R represents hydroxyl by treatment with triethylsilane and boron trifluoride etherate. The reaction is generally carried out by adding an excess of triethyl silane and boron trifluoride etherate to a cold solution of the hydroxy compound in a solvent, such as dichloromethane, and allowing the mixture to react for several hours. The product can be recovered by conventional means. Compounds of Formula I wherein R represents alkyl (methyl, ethyl, or propyl) are often produced as by-products during this reduction procedure. These products can be obtained as the principal products by treating the compound of Formula I wherein R represents hydroxy with boron trifluoride etherate and allowing the mixture to react before adding the triethylsilane.

Compounds of Formula I wherein R represents H can also be prepared by reduction of the corresponding compounds of Formula I wherein R represents F with lithium aluminum hydride.

Compounds of Formula I wherein Z represents alkanesulfinyl or alkanesulfonyl, including methanesulfonyl, can be prepared by oxidation of the corresponding compound of Formula I wherein Z represents alkylthio, such as methylthio, with an oxidizing agent such as meta-chloroperbenzoic acid under reaction conditions known in the art for such transformations. When meta-chloroperbenzoic acid is used in excess, a mixture of an alkanesulfonyl compound and its N-oxide derivative are obtained. The N-oxide derivative is the primary product when a large excess of meta-chloroperbenzoic acid is used and the reaction is allowed to proceed for eighteen or more hours.

Compounds of Formula II wherein Z represents chloro can be prepared by the reaction of 5-bromopyrimidine with peracetic acid in an acidic medium and subsequent reaction of the 5-bromo-4-hydroxypyrimidine intermediate formed with phosphorus oxychloride in acetonitrile.

Compounds of Formula II wherein Z represents optionally substituted alkoxy, alkylthio, alkenyloxy, alkenylthio, alkynyloxy, alkynylthio, phenoxy, phenylthio, fluoro, chloro, cyano, or dialkylamino as defined hereinbefore and R represents hydrogen or alkyl can be prepared by treatment of a compound of Formula II wherein Z represents chloro or methanesulfonyl with an appropriate reagent. Examples include treatment with an alkali metal salt of an alkanol, alkenol, alkynol, phenol, alkanethiol, alkenethiol, alkynethiol, or thiophenol under reaction conditions known in the art to promote similar displacement reactions of 4-chloro or 4-methanesulfonylpyrimidine compounds with alkali metal salts of alcohols and mercaptans. Similarly, 4-fluoro, bromo, and cyano compounds can be prepared by the reaction of potassium fluoride, bromide, or cyanide and 4-amino and alkylamino compounds can be prepared by the reaction of excess ammonia or alkylamine with the corresponding 4-chloro or 4-methanesulfonyl compound under reaction conditions typical of similar reactions known in the art. In a like manner, 4-alkylsulfonylamino compounds can be prepared by the reaction of an alkali metal salt of an alkylsulfonamide compound with 4-chloro or 4-methanesulfonylpyrimidine compounds. The same transformations can be carried out on 5-polycyclyl-4-(chloro or methanesulfonyl)pyrimidine N-oxide compounds.

Compounds of Formula I wherein Z represents optionally substituted alkylthio (including benzylthio), alkenylthio, alkynylthio can be also be prepared by reaction of the corresponding 4-thiol compound with an optionally substituted alkyl (including benzyl), alkenyl, or alkynyl chloride or bromide in the presence of a base under conditions known in the art for related alkylation reactions. The 4-thiol compounds can be prepared by reaction of a 4-methylthio compound of Formula I with excess sodium methanethiolate in a dipolar, aprotic solvent or methanol.

Compounds of Formula I wherein Z represents monofluoromethylthio can be made by fluorination of the corresponding methylthio compound with 1-chloromethyl-4-fluoro-1,4-diazoniabicyclo|2.2.2|octane bis (tetrafluoroborate) in acetonitrile.

Compounds of Formula I wherein Z represents an N-(alkyl, alkenyl, alkynyl, phenyl, or pyridinyl) aminosulfonyl moiety can be prepared from the corresponding compound of Formula I wherein Z represents benzylthio by chloroxidation under typical chloroxidation reaction conditions to obtain a reactive intermediate wherein Z represents the chlorosulfonyl group and subsequent treatment of this intermediate with ammonia or an amine under reaction conditions typical of those in the art for the preparation of sulfonamide compounds from chlorosulfonyl compounds.

Some compounds of Formula I can alternately be prepared from polycyclic keto compounds of Formula III by building the pyrimidinyl moiety from acylic reagents. The reaction of compounds of Formula III with ethyl diethoxyphosphonylacetate and sodium hydride produces a compound of Formula IV:

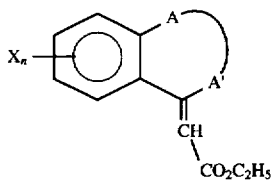

which can be reduced with hydrogen using a palladium on carbon catalyst to obtain a substituted acetic acid of Formula V:

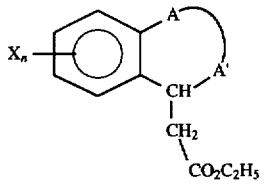

Compounds of Formula V can generally be treated with methyl formate and lithium diisopropylamide to obtain a further intermediate of Formula VI:

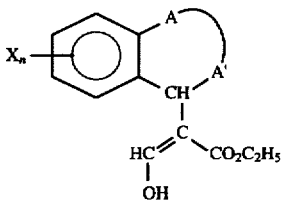

Intermediates of Formula VI can be converted to 4-pyrimidinone compounds useful as intermediates by a variety of methods, including condensation with an unsaturated 1,3-diamino compound, such as an amidine or an S-alkylisothiourea compound.

Many compounds of Formula I wherein —A-A'— represents —CH$_2$—CR'$_2$— or —C(O)—CR'$_2$— and R represents H, methyl, ethyl, or propyl can be also prepared from 5-bromo-4-(substituted)pyrimidine compounds. Reaction of the pyrimidine compound with n-butyl lithium and then an appropriately substituted benzaldehyde compound in anhydrous tetrahydrofuran at temperatures of about -25° C. leads to an (appropriately substituted-phenyl)(4-(substituted)-5-pyrimidinyl)methanol compound of Formula VII:

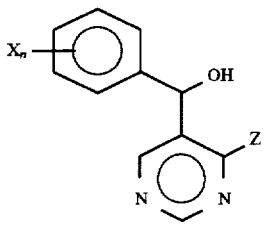

wherein X, n, and Z are as defined hereinbefore. These compounds can be converted to the corresponding chloromethane derivatives by treatment with thionyl chloride in an inert solvent. Compounds of Formula VIII:

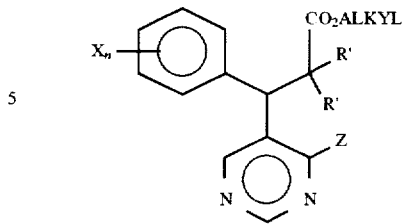

can be obtained by treatment of such chloromethane compounds with the salt formed on reaction of lithium diisopropylamide with an ester of an alkanoic acid, such as 2-methylpropanoic acid, in tetrahydrofuran at temperatures of about -10° C. Compounds of Formula VIII can be converted to compounds of Formula I wherein —A-A'— represents —C(O)—CR'$_2$— by hydrolysis of the ester to obtain the corresponding acid and subsequent treatment with Eaton's acid at about 75° C. Compounds of Formula I wherein —A-A'— represents —CH$_2$CR'$_2$— can be prepared from such compounds by reduction with triethylsilane and boron trifluoride etherate in refluxing 1,2-dichloroethane.

Polycyclic keto compounds of Formula III can be prepared by a variety of known methods and many such compounds are known in the art. Dibenzodioxocin-12-one compounds, that is, compounds of Formula III wherein D represents a methylenedioxy moiety (—O—CR'$_2$—O—) can be prepared by the reaction of the correspondingly substituted 2,2'-dihydroxybenzophenone compound with dibromomethane or other appropriate dibromoalkane and an anhydrous base, such as potassium carbonate. The reaction is typically carried out by heating the reactants in a dipolar, aprotic solvent, such as dimethyl sulfoxide. Dibenzosuberone compounds, compounds of Formula III wherein D represent an ethylene moiety (—CR'$_2$—CR'$_2$—) can be prepared by ring closure of an appropriately substituted 2-(2-phenethyl)benzoic acid compound with a mixture of phosphorus pentoxide and methanesulfonic acid (Eaton's acid). Appropriately substituted 2-(2-phenethyl)benzoic acid compounds can be prepared in a variety of ways as is known in the art. Many can be prepared by treatment of an appropriately substituted phthalic anhydride with an appropriately substituted phenylacetic acid compound at a temperature of about 250° C. in the presence of sodium acetate and subsequent reduction of the intermediate obtained with red phosphorus and hydrogen iodide in an inert atmosphere. Other appropriately substituted 2-(2-phenethyl)benzoic acid compounds can be prepared by treatment of an appropriately substituted 2-methylbenzoic acid compound with lithium diisopropylamide and then an appropriately substituted benzyl halide at temperatures below about -70° C.

Many compounds of Formula III wherein —A-A'— represents a chain of 2 or 3 —CR'$_2$— units (1-indanones and 1-tetralinones, respectively) can be prepared by the reaction of an appropriately substituted benzene compound with an appropriate chloroalkanoic acid chloride of the formula Cl—CR'$_2$—CR'$_2$—COCl or Cl—CR'$_2$—CR'$_2$—CR'$_2$—COCl catalyzed by a Lewis acid, such as aluminum chloride. Thus, as is known in the art, 2,2-dimethylindanone can be prepared by the reaction of benzene and 2-chloropivaloyl chloride. Alkyl groups, such as methyl can be added to the 2-position of 1-indanones and 1-tetralinones by treatment with a base, such as sodium carbonate, and an alkyl halide, such as methyl bromide.

Compounds of Formula III wherein —A-A'— represents a —O—CR'$_2$— moiety (coumaranones) and their sulfur analogs can be prepared by the reaction of an appropriately substituted 2-haloalkanoylphenol or thiophenol compound with sodium hydride in tetrahydrofuran. Appropriately substituted 2-haloalkanoylphenol or thiophenol compounds can be prepared in a variety of ways, including the reaction of an appropriately substituted anisole or methylthiobenzene compound with a 2-bromoalkanoyl chloride compound in the presence of aluminum chloride. Compounds of Formula III wherein —A-A'— represents a —O—CR'$_2$CR'$_2$— (chromanones) and their sulfur analogs can be prepared by the reaction of an appropriately substituted anisole or alkylthiobenzene with a 3-chloroalkanoyl chloride and aluminum chloride, dealkylation with boron tribromide, and ring closure of the resulting phenol or thiophenol intermediate with a base, such as sodium carbonate. Alkyl groups, such as methyl can be added to the carbon adjacent to the carbonyl group of coumaranones and chromanones (and their sulfur analogs) by treatment with a base, such as sodium carbonate and an alkyl halide, such as methyl bromide.

While it is possible to utilize the 4-substituted 5-polycyclylpyrimidine compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants, such as water, before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, 2-propanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with water before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-C$_{18}$ ethoxylate; alcohol-alkylene oxide addition products, such as tridecyl alcohol-C$_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetration aids, spreading agents, sticking agents, dispersing agents, thickening agents, freeze point depressants, antimicrobial agents, and the like. The compositions can also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The compounds of Formula I have been found to be useful preemergence and postemergence herbicides. They can be employed at non-selective (higher) rates of application to control essentially all of the vegetation in an area or, in some cases, at selective (lower) rates of application for the selective control of undesirable vegetation in turf and in valuable crops such as rice, wheat, barley, corn, soybeans, and cotton; especially in rice or in broadleaf crops, such as soybeans and cotton. Grassy weeds are especially well controlled. The selective control of such weeds growing in broadleaf crops, such as cotton and soybeans, is most evident when the compounds are applied preemergence. The selective control of weeds growing in rice crops is most evident when the compounds are applied in paddy water after the rice is established. While each of the 4-substituted 5-polycyclylpyrimidine compounds encompassed by Formula I is within the scope of the invention, the degree of herbicidal activity, the degree of crop selectivity, and the spectrum of weed control obtained varies depending upon the substituents present.

The compounds of the present invention (Formula I) are best applied in conjunction with one or more other compatible herbicides to obtain control of a wider variety of undesirable vegetation. The compounds of the present invention are generally complementary or even synergistic with a variety of other herbicides. Since the compounds of the invention are generally more potent on grassy weeds than on broadleaf weeds, herbicides that are useful on broadleaf weeds are typically employed in this embodiment. Herbicides that are employed for the control of grassy weeds are also often advantageously employed in conjunction with the compounds of invention. When used in conjunction with other herbicides, the presently claimed compounds can be formulated with the other herbicide or herbicides, tank mixed with the other herbicide or herbicides, or applied sequentially with the other herbicide or herbicides. The herbicides that can be employed in conjunction with the compounds of the present invention include auxin herbicides (such as (2,4-dichlorophenoxy)acetic acid, 2-(2,4-dichlorophenoxy)propionic acid, (4-chloro-2-methylphenoxy)acetic acid, 2-(4-chloro-2-methylphenoxy) propionic acid, ((3,4,6-trichloro-2-pyridinyl)oxy)acetic acid, ((4-amino-3,5-dichloro-6-fluoro-2-pyridinyl)oxy) acetic acid, 4-amino-3,5,6-trichloro-2-pyridinecarboxylic acid, 3,6-dichloro-2-pyridinecarboxylic acid), and 2-methoxy-3,6-dichlorobenzoic acid). Other herbicides that can be used in conjunction with these compounds include substituted triazolopyrimidinesulfonamide herbicides, such as N-2,6-dichlorophenyl-5-ethoxy-7-fluoro|1,2,4|-triazolo |1,5-c|pyrimidine-2-sulfonamide (diclosulam), methyl 3-chloro-2-((5-ethoxy-7-fluoro|1,3,4|triazolo-|1,5-c| pyrimidin-2-yl)sulfonyl)amino)benzoate (cloransulam-methyl), N-2,6-dichloro-3-methylphenyl-5,7-dimethoxy|1, 2,4|triazolo|1,5-a|pyrimidine-2-sulfonamide (metosulam), and N-2,6-difluorophenyl-5-methyl|1,2,4|-triazolo|1,5-a| pyrimidine-2-sulfonamide (flumetsulam); sulfonylurea herbicides, such as chlorimuron, bensulfuron-methyl, pyrazosulfuron-ethyl, and AC-140; aryloxyphenoxypropionate herbicides, such as butyl (R)-2-(4-(4-cyanophenoxy) phenoxy)propionate (cyhalofopbutyl), methyl (R)-2-(4-(5-(trifluoromethyl)-2-pyridinyl)oxy)propionate (fluazifop-P-butyl), ethyl (R)-2-(4-(6-chloro-2-quinoxalinyl)oxy) propionate (quizalofop-P-ethyl), fenoxaprop-P-ethyl, and haloxyfop-R-methyl; as well as propanil, acifluorfen, bentazon, clomazone, fumiclorac, mefenacet, fluometuron, fomesafen, imazaquin, imazethapyr, lactofen, linuron, metribuzin, and many others. The auxin herbicides (2,4-dichlorophenoxy)acetic acid (2,4-D), 2-(2,4-dichlorophenoxy)propionic acid (2,4-DP), (4-chloro-2-methylphenoxy)acetic acid (MCPA), 2-(4-chloro-2-methylphenoxy)propionic acid (MCPP), ((3,4,6-trichloro-2-pyridinyl)oxy)acetic acid (triclopyr), ((4-amino-3,5-dichloro-6-fluoro-2-pyridinyl)oxy)acetic acid (fluroxypyr), 4-amino-3,5,6-trichloro-2-pyridinecarboxylic acid (picloram), 3,6-dichloro-2-pyridinecarboxylic acid (clopyralid), and 2-methoxy-3,6-dichlorobenzoic acid (dicamba) are often preferred. The auxin herbicides (2,4-dichlorophenoxy)acetic acid (2,4-D) and ((3,4,6-trichloro-2-pyridinyl)oxy)acetic acid (triclopyr) are often of special interest. The auxin herbicides are named herein as the acids on which they are based, but they can used in combination with the compounds of the present invention in the form of the acids themselves or in the form of their agriculturally acceptable salts or esters, such as amine or alkali metal salts or alkyl esters, and the naming of the compounds as acids herein expressly includes all of these forms. It is generally preferred to use the compounds of the invention in conjunction with a broadleaf herbicide that is selective to turf, cotton, soybeans, corn, rice, wheat or barley. It is further generally preferred to apply the two or more herbicides at the same time, either as a combination formulation or as a tank mix.

The compounds of the present invention can generally be employed in combination with known herbicide safeners, such as cloquintocet, furilazole, dichlormid, benoxacor, flurazole, mefenpyr-ethyl, dymron, fenclorim, and fluxofenim, to enhance their selectivity. They can additionally be employed to control undesirable vegetation in many crops that have been made tolerant to or resistant to herbicides by genetic manipulation or by mutation and selection. For example, corn, wheat, rice, soybean, sugarbeet, cotton, canola, and other crops that have been made tolerant or resistant to one or more herbicides can be treated.

The term herbicide is used herein to mean an active ingredient which controls or adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation are meant to include germinate seeds, emerging seedlings and established vegetation.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of use, the specific compound of the invention employed, the specific adjuvants and carriers employed, the soil type, and the like, as well as the amount of chemical applied. In the case of applications in the presence of rice, the water status of the paddy soil and/or the flood status at the time of application can also influence the effect observed. These and other factors can be adjusted as is known in the art to promote selective herbicidal action.

Application rates of about 0.01 to about 2 Kg/Ha are generally employed in postemergence operations and rates of about 0.01 to about 5 Kg/Ha are generally employed for preemergence operations. The higher rates designated generally give non-selective control of a broad variety of undesirable vegetation, the lower rates generally are generally employed for selective control in the presence of a crop. Application rates of about 0.010 to about 1 Kg/Ha are generally employed for the control of weeds in paddy rice.

EXAMPLES

The following Examples are presented to illustrate the various aspects of this invention and should not be construed as limitations to the claims. Nuclear Magnetic Resonance (NMR) spectra were obtained using a 300 megaHertz spectrometer. Data on some of the compounds is given in Table 2. Melting points and boiling points are uncorrected.

TABLE 2

| Cpd. No. | Selected Nuclear Magnetic Resonance Data 300 MegaHertz |
|---|---|
| | Tetramethylsilane Internal Standard |
| 4 | 8.70(s, 1H); 7.62(bs, 1H); 7.4–7.2(m, 4H); 4.55(bs, 1H); 4.10(s, 3H); 2.75(q, 2H); 1.2(s, 3H); 0.85(s, 3H) |
| 22 | 8.85(s, 1H); 7.75(s, 1H); 7.15(m, 2H); 6.8(s, 1H); 4.3(s, 1H); 2.8(m, 3H); 2.6(s, 3H); 1.4(s, 3H); 1.2(m, 6H); 0.9(s, 3H) |
| 25 | 8.9(s, 1H); 8.2(d, 1H); 8.05(s, 1H); 7.5(m, 1H); 6.4(s, 1H); 3.4(s, 3H); 2.5–3.0(m, 2H); 1.2(s, 3H); 0.8(s, 3H) |

TABLE 2-continued

Selected Nuclear Magnetic Resonance Data
300 MegaHertz

| Cpd. No. | Tetramethylsilane Internal Standard |
|---|---|
| 26 | 8.8(s, 1H); 7.6(s, 1H); 7.15(m, 1H); 6.8(m, 2H); 3.9(s, 3H); 2.9(d, 1H); 2.7(d, 1H); 2.5(s, 3H); 1.3(s, 3H); 1.0(s, 3H) |
| 33 | 8.8(s, 1H); 7.7(s, 1H); 7.1(s, 1H); 6.9(d, 1H); 6.8(d, 1H); 4.3(s, 1H); 2.8(q, 2H); 2.6(s, 3H); 2.3(s, 3H); 1.3(s, 3H); 0.8(s, 3H) |
| 34 | 8.8(s, 1H); 7.5(s, 1H); 7.0(m, 3H); 4.8(bs, 1H); 2.9(d, 1H); 2.6(d, 1H); 2.4(s, 3H); 2.3(s, 3H); 1.3(s, 3H); 0.9(s, 3H) |
| 36 | 8.6(s, 1H); 7.8(s, 1H); 7.2(m, 4H); 4.5(s, 1H); 3.05(s, 6H); 2.8(m, 2H); 1.2(s, 3H); 0.75(s, 3H) |
| 41 | 8.6(s, 1H); 7.8(s, 1H); 7.2(m, 4H); 4.45(s, 1H); 3.1(s, 6H); 2.8(m, 2H); 1.2(s, 3H); 0.75(s, 3H) |
| 63 | 8.9(s, 1H); 7.7(s, 1H); 7.35(m, 2H); 6.4(s, 1H); 4.0(s, 3H); 3.0(d, 1H); 2.75(d, 1H); 2.5(s, 3H); 1.3(s, 3H); 0.8(s, 3H) |
| 73 | 8.7(s, 1H); 8.6(s, 1H); 7.1–7.8(m, 7H); 5.25(s, 2H); 4.05(s, 3H); 2.40(s, 3H) |
| 79 | 8.7(bd, 1H); 8.0(bd, 1H); 6.8–7.5(m, 7H); 5.2(bs, 2H); 3.7(bd, 3H) |
| 83 | 8.7 & 8.4(2s, 1H); 8.3 & 7.9(2s, 1H); 6.8–7.4(m, 7H); 5.3(m, 2H); 3.4–3.9(2bs, 4H) |
| 85 | 8.6(s, 1H); 8.25(s, 1H); 6.9–7.3(m, 7H); 5.6(bs, 1H); 5.3(bs, 2H); 3.95(s, 3H) |
| 86 | 8.60(bs, 1H); 8.25(bs, 1H); 6.95–7.30(m, 8H); 5.51(bs, 1H); 5.28(bs, 1H); 3.9(bs, 3H); 2.25(s, 3H) |
| 87 | 8.69(s, 1H); 8.41(bs, 1H); 6.95–7.6(m, 7H); 5.27(d, 1H); 5.05(bs, 1H); 4.25(bs, 1H); 3.81(s, 3H); 2.23(bs, 3H) |
| 99 | 8.6(s, 1H); 8.25(bs, 1H); 7.0–7.15(m, 6H); 5.5(bs, 1H); 5.3(bs, 2H); 4.0(s, 3H); 2.6(q, 2H, J=7.7); 1.3(t, 3H, J=7.7) |
| 102 | 8.6(s, 1H); 8.25(s, 1H); 6.9–7.2(m, 7H); 5.5(s, 1H); 5.3(bs, 2H); 4.0(s, 3H) |
| 115 | 8.76(d, 1H); 8.16(d, 1H); 7.49–7.13(m, 8H); 6.16(s, 1H); 3.19–3.16(m, 2H); 2.89–2.87(m, 3H); 2.84(s, 3H) |
| 116 | 9.10(s, 1H); 8.77(s, 1H); 7.50–7.11(m, 8H); 6.31(s, 1H); 3.19–3.08(m, 2H); 3.05(s, 3H); 3.02–2.81(m, 2H) |
| 128 | 8.86(s, 1H); 8.62(s, 1H); 7.26–6.99(m, 3H); 5.85(m, 1H); 3.57(m, 2H); 2.32(s, 3H); 1.43(d, 3H); 1.41(s, 3H); 0.97(d, 3H) |
| 134 | 8.85(s, 1H); 8.51(s, 1H); 7.31–7.10(m, 3H); 6.75(d, 1H); 2.82(m, 2H); 2.33(s, 3H); 1.72(s, 3H); 1.43(d, 3H) |
| 135 | 8.9(s, 1H); 8.4(s, 1H); 7.0–7.4(m, 4H); 3.2(m, 1H); 3.05(s, 1H); 2.8–3.0(m, 2H); 2.5(s, 3H); 2.4(m, 1H) |
| 136 | 8.9(s, 1H); 8.4(s, 1H); 7.0–7.4(m, 4H); 3.2(m, 1H); 3.05(s, 1H); 2.8–3.0(m, 2H); 2.5(s, 3H); 2.4(m, 1H) |
| 137 | 8.8(s, 1H); 7.6(s, 1H); 7.0–7.4(m, 4H); 4.4(s, 1H); 3.0(d, 1H); 2.85(d, 1H); 2.65(s, 3H); 1.6(m, 4H) |
| 138 | 8.9(s, 1H); 8.45(s, 1H); 7.35(m, 2H); 7.2(m, 1H); 6.85(m, 1H); 3.3(m, 1H); 3.0(m, 1H); 2.7(m, 1H); 2.4(s, 3H); 2.3(m, 1H); 1.7(m, 1H); 1.5(m, 2H); 0.9(m, 6H) |
| 139 | 8.8(s, 1H); 7.7(s, 1H); 7.0–7.3(m, 4H); 4.5(s, 1H); 2.9(q, 1H); 2.7(s, 3H); 1.75(m, 3H); 1.4(m, 3H) |
| 140 | 8.8(s, 1H); 7.7(bs, 1H); 7.2(m, 4H); 2.0–3.0(m, 3H); 2.5(s, 3H); 2.2(bs, 1H); 1.7(m, 5H); 1.3(m, 2H) |
| 141 | 8.9(s, 1H); 7.9(s, 1H); 7.8(d, 1H); 7.5(t, 1H); 7.4(d, 1H); 4.7(m, 1H); 3.3(m, 1H); 2.6(m, 4H) |
| 167 | 8.8(s, 1H); 7.9(s, 1H); 7.2(m, 3H); 7.0(d, 1H); 4.6(m, 2H); 4.4(s, 1H); 2.9(m, 2H); 2.8(s, 3H); 2.2(s, 3H); 1.2(s, 3H); 0.8(s, 3H) |
| 169 | 8.9(s, 1H); 7.75(s, 1H); 7.2–7.5(m, 3H); 6.9(d, 1H); 4.5(s, 2H); 4.3(s, 1H); 2.9(q, 2H); 1.3(s, 3H); 0.9(s, 3H) |
| 175 | 8.9(s, 1H); 7.8(s, 1H); 7.2(m, 3H); 6.95(d, 1H); 4.3(s, 1H); 4.2(m, 2H); 2.9(q, 2H); 1.3(s, 3H); 0.9(s, 3H) |
| 176 | 8.8(s, 1H); 7.7(s, 1H); 7.2(m, 3H); 6.9(d, 1H); 6.0(m, 1H); 5.3(m, 1H); 5.2(m, 1H); 4.3(s, 1H); 3.9(m, 2H); 2.9(m, 2H); 1.3(s, 3H); 0.9(s, 3H) |
| 182 | 8.8(s, 1H); 7.75(s, 1H); 7.15(s, 1H); 6.8(d, 1H); 6.5(s, 1H); 6.0(m, 1H); 5.3(m, 2H); 4.3(s, 1H); 4.0(m, 2H); 3.75(s, 3H); 2.8(q, 2H); 1.4(s, 3H); 0.9(s, 3H) |
| 183 | 8.85(s, 1H); 7.75(s, 1H); 7.45(m, 6H); 6.8(m, 1H); 6.5(s, 1H) |
| 184 | 8.9(s, 1H); 8.1(s, 1H); 7.1(m, 1H); 6.8(m, 3H); 6.25(m, 2H); 4.1(s, 1H); 3.9(m, 2H); 1.2(s, 3H); 0.9(s, 3H) |
| 185 | 9.0(s, 1H); 8.15(s, 1H); 7.1(m, 1H); 6.9(m, 1H); 6.3(m, 3H); 4.15(s, 1H); 3.9(q, 2H); 2.75(m, 1H); 1.15(m, 9H); 0.9(m, 3H) |
| 190 | 8.85(s, 1H); 7.5(s, 1H); 7.0(m, 3H); 4.0(s, 2H); 2.4(m, 3H); 1.6(s, 3H); 1.0(m, 3H) |
| 192 | 8.8(s, 1H); 7.85(bs, 1H); 7.1(m, 3H); 4.2(m, 1H); 3.8(m, 2H); 2.7(m, 4H); 1.1(m, 12H) |
| 194 | 9.2(s, 1H); 8.8(s, 1H); 7.0(m, 4H); 5.2(s, 1H); 4.0(2, 2H); 3.6(s, 3H); 1.3(s, 3H); 1.0(s, 1H) |
| 195 | 9.1(s, 1H); 8.75(s, 1H); 7.05(m, 1H); 6.9(m, 1H); 6.7(m, 1H); 5.05(s, 1H); 3.9(q, 2H); 3.55(s, 3H); 2.75(m, 1H); 1.4(s, 3H); 1.2(d, 6H); 0.8(s, 3H) |
| 200 | 9.4(s, 1H); 8.65(s, 1H); 8.0(d, 1H); 7.5(m, 3H); 5.4(s, 1H); 3.65(m, 5H); 1.3(s, 3H); 1.1(s, 1H) |
| 201 | 9.2(s, 1H); 8.65(s, 1H); 8.0(d, 1H); 7.5(m, 3H); 5.4(s, 1H); 3.5(m, 5H); 1.5(s, 3H); 1.1(s, 3H) |
| 205 | 8.85(s, 1H); 7.9(s, 1H); 7.3(s, 1H); 6.5(s, 1H); 4.2(s, 1H); 3.95(q, 2H); 2.7(m, 4H); 1.15(m, 9H); 0.9(s, 3H) |
| 234 | 9.04(s, 1H); 8.25(s, 1H); 7.26–7.0(m, 4H); 5.12(s, 1H); 4.95(d, 1H); 3.73(h, 1H); 2.90(q, 2H); 1.32(d, 6H); 1.32(s, 3H); 0.89(s, 3H) |

1. Preparation of 5-Bromo-4(3H)-pyrimidinone

A solution was prepared by pouring 49 g (grams) of concentrated sulfuric acid into 210 mL (milliliters) of 32 percent peracetic acid in acetic acid. The temperature rose to 48° C. (pre-cooling the peracetic acid is recommended). This solution was allowed to cool and was then added to a pre-cooled (15° C.) solution of 79.5 g (0.50 mol) of 5-bromopyrimidine dissolved in 500 mL of acetone over a 5-min (minute) period with stirring and cooling with an ice/water bath. The temperature rose initially to about 40° C. and then to about 66° C. (reflux temperature). When the temperature began to fall, the ice/water bath was removed and the temperature rose again to reflux and remained there for about 30 min. The mixture was allowed to stir for two hours during which time the temperature returned to ambient and the reaction mixture became a slurry. This slurry was cooled in an ice/water bath for about 45 min and solids were then recovered by filtration to obtain 78.6 g of off-white hemisulfate salt of the title compound. This salt was slurried in 300 mL of water and the slurry was neutralized to pH 7.0 by adding 75 mL of 5N aqueous sodium hydroxide solution with stirring. After standing overnight the solids were collected by filtration, washed with water, and dried under reduced pressure at 75° C. to obtain 41.0 g (46.9 percent of theory) of the title compound as a light tannish solid.

2. Preparation of 5-Bromo-4-chloropyrimidine

A slurry of 50.0 g (0.286 mol) of 5-bromo-4(3H)-pyrimidinone in 250 mL of acetonitrile was prepared and 42.6 g (0.457 mol) of phosphorus oxychloride was added with stirring. The mixture was heated to reflux and after two hours at reflux was allowed to cool. The volatiles were removed by evaporation under reduced pressure. The light brown residue obtained was dissolved in 200 mL of dichloromethane and 200 mL of water was added. This mixture, which was exothermic, was stirred for about 30 min and then the organic phase was recovered by decantation, washed with water, dried over sodium sulfate, and concentrated by evaporation under reduced pressure. The light brown residue amounted to 44.8 g. This was simple distilled and the fraction boiling at 91°–93° C. under 17 millimeters mercury (2.3 kiloPascals) pressure was collected to obtain 41.5 g (47.4 percent of theory) of the title compound as a colorless liquid that turned light yellow on standing.

Elemental Analysis $C_4H_2BrClN_2$ Calc.: %C, 24.8; %H, 1.04; %N, 14.5 Found: %C, 25.1; %H, 1.10; %N, 14.7.

3. Preparation of 5-Bromo-4-methoxypyrimidine

Twenty grams (0.13 mol) of 5-bromo-4-chloropyrimidine were dissolved in 100 mL of methanol and the solution was cooled to 5° C. by means of an ice bath. A solution consisting of 29.5 mL of a 25 percent solution of sodium methoxide in methanol and 20 mL of methanol was added with stirring and cooling. The temperature rose to 37° C. and then began to fall. The mixture was stirred for 4 hours at ambient temperature and was then diluted with 200 mL of water (which caused the formation of a white precipitate) and 200 mL of dichloromethane (which dissolved the precipitate). The phases were separated and the organic phase was washed with 150 mL of water, dried over sodium sulfate, and concentrated by evaporation under reduced pressure to obtain 18.2 g (93.8 percent of theory) of the title compound as a white crystalline solid melting at 73°–75° C.

Elemental Analysis $C_5H_5BrN_2O$ Calc.: %C, 31.8; %H, 2.67; %N, 14.8 Found: %C, 31.8; %H, 2.69; %N, 14.8.

4. Preparation of 5-Bromo-4-methylthiopyrimidine

5-Bromo-4-chloropyrimidine (13.8 g, 0.072 mol) was dissolved in 100 mL of methanol and 6.25 g of solid sodium methanethiolate was added with stirring. The reaction was very exothermic and the temperature rose to reflux. (Cooling and addition of the sodium methanethiolate as a solution in methanol are recommended.) After standing overnight 250 mL of water (which caused the formation of a white precipitate) and 150 mL of dichloromethane (which dissolved the precipitate) were added. The phases were separated and the organic phase was washed with 150 mL of water, dried over sodium sulfate, and concentrated by evaporation under reduced pressure to obtain 12.9 g of off-white solid. This was recrystallized from 20 mL of methanol to obtain 11.0 g of the title compound as a granular white solid melting at 72°–75° C. The sample was found to contain 1.5 percent 5-bromo-4-methoxypyrimidine as a contaminant.

Elemental Analysis $C_5H_5BrN_2S$ Calc.: %C, 29.3; %H, 2.46; %N, 13.7; %S, 15.6 Found: %C, 29.1; %H, 2.72; %N, 13.4; %S, 15.1.

5. Preparation of 6-Methoxy-2,2,5-trimethyl-1-indanone

A solution of 11.7 g of methyl 2-methylpropanoate in 200 mL of dry tetrahydrofuran was prepared and cooled to −15° C. Lithium diisopropylamide solution in a heptane, tetrahydrofuran, and ethylbenzene mixture (85 mL of 2M) was added slowly with stirring so that the temperature remained below −5° C. A solution of 25 g of 4-methoxy-3-methylbenzyl chloride in 150 mL of dry tetrahydrofuran was added with stirring and the mixture was then allowed to warm to ambient over a 2 hours. The reaction mixture was diluted with water and extracted with ethyl acetate. The organic extract was washed with aqueous sodium chloride solution, dried over sodium sulfate, and concentrated by evaporation under reduced pressure to obtain methyl 2,2-dimethyl-3-(4-methoxy-3-methylphenyl)propanoate as a liquid residue. A 2 g portion of the residue was distilled at 85°–90° C. under 1 mm Hg (millimeter of mercury) (133 Pascals) pressure.

The remainder of the residue was dissolved in 50 mL of methanol and 500 mL of water and 24 g of sodium hydroxide were added. The mixture was heated to reflux with stirring overnight. The mixture was then cooled and acidified and the white solid that formed was collected by filtration and dried to obtain 9.6 g of 2,2-dimethyl-3-(4-methoxy-3-methylphenyl)propanoic acid.

Elemental Analysis $C_{13}H_{18}O_3$ Calc.: %C, 70.2; %H, 8.16 Found: %C, 70.3; %H, 8.14.

A mixture of 9.0 g of 2,2-dimethyl-3-(4-methoxy-3-methylphenyl)propanoic acid and 20 mL of oxalyl chloride was prepared and allowed to stir for 2 hours. The volatiles were then removed by evaporation under reduced pressure. The residue was dissolved in 30 mL of carbon disulfide and the solution was added with stirring to a mixture of 7.4 g of aluminum chloride and 30 mL of carbon disulfide. The mixture was allowed to react for 2 hours and was then diluted with 200 mL of 1,2-dichloroethane. Water was added slowly with stirring and, after 2 hours, the mixture was extracted with dichloromethane. The extract was dried over sodium sulfate and concentrated by evaporation under reduced pressure. The residue was distilled to obtain the title compound as a colorless liquid boiling at 90°–95° C. under 1 mm Hg (133 Pascals) pressure.

Elemental Analysis $C_{13}H_{16}O_2$ Calc.: %C, 76.4; %H, 7.90 Found: %C, 76.4; %H, 7.89.

6. Preparation of 6-ethyl-1-indanone

A solution of 33.6 g of triethylphosphonoacetate in 20 mL of tetrahydrofuran was added dropwise with stirring to a slurry of 6.0 g of 60 percent sodium hydride (in mineral oil) in 100 ml of dry tetrahydrofuran. The mixture was allowed to react for 30 min and then a solution of 20.1 g of 4-ethylbenzaldehyde in 100 mL of tetrahydrofuran was added with stirring and the mixture was heated to reflux. After 2 hours the mixture was cooled and water was added. The resulting mixture was extracted with ethyl acetate and the extract was dried over sodium sulfate and concentrated by evaporation under reduced pressure to obtain ethyl 4-ethylcinnamate as the residue.

A solution of 26.8 g of ethyl 4-ethylcinnamate and 10 g of sodium hydroxide in 50 mL of ethanol and 100 mL of water was prepared and allowed to react with stirring for 1 hour. Some of the ethanol was removed by evaporation under reduced pressure and the mixture was acidified with hydrochloric acid. The precipitate that formed was collected by filtration. This precipitate was dissolved in 1N aqueous sodium hydroxide solution and the resulting solution was extracted with ethyl acetate and then acidified with hydrochloric acid. The solids that formed were collected by filtration and dried under reduced pressure to obtain 18.5 g of 4-ethylcinnamic acid melting at 140° C.

A solution containing 18 g of 4-ethylcinnamic acid dissolved in 50 mL of acetic acid was placed in a Parr Shaker bomb flask, 1.0 g of 5% palladium on carbon catalyst was added, and the flask was pressured to 50 psig (pounds per square inch gauge) (4460 kiloPascals) for 2 hours. The catalyst was then removed by filtration and the solution was concentrated by evaporation under reduced pressure. Water was added to the residue and the solid present was collected by filtration and dried under reduced pressure to obtain 3-(4-ethylphenyl)propanoic acid.

A 13.0 g sample of 3-(4-ethylphenyl)propanoic acid was dissolved in 125 g of Eaton's reagent and the mixture was heated at 50° C. with stirring for 3 hours. The resulting mixture was cooled and poured into water. The mixture obtained was extracted with ethyl acetate and the organic extract was dried over sodium sulfate and concentrated by evaporation under reduced pressure. The residue was distilled and the 7.8 g colorless liquid fraction boiling at 95°–100° C. under 0.5 mm Hg (66 Pascals) pressure was collected to obtain 6-ethyl-1-indanone.

7. Preparation of 6-Fluoro-1-indanone 3-(4-Fluorophenyl)propanoic acid was prepared by procedures analogous to those of Example 6 from 4-fluorobenzaldehyde. Oxalyl chloride (25 mL, 36.4 g, 0.287 mol) was added to 20.0 g (0.119 mol) of this acid. The resulting slurry was heated at reflux with stirring for 1 hour. The solution obtained was cooled and the volatile components were removed by evaporation under reduced pressure. Dichloroethane was added and removed by evaporation under reduced pressure. The residue was dissolved in 75 mL of dichloroethane and the solution was added with stirring to a slurry of 16 g of anhydrous aluminum chloride in 75 mL of dichloroethane. The mixture evolved hydrogen chloride and exothermed raising the temperature to about 40° C. It was then heated at reflux with stirring for about 45 min after which it was allowed to cool overnight. Concentrated aqueous hydrochloric acid (100 mL) was then added with stirring, which resulted in a large exotherm. The resulting mixture was diluted with 100 mL of dichloromethane and 250 mL of water and the organic phase was recovered by means of a separatory funnel, washed with 300 mL of 0.5N aqueous sodium hydroxide, dried over sodium sulfate, and concentrated by evaporation under reduced pressure. The residue, which amounted to 16.3 g of cream colored solid melting at 57°–60° C., was the title compound.

4,6-Dimethyl-1-indanone, a white crystalline solid melting at 118°–120° C., was prepared similarly.

8. Preparation of 6-Ethyl-2,2-dimethyl-1-indanone

A mixture of 6.8 g of 6-ethylindanone, 18 g of methyl iodide, 19 g of potassium hydroxide, 0.1 g of 18-crown-6 polyether catalyst, and 250 mL of toluene was heated at 50° C. with stirring overnight. The resulting mixture was allowed to cool and was poured into water. The mixture obtained was extracted with ethyl acetate and the organic extract was dried over sodium sulfate and concentrated by evaporation under reduced pressure. The residue was distilled and the colorless liquid fraction boiling at 86°–90° C. under 1.0 mm Hg (133 Pascals) pressure was collected as the title compound.

Elemental Analysis $C_{13}H_{16}O$ Calc.: %C, 82.9; %H, 8.51 Found: %C, 82.1; %H, 8.59.

6-Fluoro-2,2-dimethyl-1-indanone, a white crystalline solid melting at 64.5°–66.5° C. and 2,2-dimethyl-1-tetralone, a colorless liquid boiling at 88°–89° C. under 0.75 mm Hg (100 Pascals) pressure were prepared similarly.

9. Preparation of 2,2,3-Trimethyl-1-indanone

A solution of 30.0 g (0.205 mol) of 3-methyl-1-indanone in 150 mL of dry dimethyl sulfoxide was prepared and 31.9 mL (72.8 g, 0.513 mol) of methyl iodide was added. The solution was cooled to 7° C. and 31.7 g of 87 percent powdered potassium hydroxide was added over a 40-min period with stirring and cooling to keep the temperature below 18° C. The mixture was allowed to react for 1 hour cold and then allowed to warm. Another 10 mL of methyl iodide and 4.5 g of powdered potassium hydroxide were added with stirring at ambient temperature. The mixture exothermed to 47° C. The reaction appeared to be complete, but the mixture was (unnecessarily) allowed to stir for 1 week. It was then diluted with 300 mL of water and 300 mL of hexane. The organic phase was recovered, washed with water (2×150 mL), dried over sodium sulfate, and concentrated by evaporation under reduced pressure. The 34.8 g of yellow liquid residue was distilled in a short path still and the colorless center cut boiling at 74° C. under 0.75 mm Hg (100 Pascals) pressure was collected and was the title compound.

Elemental Analysis $C_{12}H_{14}O$ Calc.: %C, 82.7; %H, 8.10 Found: %C, 82.5; %H, 8.30.

2,2,4,6-Tetramethyl-1-indanone, a colorless oil recovered by distillation at 98° C. under 0.8 mm Hg (106 Pascals) pressure, was prepared similarly.

10. Preparation of 2,2-Dimethyl-3-coumaranone

A solution of 24.0 g (0.179 mol) of 3-coumaranone in 300 mL of N,N-dimethylformamide was prepared and 50.1 mL (114 g, 0.805 mol) of methyl iodide and 148.4 g of powdered potassium carbonate were added. The mixture was stirred for 24 hours at ambient temperature and was then diluted with about 500 mL of water and 300 mL of diethyl ether. The ethereal phase was recovered and washed with water (3×300 mL), dried over sodium sulfate, and concentrated by evaporation under reduced pressure. The yellow-orange liquid residue was distilled at 1.4 mm Hg (0.19 kiloPascals) pressure using a Bantamware® Vigreaux column to obtain (at 75°–85° C.) 14.9 g of a colorless liquid consisting of at least 3 components, about ⅓ of which was the desired product. This mixture was flash chromatographed on 300 g of silica gel eluting first with 8.3 liters of hexane (in 30 fractions) and then with 2.4 liters of hexane containing 5 percent ethyl acetate (in 300 mL fractions). The first two of the latter fractions were combined and concentrated by evaporation under reduced pressure to obtain 5.0 g of the title compound as a colorless oil.

11. Preparation of 6-(1-Methylethyl)-4-chromanone

A solution of 15.0 g of 4-(1-methylethyl)anisole and 17.0 g of 3-chloro-2,2-dimethylpropionyl chloride in 200 mL of dichloromethane was prepared and 15 g of aluminum chloride was added slowly and with stirring. The mixture was allowed to stir overnight and then 20 mL of concentrated aqueous hydrochloric acid was added. The resulting mixture was diluted with 200 mL of dichloromethane and the organic phase was recovered. This was washed with saturated aqueous sodium chloride and then with 2N aqueous sodium hydroxide, was dried over sodium sulfate, and was concentrated by evaporation under reduced pressure to obtain 18.5 g of 2-(3-chloro-2,2-dimethylpropionyl)-4-(1-methylethyl) anisole. An 18.0 g portion of this was dissolved in 100 mL of dichloromethane and treated with 140 mL of 1M boron tribromide in dichloromethane at ambient temperature with stirring. After 3 hours the mixture was poured into 500 mL of water and the organic phase was recovered, dried over sodium sulfate, and concentrated by evaporation under reduced pressure. The resulting oil was distilled at 85°–88° C. under 0.5 mm (70 Pascals) pressure to obtain 12.5 g of 2-(3-chloro-2,2-dimethylpropionyl)-4-(1-methylethyl) phenol. This was dissolved in 20 mL of dry tetrahydrofuran and the resulting solution was added slowly with stirring to a slurry of 2.3 g of 60 percent sodium hydride (in mineral oil) in 50 mL of dry tetrahydrofuran. The mixture obtained was heated to reflux with stirring for 1 hour. It was then cooled and diluted with water. The resulting mixture was extracted with ethyl acetate and the extract mixture was dried over sodium sulfate and concentrated by evaporation under reduced pressure. The resulting oil was chromatographed on silica gel eluting with a 9:1 mixture of hexane and ethyl acetate to obtain 7.6 g of the title compound.

12. Preparation of Dibenzo[d,g][1,3]dioxocin-12-one

A mixture of 21.4 g (100 mmol) of 2,2'-dihydroxybenzophenone, 150 mL of anhydrous dimethyl sulfoxide, 20.9 g (120 mmol) of dibromomethane, and 30.4 g of dry powdered potassium carbonate was prepared and was heated by means of an oil bath set at 75° C. and stirred. The temperature rose to 87° C. over a 15-min period and then dropped. After another 1.5 hours, the mixture was cooled, diluted with 250 mL of water and 100 mL of 1N aqueous sodium hydroxide. This mixture was extracted with ether (2×100 mL) and the combined ether extracts were washed with water (2×100 mL), dried over sodium sulfate, and concentrated by evaporation under reduced pressure to obtain 19.4 g of a light yellow, mostly solid residue. The residue was recrystallized from 50 mL of a 1:1 benzene/hexane mixture and washed with hexane to obtain, after drying at 75° C. under reduced pressure, 12.4 g (71 percent of theory) of the title compound as a white solid melting at 92.5°–94° C.

3-Methyldibenzo[d,g][1,3]dioxocin-12-one was prepared similarly.

13. Preparation of 5-(5-Hydroxydibenzosuberan-5-yl)-4-methoxypyrimidine (Cpd. 104)

A solution containing 1.89 g (10.0 mmol (millimole)) of 5-bromo-4-methoxypyrimidine, 2.08 g (10.0 mmol) of dibenzosuberone, and 25 mL of Sure Seal™ tetrahydrofuran was prepared and cooled to −70° C. by means of a dry ice/acetone bath. A 1.6 molar solution of n-butyl lithium in hexane (6.9 mL, 11.0 mmol) was added with stirring and cooling by means of a syringe at a rate that kept the temperature below −65° C. When the addition was complete, the mixture was stirred another 5 min and was then allowed to warm to −20° C. Ten mL of water was added and the mixture was then allowed to warm to ambient. Analysis by gas-liquid chromatography indicated that a mixture of 5-bromo-4-methoxypyrimidine and the title compound was present. Ether and water were added and the phases were separated. The aqueous phase was extracted with more ether and the ether phases were combined, dried over sodium sulfate, and concentrated by evaporation under reduced pressure. The resulting residue, which partially crystallized, was dissolved in dichloromethane and the solution was chromatographed on flash grade silica gel eluting first with dichloromethane to remove less polar impurities and then with then with a 97:3 mixture of dichloromethane and acetone to obtain the title compound. The 1.1 g of crude product obtained was recrystallized from about 5 mL of ethanol to remove both some insoluble and some soluble impurities and obtain, after drying by heating under reduced pressure, 0.90 g (28 percent of theory) of the title compound as white crystals melting at 195°–196.5° C.

Elemental Analysis $C_{20}H_{18}N_2O_2$ Calc.: %C, 75.5; %H, 5.70; %N, 8.80 Found: %C, 75.4; %H, 5.82; %N, 8.98.

This method was used to prepare a variety of 5-(1-hydroxyindan-1-yl)-4-alkoxypyrimidine, 5-(1-hydroxytetralin-1-yl)-4-alkoxypyrimidine, 5-(3-hydroxycoumaran-3-yl)-4-alkoxypyrimidine, 5-(4-hydroxychroman-4-yl)-4-alkoxypyrimidine, and 5-(12-hydroxydibenzo[d,g][1,3]-dioxocin-12-yl)-4-alkoxypyrimidine compounds.

14. Preparation of 5-(Dibenzosuberan-5-yl)-4-methoxypyrimidine (Cpd. 103)

A solution of 1.15 g (3.61 mmol) of 5-(5-hydroxydibenzosuberan-5-yl)-4-methoxypyrimidine in 25 mL of dichloromethane was prepared and cooled to 3° C. by means of an ice bath. To this was added with stirring and cooling 1.15 mL (7.2 mmol) of triethylsilane and then 0.90 mL (7.2 mmol) of boron trifluoride etherate. The mixture was held at about 3° C. for 30 min and was then allowed to warm to ambient temperature and react for 2 hours. Ten mL of saturated aqueous sodium bicarbonate was added and the resulting slurry was stirred overnight and then diluted with 50 mL of dichloromethane and 50 mL of saturated aqueous sodium bicarbonate. The phases were separated and the organic phase was washed with 50 mL of water, dried over sodium sulfate, and concentrated by evaporation under reduced pressure. The 1.3 g of residue obtained, which partially crystallized, was dissolved in dichloromethane and chromatographed on dry, flash grade silica gel, eluting with dichloromethane. A total of 0.81 g (74 percent of theory) of the title compound was obtained after drying. The product was a white crystalline solid melting at 123°–126° C.

Elemental Analysis $C_{20}H_{18}N_2O$ Calc.: %C, 79.4; %H, 6.00; %N, 9.27 Found: %C, 79.3; %H, 5.97; %N, 9.34.

This method was used to prepare a variety of 5-(indan-1-yl)-4-alkoxypyrimidine, 5-(tetralin-1-yl)-4-alkoxypyrimidine, 5-(coumaran-3-yl)-4-alkoxypyrimidine, 5-(chroman-4-yl)-4-alkoxypyrimidine, and 5-(dibenzo[d,g][1,3]dioxocin-12-yl)-4-alkoxypyrimidine compounds.

15. Preparation of 5-(3-Fluorodibenzo[d,g][1,3]dioxocin-12-yl)-4-methoxypyrimidine (Cpd. 100)

A solution of 1.2 g of 5-(3,12-difluorodibenzo-[d,g][1,3]dioxocin-12-yl)-4-methoxypyrimidine in 20 mL of tetrahydrofuran and 20 mL of dioxane was prepared and 3.5 mL of 0.5M lithium aluminum hydride in dimethoxyethane (2 equivalents) was added with stirring at ambient temperature. The mixture was allowed to stir overnight and then another 4 equivalents of lithium aluminum hydride were added in two shots separated by 2 hours. The resulting mixture was poured into 1N aqueous hydrochloric acid and the mixture obtained was extracted with dichloromethane. The extract mixture was dried over sodium sulfate and concentrated by evaporation under reduced pressure to obtain a crude product. This was chromatographed on silica gel eluting with a 50:50 by volume mixture of hexane and ethyl acetate to obtain 0.33 g of the title compound melting at 144°–148° C.

Elemental Analysis $C_{18}H_{15}FN_2O_3$ Calc.: %C, 67.5; %H, 4.47; %N, 8.28 Found: %C, 67.5; %H, 4.76; %N, 8.28.

16. Preparation of 4-Methylthio-5-(1-hydroxy-2,2-dimethylindan-1-yl)pyrimidine (Cpd. 2)

A solution of 4.90 g (23.9 mmol) of 5-bromo-4-methylthiopyrimidine in 75 mL of dry tetrahydrofuran was prepared and cooled by means of a liquid nitrogen/methanol bath to −92° C. Sixteen mL of 1.6M n-butyl lithium (25.6 mmol) was added to this solution by means of a syringe pump with stirring and cooling. The solid dissolved and the light brown solution obtained was stirred at −91° C. to −95° C. for 10 min. A solution of 3.83 g (23.9 mmol) of 2,2-dimethyl-1-indanone in 10 mL of dry tetrahydrofuran was prepared and added to the reaction mixture over a 15-min period by means of a syringe pump with stirring and cooling. The mixture was allowed to warm and stir overnight at which time the temperature was 11° C. Fifty mL of water and 150 mL of diethyl ether were added. The organic phase was recovered by means of a separatory funnel, washed with 100 mL of water, dried over sodium sulfate, and concentrated by evaporation under reduced pressure to obtain 10.8 g of a reddish oily solid. This solid was diluted with about 40 mL of hexane and the orange solids in the resulting mixture were collected by filtration, washed with hexane, and dried under reduced pressure at about 64° C. (3.61 g). This solid was dissolved in a small amount of dichloromethane and flash chromatographed on silica gel eluting with dichloromethane and collecting 16 150 mL fractions.

Fractions 4–16 were combined and concentrated by evaporation under reduced pressure and dried under reduced pressure at about 65° C. to obtain 2.2 g of the title compound as a white crystalline solid melting at 189°–190.5° C. Another 1.26 g of product as an orange solid was obtained by flushing the column with 200 mL of acetone. This was further purified by recrystallization from ethanol and dried.

Elemental Analysis $C_{16}H_{18}N_2OS$ Calc.: %C, 67.1; %H, 6.33; %N, 9.78; %S, 11.2 Found: %C, 67.0; %H, 6.53; %N, 9.97; %S, 9.97.

This method was used to prepare a variety of
5-(1-hydroxyindan-1-yl)-4-alkylthiopyrimidine,
5-(1-hydroxytetralin-1-yl)-4-alkylthiopyrimidine,
5-(3-hydroxycoumaran-3-yl)-4-alkylthiopyrimidine,
5-(4-hydroxychroman-4-yl)-4-alkylthiopyrimidine,
5-(4-hydroxythiochroman-4-yl)-4-alkylthiopyrimidine, and
5-(12-hydroxydibenzo|d,g||1,3|dioxocin-12-yl)-4-alkylthiopyrimidine compounds.

17. Preparation of 4-Methylthio-5-(2,2-dimethylindan-1-yl)pyrimidine (Cpd. 1)

A solution of 2.1 g (7.3 mmol) of 4-methylthio-5-(1-hydroxy-2,2-dimethylindan-1-yl)pyrimidine in 70 mL of dichloromethane was prepared and 2.34 mL (1.7 g, 14.7 mmol) of triethylsilane and then 1.80 mL (2.08 g, 14.7 mmol) of boron trifluoride etherate were added with stirring. The solid dissolved and the resulting yellow solution was stirred for 24 hours at ambient temperature. The mixture was then diluted with 50 mL of saturated aqueous sodium bicarbonate and stirred for several hours. The organic phase was recovered, washed with 75 mL of water, dried over sodium sulfate, and concentrated by evaporation under reduced pressure. The 2.06 g of clear oil residue obtained was dissolved in a minimal amount of a 1:1 mixture of dichloromethane and hexane and flash chromatographed on silica gel eluting with more of the same solvent mixture and collecting 18 150 mL fractions. Fractions 2–15 were combined and concentrated by evaporation under reduced pressure. The residue was 1.33 g (75 percent of theory) of the title compound as a white granular crystalline solid melting at 92°–95° C.

Elemental Analysis $C_{16}H_{18}N_2S$ Calc.: %C, 71.1; %H, 6.71; %N, 10.4; %S, 11.9 Found: %C, 71.0; %H, 6.68; %N, 10.6; %S, 11.4.

This method was used to prepare a variety of 5-(indan-1-yl)-4-alkylthiopyrimidine, 5-(tetralin-1-yl)-4-alkylthiopyrimidine, 5-(coumaran-3-yl)-4-alkylthiopyrimidine, 5-(chroman-4-yl)-4-alkylthiopyrimidine, 5-(thiochroman-4-yl)-4-alkylthiopyrimidine, and 5-(dibenzo[d,g][1,3]dioxocin-12-yl)-4-alkylthiopyrimidine compounds.

18. Preparation of 4-Methanesulfonyl-5-(2,2-dimethylindan-1-yl)pyrimidine (Cpd. 66)

A mixture of 10.8 g of 57–86 percent of meta-chloroperbenzoic acid in 150 mL of chloroform was added with stirring to a solution of 5.4 g (0.020 mol) of 4-methylthio-5-(2,2-dimethylindan-1-yl)pyrimidine in 60 mL of chloroform over a 30-min period. There was a slight exotherm. After stirring for 1 hr at ambient temperature, another 150 mL of chloroform was added and the resulting solution was extracted sequentially once with 200 mL of saturated aqueous sodium bisulfite, twice with 200 mL of saturated aqueous sodium bicarbonate, and once with 200 mL of water. The organic phase was then dried over sodium sulfate and concentrated by evaporation under reduced pressure at 50° C. to obtain the title compound as a white crystalline solid melting at 62°–63° C.

Elemental Analysis $C_{16}H_{18}N_2O_2S$ Calc.: %C, 63.6; %H, 6.00; %N, 9.26; %S, 10.6 Found: %C, 63.4; %H, 6.10; %N, 9.38; %S, 10.4.

19. Preparation of 4-Methanesulfonyl-5-(2,2-dimethyltetralin-1-yl)pyrimidine (Cpd. 215) and 4-Methanesulfonyl-5-(2,2-dimethyltetralin-1-yl)pyrimidine-N-oxide (Cpd. 230)

A mixture of 17.5 g of 57–86 percent meta-chloroperbenzoic acid in 300 mL of chloroform was added with stirring to a solution of 6.0 g (21 mmol) of 4-methylthio-5-(2,2-dimethyltetralin-1-yl)pyrimidine in 100 mL of chloroform and the resulting mixture was allowed to react at ambient temperature for 16 hours. The mixture was washed with dilute aqueous sodium bisulfite and then with dilute aqueous sodium bicarbonate, was dried over magnesium sulfate, filtered, and concentrated by evaporation under reduced pressure. The residue was chromatographed on silica gel to obtain as the first eluted compound, 4.0 g (60 percent of theory) of a colorless solid which was the first named title compound melting at 118.5°–120° C.

Elemental Analysis $C_{17}H_{20}N_2O_2S$ Calc.: %C, 64.5; %H, 6.37; %N, 8.85; %S, 10.1 Found: %C, 64.6; %H, 6.39; %N, 8.93; %S, 10.1.

The second compound eluted, which was the second named title compound, was 1.35 g (19 percent of theory) of a colorless solid melting at 154°–155° C.

Elemental Analysis $C_{17}H_{20}N_2O_3S$ Calc.: %C, 61.4; %H, 6.06; %N, 8.43; %S, 9.64 Found: %C, 61.4; %H, 6.06; %N, 8.39; %S, 9.60.

$^1$H NMR (CDCl$_3$): 8.6(s, 1H); 7.7(s, 1H); 6.9–7.2(m, 4H); 5.0(s, 1H); 3.4(s, 1H); 2.92(d, 1H, j=4.5); 2.89(d, 1H, j=4.8); 1.7(m, 1H); 1.5(m, 1H); 1.1(s, 3H); 0.9(s, 3H).

When the oxidation of Example 18 was carried out analogously, a second compound, which was 4-methanesulfonyl-5-(2,2-dimethylindan-1-yl)pyrimidine-N-oxide, was obtained. The compound was a colorless solid melting at 164°–165° C.

Elemental Analysis $C_{16}H_{18}N_2O_3S$ Calc.: %C, 60.4; %H, 5.70; %N, 8.80; %S, 10.1 Found: %C, 60.1; %H, 5.83; %N, 8.79; %S, 9.63.

$^1$H NMR (CDCl$_3$): 8.7(s, 1H); 7.7(s, 1H); 7.1–7.35(m, 4H); 5.1(s, 1H); 3.46(s, 1H); 3.0(d, 1H, j=16.5); 2.84(d, 1H, j=16.3); 1.3(m, 1H); 1.04(s, 3H).

20. Preparation of 5-(3,3-Dimethyl-1,1-dioxo-4-thiochromanyl)-4-methanesulfonylpyrimidine (Cpd. 300)

Meta-chloroperbenzoic acid (8 g of 50–70 percent) was added with stirring to a solution of 1.1 g of 5-(3,3-dimethylthiochroman-4-yl)-4-methylthiopyrimidine in dichloromethane. After 3 hours, the mixture was filtered and the filtrate was washed with aqueous sodium bicarbonate, aqueous sodium bisulfite, and concentrated aqueous sodium chloride. The mixture was then concentrated by evaporation under reduced pressure and the oil that was obtained was triturated with hexane. A first crop amounting to 0.8 g and melting at 202°–208° C. and a second crop amounting to 0.4 g of the title compound were obtained.

Elemental Analysis $C_{16}H_{18}N_2S_2O_4$ Calc.: %C, 52.4; %H, 4.95; %N, 7.04; %S, 17.5 Found: %C, 50.7; %H, 5.02; %N, 6.85; %S, 16.5.

21. Preparation of 4-Benzylthio-5-(2,2-dimethylindan-1-yl)pyrimidine (Cpd. 159)

A solution of 6.7 g of impure 5-(2,2-dimethyl-1-indanyl)-4-methanesulfonylpyrimidine (approximately 6.1 g (0.20 mol) in 50 mL of dry tetrahydrofuran was prepared and to this was added with stirring 2.5 mL (2.6 g, 0.21 mol) of benzyl mercaptan and then, in several small portions, 0.84 g of 60 percent sodium hydride in mineral oil (0.21 mol). Hydrogen was evolved and the mixture became cloudy. After about 4 hr the mixture was diluted with 200 mL of hexane and 150 mL of 2N aqueous sodium hydroxide. The phases were separated and the organic phase was washed with water, dried over sodium sulfate, and concentrated by evaporation under reduced pressure to obtain 7.6 g of crude product. This was dissolved in hexane and flash chromatographed on silica gel eluting first with hexane (10×200 mL) and then with a 25:75 by volume mixture of dichloromethane and hexane (14×200 mL) and then with dichloromethane 12×200 mL). There was desired product in fractions 12–36 and these fractions were combined and the resulting mixture was concentrated by evaporation under reduced pressure at 50° C. to obtain 6.3 g of the title compound as a white solid melting at 76°–79° C.

Elemental Analysis $C_{22}H_{22}N_2S$ Calc.: %C, 76.3; %H, 6.40; %N, 8.09; %S, 9.25 Found: %C, 75.2; %H, 6.27; %N, 8.00; %S, 8.99.

A number of related 5-(2,2-dimethylindan-1-yl)-4-(benzylthio, alkylthio, alkenylthio, phenylthio, alkoxy, alkenoxy, and alkylamino)pyrimidine compounds were prepared similarly.

22. Preparation of 5-(2,2-Dimethylindan-1-yl)-4-cyanopyrimidine) (Cpd. 210)

A solution of 16 g (245 mmol) of potassium cyanide and 21.6 g (71 mmol) of 5-(2,2-dimethylindan-1-yl)-4-methanesulfonylpyrimidine in 180 mL of dimethyl sulfoxide was heated to 40° C. with stirring for 15 min. The resulting mixture was cooled and poured into water. The mixture obtained was extracted with ether and the ethereal extract was dried over magnesium sulfate, filtered, and concentrated by evaporation under reduced pressure. The residue obtained was purified by column chromatography on silica gel to obtain 12.5 g (63 percent of theory) of the title compound as a light tan solid melting at 55°–56° C.

Elemental Analysis $C_{16}H_{15}N_3$ Calc.: %C, 77.1; %H, 6.06; %N, 16.9 Found: %C, 77.0; %H, 5.91; %N, 16.8.

$^1$H NMR (CDCl$_3$): 9.2(s, 1H); 8.4(s, 1H); 7.2–7.4(m, 3H); 6.9(d, 1H, j=7.3); 4.5(s, 1H); 2.9(d, 1H, j=15.8); 2.8(d, 1H, j=15.8); 1.4(s, 3H); 0.8(s, 3H).

23. Preparation of 5-(2,2-Dimethylindan-1-yl)-4-methoxycarbonyl-5-pyrimidine (Cpd. 212)

A solution of 5.0 g (20 mmol) of 5-(2,2-dimethylindan-1-yl)-4-cyanopyrimidine and 2 g (6.2 mmol) of mercuric acetate in 100 mL of a mixture of trifluoroacetic acid and water was heated at reflux for 50 hr. The volatiles were removed by evaporation under reduced pressure and the residue obtained was dissolved in 500 mL of methanol. A solution of 200 mL of 2M trimethylsilyldiazomethane in hexane was added to the resulting solution with stirring. After a short reaction period, the volatiles were removed by evaporation under reduced pressure and the residue obtained was purified by column chromatography on silica to obtain 1.1 g of the title compound as a colorless solid melting at 43.5°–45° C.

Elemental Analysis $C_{17}H_{18}N_2O_2$ Calc.: %C, 72.3; %H, 6.43; %N, 9.92 Found: %C, 72.4; %H, 6.39; %N, 9.79.

$^1$H NMR (CDCl$_3$): 9.1(s, 1H); 8.3(s, 1H); 7.15–7.35(m, 3H); 7.1(d, 1H, j=7.3); 4.8(s, 1H); 4.1(s, 3H); 2.9(d, 1H, j=16); 2.85(d, 1H,j=16); 1.3(s, 3H); 0.8(s, 1H).

24. Preparation of 4-Mercapto-5-(2,2-dimethylindan-1-yl) pyrimidine (Cpd. 180)

A mixture of 1.0 g (0.004 mol) of 4-methylthio-5-(2,2-dimethylindan-1-yl)pyrimidine and 1.4 g of sodium methanethiolate in 10 mL of N,N-dimethylformamide was prepared and heated to reflux with stirring for 1.5 hr. The mixture was cooled and was then added to 20 mL of 2N aqueous hydrochloric acid with stirring. The mixture obtained was extracted with 30 mL of ethyl acetate and the resulting organic solution was washed with water and then saturated aqueous sodium chloride. It was then dried over sodium sulfate and concentrated by evaporation under reduced pressure to obtain an oil. The oil was low pressure liquid chromatographed on silica gel eluting first with hexane to remove impurities and then with a 50:50 by volume mixture of ethyl acetate and hexane. The fractions containing the major component of the mixture were concentrated by evaporation under reduced pressure and the oil that was obtain solidified. The resulting 0.66 g (70 percent of theory) solids was the title compound melting at 184°–186° C.

Elemental Analysis $C_{15}H_{16}N_2S$ Calc.: %C, 70.3; %H, 6.28; %N, 10.9 Found: %C, 70.0; %H, 6.20; %N, 10.8.

25. Preparation of 4-(3-Fluorobenzylthio)-5-(2,2-dimethylindan-1-yl)pyrimidine (Cpd. 148)

A mixture of 0.57 g (0.002 mol) of 4-mercapto-5-(2,2-dimethylindan-1-yl)pyrimidine, 0.57 g (0.003 mol) of 3-fluorobenzyl bromide, and 0.41 g (0.003 mol) in 10 mL of acetonitrile was stirred at ambient temperature for 2 hr. Saturated aqueous ammonium carbonate (5 mL) was added and the mixture obtained was extracted with ethyl acetate. The extract solution was washed with water and with concentrated aqueous sodium chloride and then was dried over sodium sulfate and concentrated by evaporation under reduced pressure. The resulting oil was low pressure liquid chromatographed on silica gel eluting first with hexane and then with a 20:80 by volume mixture of ethyl acetate and hexane. The eluent fractions containing the major component were concentrated by evaporation under reduced pressure to obtain the title compound as a white solid melting at 60°–62° C.

Elemental Analysis $C_{22}H_{21}FN_2S$ Calc.: %C, 72.5; %H, 5.80; %N, 7.68 Found: %C, 72.6; %H, 5.79; %N, 7.63.

A number of (2,2-dimethylindan-1-yl)-4-(alkylthio, alkenylthio, benzylthio, and pyridinylmethylthio)pyrimidine compounds were prepared similarly alkylating with appropriate chloro or bromo compounds. 4-Trifluoromethylthio compounds were also prepared similarly, alkylating with iodotrifluoromethane.

26. Preparation of 5-(8-Bromo-3,3-dimethyl-6-(1-methylethylchroman-4-yl)-4-methylthiopyrimidine (Cpd. 205)

Bromine (0.2 mL) was added to a solution of 0.8 g of 5-(3,3-dimethyl-6-(1-methylethyl) chroman-4-yl)-4-methylthiopyrimidine in 20 mL of dichloromethane with stirring and the mixture was allowed to react overnight. It was then washed with 10 percent aqueous sodium bisulfite, dried over sodium sulfate, and concentrated by evaporation under reduced pressure. The residue was chromatographed on silica gel eluting with a 9:1 mixture of hexane and ethyl acetate to obtain 0.6 g of the title compound.

27. Preparation of 5-(12-Fluorodibenzo|d,g||1,3|dioxocin-12-yl)-4-methoxypyrimidine (Cpd. 78)

A mixture of 0.8 g of 5-(12-hydroxydibenzo|d,g||1,3| dioxocin-12-yl)-4-methoxypyrimidine, 1 mL of DAST (diethylaminosulfur trifluoride) and 30 mL of dichloromethane was prepared and allowed to stir at ambient temperature overnight. The mixture was then washed with water, dried over sodium sulfate, and concentrated by evaporation under reduced pressure. The residue was recrystallized from a mixture of dichloromethane and hexane to obtain 0.25 g of the title compound as a white solid.

5-(3,12-Difluorodibenzo|d,g||1,3|dioxocin-12-yl)-4-methoxypyrimidine (Cpd. 79) was prepared similarly.

28. Preparation of 5-(2,2-Dimethyl-6-nitroindan-1-yl)-4-methylthiopyrimidine (Cpd. 62)

To a solution of 30 g (0.11 mol) of 5-(2,2-dimethylindan-1-yl)-4-methylthiopyrimidine in 500 mL of dichloromethane was added dropwise 100 mL of 90 percent nitric acid. After 1 hr the reaction mixture was poured onto a large volume of ice. The mixture was slowly neutralized with solid potassium carbonate and was then extracted with ether. The organic phase was recovered, dried over magnesium sulfate, filtered, and concentrated by evaporation under reduced pressure to obtain 36 g of a tan solid. This was recrystallized from 400 mL of ethyl acetate to obtain 12 g of the title compound as a white solid melting at 167°–168° C.

Elemental Analysis $C_{16}H_{17}N_3O_2S$ Calc.: %C, 60.9; %H, 5.93; %N, 13.3; %S, 10.2 Found: %C, 61.1; %H, 5.73; %N, 13.3; %S, 10.1.

$^1$H NMR (CDCl$_3$): 8.9(s, 1H); 8.16(d, d.1H, j=2.2, 8.1); 7.8(s, 1H); 7.7(s, 1H); 7.45(d, 1H, j=8.1); 4.4(s, 1H); 3.0(d, 1H, j=16.9); 2.95(d,1H, j=16.9); 2.7(s, 3H); 1.4(s, 3H); 0.95(s, 3H).

29. Preparation of 5-(6-Amino-2,2-dimethylindan-1-yl)-4-methylthiopyrimidine (Cpd. 61)

To a slurry of 15.2 g of 5-(2,2-dimethyl-6-nitroindan-1-yl))-4-methylthiopyrimidine in 200 mL of ethanol and 150 mL of ethyl acetate was added 2 g of Lindlar's catalyst and the mixture was shaken under 50 psig (4460 kiloPascals) pressure of hydrogen at 45° C. for 16 hr. The resulting mixture was cooled and filtered through powdered cellulose. The filtrate was concentrated by evaporation under reduced pressure and the residue was dissolved in dichloromethane. The resulting solution was dried over magnesium sulfate, filtered, and concentrated by evaporation under reduced pressure to obtain the title compound as a colorless oil that crystallized upon standing to a white solid melting at 114°–115° C.

Elemental Analysis $C_{16}H_{19}N_3S$ Calc.: %C, 67.6; %H, 6.38; %N, 14.8; %S, 11.3 Found: %C, 67.6; %H, 6.58; %N, 14.7; %S, 11.3.

$^1$H NMR (CDCl$_3$): 8.8(s, 1H); 7.7(s, 1H); 7.0(d, 1H, j=8); 6.6(d, d, 1H, j=1.8, 8.0); 6.3(d, 1H, j=1.6); 4.2(s, 1H); 3.5(br, 2H); 2.8(d, 1H, j=15.2); 2.7(d, 1H, j=15.2); 2.6(s, 3H); 1.3(s, 3H); 0.9(s, 3H).

30. Preparation of 5-(6-Cyano-2,2-dimethylindan-1-yl)-4-methylthiopyrimidine (Cpd. 209)

To a mixture of 1.0 g (3.5 mmol) of 5-(6-amino-2,2-dimethylindan-1-yl)-4-methylthiopyrimidine in 25 mL of dry acetonitrile was added with stirring 1.0 g (7.0 mmol) of nitrosonium tetrafluoroborate. The brown solution was allowed to react for 10 min and was then poured, with stirring, into a solution of 2.5 g (28 mmol) of cuprous cyanide and 3.0 g (47 mmol) of potassium cyanide in 150 mL of dry dimethyl sulfoxide. The resulting mixture was heated to 40° C. to form a solution and this solution was poured into 750 mL of water. The mixture obtained was extracted with ether (2×300 mL) and the ethereal extract was washed with water, dried over magnesium sulfate, filtered, and concentrated by evaporation under reduced pressure. The residue was purified by column chromatography on silica gel to obtain 500 mg (48 percent of theory) of the title compound as a light yellow solid melting at 157°–158° C.

Elemental Analysis $C_{17}H_{17}N_3S$ Calc.: %C, 69.1; %H, 5.80; %N, 14.2 Found: %C, 69.1; %H, 5.89; %N, 14.3.

$^1$H NMR (CDCl$_3$): 8.9(s, 1H); 7.7(br, 1H); 7.55(d, 1H, j=7.4); 7.4(d, 1H, j=7.7); 7.3(s, 1H); 4.4(s, 1H); 2.95(d, 1H); 2.95(d, 1H, j=16); 2.90(d, 1H, j=16); 2.65(s, 3H); 1.35(s, 3H); 0.9(s, 3H).

31. Preparation of 5-(2,2-Dimethyl-6-methylthioindan-1-yl)-4-methylthiopyrimidine (Cpd. 204)

To a mixture of 1.0 g (3.5 mmol) of 5-(6-amino-2,2-dimethylindan-1-yl)-4-methylthiopyrimidine in 25 mL of dry acetonitrile at 5° C. was added with stirring 1.0 g (7.0 mmol) of nitrosonium tetrafluoroborate. After 30 min the resulting solution was poured with stirring into a solution of 20 g (0.20 mol) of dimethyl disulfide in 100 mL of acetonitrile. After 2 hr, 0.50 g of sodium methanethiolate was added and the reaction mixture was heated with stirring to 60° C. for 16 hr. The mixture was cooled and poured into 600 mL of ether with stirring. The ethereal phase was recovered and was washed with water (2×100 mL), dried over magnesium sulfate, filtered, and concentrated by evaporation under reduced pressure. The residue was purified by column chromatography on silica gel to obtain 500 mg (45 percent of theory) of the title compound as a light gold oil.

Elemental Analysis $C_{17}H_{20}N_3S_2$ Calc.: %C, 64.5; %H, 6.37; %N, 8.85; %S, 20.3 Found: %C, 64.3; %H, 6.20; %N, 9.04; %S, 20.5.

$^1$H NMR (CDCl$_3$): 8.8(s, 1H); 7.7(br, 1H); 7.1–7.2(m, 2H); 6.8(s, 1H); 4.3(s, 1H); 2.85(d, 1H, j=15.9); 2.78(d, 1H, j=15.9); 2.6(s, 3H); 2.6(s, 3H); 2.4(s, 3H); 1.3(s, 3H); 0.9(s, 3H).

32. Preparation of 5-(2,2-Dimethyl-6-phenylsulfonylaminoindan-1-yl)-4-methylthiopyrimidine (Cpd. 208)

To a solution of 1.0 g (3.5 mmol) of 5-(6-amino-2,2-dimethylindan-1-yl)-4-methylthiopyrimidine in 20 mL of dry pyridine was added with stirring 0.45 g (3.7 mmol) of benzenesulfonyl chloride. The mixture was allowed to react for 16 hr and was then poured into dilute aqueous hydrochloric acid with stirring. The resulting mixture was extracted with ether and the ethereal extract was dried over magnesium sulfate, filtered, and concentrated by evaporation under reduced pressure. The remaining oil was diluted with a small amount of dichloromethane and then hexane was added. The precipitate that formed was collected by filtration and dried under reduced pressure to obtain 700 mg (88 percent of theory) of the title compound as a tan solid melting at 174°–176° C.

Elemental Analysis $C_{22}H_{25}N_3O_2S_2$ Calc.: %C, 62.1; %H, 5.45; %N, 9.87 Found: %C, 61.8; %H, 5.54; %N, 9.77.

$^1$H NMR (d6-DMSO): 10.0(s, 1H); 8.8(s, 1H); 7.6(m, 3H); 7.5(m, 2H); 7.4(s, 1H); 7.15(d, 1H, j=8); 6.95(d, 1H, j=9.0); 6.6(s, 1H); 4.1(s, 1H); 2.7(s, 2H); 2.6(s, 3H); 1.2 (s, 3H); 0.7(s, 3H).

33. Preparation of 5-(2,2-Dimethyltetralin-1-yl)-4-(monofluoromethylthio)pyrimidine (Cpd. 129)

To a solution of 2.0 g (7.0 mmol) of 5-(2,2-dimethyltetralin-1-yl)-4-methylthiopyrimidine in 100 mL of dry acetonitrile was added with stirring 3.0 g (9.1 mmol) of 1-chloromethyl-4-fluoro-1,4-diazoniabicyclo[2.2.2]octane bis(tetrafluoroborate). The mixture was allowed to react for 16 hours and then most of the acetonitrile was removed by evaporation under reduced pressure. The residue was partitioned between ether and water and the organic phase was recovered, dried over magnesium sulfate, filtered, and concentrated by evaporation under reduced pressure. The residual oil was purified by column chromatography on silica gel to obtain 700 mg of the title compound as a tan solid melting at 126°–128° C.

Elemental Analysis $C_{17}H_{19}FN_2S$ Calc.: %C, 67.5; %H, 6.33; %N, 9.26; %S, 10.6 Found: %C, 66.8; %H, 6.47; %N, 9.22; %S, 10.4.

$^1$H NMR (CDCl$_3$): 8.9(s, 1H); 7.9(s,1H); 7.1 (m, 2H); 7.0(t, 1H, j=7.7); 6.7(d, 1H, j=7.7); 6.3(d, d, 1H, j=9.4, 46.0); 6.15(d, d, 1H, j=9.4, 45.6); 4.1(s,1H); 2.9(m, 2H); 1.75(m, 1H); 1.57(m, 1H); 1.07(s, 3H); 0.85(s, 3H).

5 - ( 2 , 2 - D i m e t h y l i n d a n - 1 - y l ) - 4 - monofluoromethylthiopyrimidine (Cpd. 177), a tan solid melting at 67.5°–69° C., was prepared analogously.

34. Preparation of 5-(2.2-Dimethyl-1-methoxyindan-1-yl)-4-(methylthio)pyrimidine (Cpd. 56)

Sodium hydride (0.16 g of 60 percent in mineral oil, 4.0 mmol) was added with stirring to a solution of 1.0 g (3.5 mmol) of 5-(2.2-dimethyl-1-hydroxyindan-1-yl)-4-(methylthio)pyrimidine in 10 mL of tetrahydrofuran. After the hydrogen evolution and exotherm were complete, 0.43 g (3 mmol) of methyl iodide was added and the mixture was allowed to react overnight at ambient temperature. The mixture was then poured into 20 mL of cold water and the resulting mixture was extracted with ethyl acetate. The organic extract was washed with water and then with concentrated aqueous sodium hydroxide, was dried over magnesium sulfate, and was concentrated by evaporation under reduced pressure. The oily solid residue was extracted with hexane to remove cold hexane insolubles and then hot hexane insolubles were removed by filtration of a hot hexane solution. The hexane was removed from the filtrate by evaporation under reduced pressure to obtain 0.87 g of the title compound as a white solid melting at 130°–132° C.

Elemental Analysis $C_{17}H_{20}N_2OS$ Calc.: %C, 68.0; %H, 6.71; %N, 9.32 Found: %C, 68.0; %H, 6.57; %N, 9.21.

35. Preparation of 5-(2,2-Dimethyl-7-fluoroindan-3-on-1-yl)-4-methylthiopyrimidine (Cpd. 142)

A. (2-Fluorophenyl)(4-methylthio-5-pyrimidinyl)methanol

To a slurry of 20 g (98 mmol) of 5-bromo-4-methylthiopyrimidine in 200 mL of anhydrous tetrahydrofuran at −90° C. was slowly added with stirring and cooling 40 mL (100 mmol) of 2.5M n-butyl lithium in hexane. After a 20-min reaction period, 13.3 g of 2-fluorobenzaldehyde was added with stirring. The solution was allowed to gradually warm to −25° C. It was then poured into dilute aqueous hydrochloric acid with stirring. The resulting mixture was extracted with ether and the ethereal extract was dried over magnesium sulfate, filtered, and partially concentrated by evaporation under reduced pressure. The remaining mixture was diluted with hexane and the solids that formed were collected by filtration to obtain 9.75 g of the title compound as colorless solid melting at 176°–177° C.

Elemental Analysis $C_{12}H_{11}FN_2OS$ Calc.: %C, 57.6; %H, 4.43; %N, 11.1 Found: %C, 57.3; %H, 4.35; %N, 11.0.

$^1$H NMR (d6-DMSO): 8.9(s, 1H); 8.6(s, 1H); 7.3(m, 2H); 6.3(d, 1H, j=4.8); 5.9(d, 1H, j=4.8); 3.3(s, 1H); 2.5(s, 3H).

B. 5-(Chloro(2-fluorophenyl)methyl)-4-methylthiopyrimidine

To a slurry of 9.5 g (38 mmol) of (2-fluorophenyl)(4-methylthio-5-pyrimidinyl)methanol in 50 mL of dichloromethane was added slowly with stirring 10 g (84 mmol) of thionyl chloride. The resulting solution was stirred 1 hr. and then was concentrated by evaporation under reduced pressure. The resulting amber oil was diluted with 5 mL of dichloromethane and then 100 mL of hexane. The light tan solid that formed was collected by filtration and dried under reduced pressure to obtain 10.1 g (99 percent of theory) of the title compound in crude form melting at 144°–145° C.

Elemental Analysis $C_{12}H_{10}ClFN_2S$ Calc.: %C, 53.6; %H, 3.75; %N, 11.9 Found: %C, 49.2; %H, 3.68; %N, 9.51.

$^1$H NMR (CDCl$_3$): 9.1(s, 1H); 8.6(s, 1H); 7.4(m, 2H); 7.2(t, 1H, j=7.3); 7.1(t, 1H, j=8.4); 6.4(s, 1H); 2.8(s, 3H).

C. Methyl 2,2-Dimethyl-3-(2-fluorophenyl)-3-(4-methylthio-5-pyrimidinyl)propanoate To a solution of lithium diisopropylamide prepared from 5.3 g (57 mmol) of diisopropylamine and 21 mL (57 mmol) of 2.5M n-butyl lithium in hexane and 100 mL of dry tetrahydrofuran at −10° C. was slowly added with stirring 5.3 g (57 mmol) of methyl 2-methylpropanoate. The resulting solution was allowed to warm slowly to 12° C. and was then recooled to −10° C. To this was added in small portions with stirring 7.0 g (26 mmol) of 5-(chloro-(2-fluorophenyl)methyl)-4-methylthiopyrimidine. After 1 hr the resulting solution was warmed to ambient temperature. Ether and dilute aqueous hydrochloric acid were added and the ethereal phase was recovered, dried over magnesium sulfate, filtered, and concentrated by evaporation under reduced pressure. The residue was purified by column chromatography on silica gel to obtain 5.3 g (60 of theory) of the title compound as a colorless oil.

Elemental Analysis $C_{17}H_{19}FN_2O_2S$ Calc.: %C, 61.1; %H, 5.73; %N, 8.37; %S, 9.59 Found: %C, 61.0; %H, 5.62; %N, 8.49; %S, 9.52.

$^1$H NMR (CDCl$_3$): 8.8(s, 1H); 8.6(br. 1H) 7.2(m, 1H); 7.1(m, 3H); 4.8(s, 1H); 3.5(s, 3H); 2.5(s, 3H); 1.33(s, 3H); 1.31(s, 3H).

D. 2,2-Dimethyl-3-(2-fluorophenyl)-3-(4-methylthio-5-pyrimidinyl)propanoic acid

A solution of 1.0 g (3.0 mmol) of methyl 2,2-dimethyl-3-(2-fluorophenyl)-3-(4-methylthio-5-pyrimidinyl)propanoate and 1.7 g (24 mmol) of sodium methanethiolate in 20 mL of dry N,N-dimethylformamide was heated to 50° C. with stirring for 30 minutes. The resulting solution was poured into dilute aqueous hydrochloric acid and the mixture obtained was extracted with ether. The ethereal extract was washed with water, dried over magnesium sulfate, filtered, and concentrated by evaporation under reduced pressure to obtain a light yellow solid. This solid was triturated in 30 mL of dichloromethane, collected by filtration, and dried under reduced pressure to obtain 570 mg (60 of theory) of the title compound as a light yellow solid melting at 204°–205° C.

Elemental Analysis $C_{16}H_{17}FN_2O_2S$ Calc.: %C, 60.0; %H, 5.35; %N, 8.74; %S, 10.0 Found: %C, 59.8; %H, 5.33; %N, 8.69; %S, 9.89.

$^1$H NMR (d6-DMSO): 8.8(s, 1H); 8.7(s, 1H); 7.1–7.3(m, 5H); 4.8(s, 1H); 2.4(s, 3H); 1.25(s, 3H); 1.23(s, 3H).

E. 5-(2,2-Dimethyl-7-fluoroindan-3-on-1-yl)-4-methylthiopyrimidine

A solution of 4.8 g (15 mmol) of 2,2-dimethyl-3-(2-fluorophenyl)-3-(4-methylthio-5-pyrimidinyl)propanoic acid in 75 mL of Eaton's reagent was heated to 75° C. for 20 hr with stirring. The solution obtained was cooled and poured into ice. The resulting mixture was extracted with ether and the ethereal extract was dried over magnesium sulfate, filtered, and concentrated by evaporation under reduced pressure to obtain 4.5 g of a gold oil. A portion of this oil was purified by column chromatography on silica gel to obtain the title compound as a colorless solid melting at 111.5°–113° C.

Elemental Analysis $Cl_6H_{15}FN_2OS$ Calc.: %C, 63.5; %H, 5.00; %N, 9.26; %S, 10.6 Found: %C, 63.9; %H, 5.06; %N, 9.24; %S, 11.0.

$^1$H NMR (CDCl$_3$): 8.8(br, 1H); 7.7(d ,1H, j=7.4); 7.5(m, 2H); 7.4(t, 1H, j=8.1); 4.7(s, 1H); 2.6(s, 3H); 1.5(s, 3H); 0.9(s, 3H).

5-(2,2-Dimethylindan-3-on-1-yl)-4-methylthiopyrimidine (Cpd. 214), a colorless solid melting at 76°–77° C., was prepared similarly.

Elemental Analysis $C_{16}H_{16}N_2OS$ Calc.: %C, 67.6; %H, 5.67; %N, 9.85; %S, 10.1 Found: %C, 67.5; %H, 5.72; %N, 9.67; %S, 10.1.

36. Preparation of 5-(2,2-Dimethyl-7-fluoroindan-1-yl)-4-methylthiopyrimidine (Cpd. 203)

A solution of 500 mg of 5-(2,2-dimethyl-7-fluoroindan-3-on-1-yl)-4-methylthiopyrimidine, 5.0 g of triethylsilane and 3.0 g of boron trifluoride etherate in 20 mL of 1,2-dichloroethane was heated to reflux with stirring for 16 hr. The resulting solution was cooled and then poured into an aqueous solution of sodium carbonate. The mixture obtained was extracted with ether and the ethereal extract was dried over magnesium sulfate, filtered, and concentrated by evaporation under reduced pressure. The residue was purified by column chromatography on silica gel to obtain a colorless oil. A portion of this oil was crystallized from hexane to obtain 150 mg of the title compound as a white solid melting at 81°–82° C.

Elemental Analysis $C_{16}H_{17}FN_2S$ Calc.: %C, 66.6; %H, 5.98; %N, 9.71 Found: %C, 66.5; %H, 5.88; %N, 9.76.

$^1$H NMR (CDCl$_3$): 8.8(s, 1H); 7.7(s, 1H); 7.2(m, 1H); 7.0(d, 1H, j=7.4); 6.8(t, 1H, j=8.9); 4.3(s, 1H); 2.9(d, 1H, j=16); 2.7(d, 1H, j=16); 2.6(s, 3H); 1.3(s, 3H); 0.9(s, 3H).

37. Preparation of 5-(2,2-Dimethylindan-1-yl)-4-(N-methylmethanesulfonylamino)pyrimidine (Cpd. 226)

N-Methylmethanesulfonamide (1.9 g) and then 1.2 g (17 mmol) of 5-(2,2-dimethylindan-1-yl)-4-methanesulfonylpyrimidine were added to a slurry of 0.40 g (17 mmol) of sodium hydride in 50 mL of dry N,N-dimethylformamide with stirring and the resulting mixture was heated at 80° C. for 1 hour. The mixture was then cooled and partitioned between ether and water. The organic phase was recovered, dried over magnesium sulfate, filtered, and concentrated by evaporation under reduced pressure. The residue was purified by column chromatography on silica gel and 0.57 g of the title compound was obtained as a tan solid melting at 107°–109° C.

Elemental Analysis $C_{17}H_{21}N_3O_2S$ Calc.: %C, 61.6; %H, 6.39; %N, 12.7; %S, 9.67 Found: %C, 61.9; %H, 6.50; %N, 12.5; %S, 9.88.

38. Preparation of 5-(2,2-Dimethylindan-1-yl)-4-(N-methylaminosulfonyl)pyrimidine (Cpd. 231)

A 3.0 g (8.7 mmol) sample of 4-benzylthio-5-(2,2-dimethylindan-1-yl)pyrimidine was dissolved in 100 mL of dichloromethane and 50 mL of water and 4.2 g of concentrated aqueous hydrochloric acid were added. The resulting mixture was cooled to 5° C. and 60 mL of commercial bleach (5.25 percent sodium hypochlorite solution) was added dropwise with stirring and cooling over a 12-min period. The mixture was then stirred for 30 min at 5°–6° C. A solution of 1.5 g of sodium bisulfite in 15 mL of water was added with stirring and then 10 mL of 2M (20 mmol) methylamine in tetrahydrofuran was added with stirring and cooling. The pH of the mixture was adjusted to 9–10 by the addition of 2N aqueous sodium hydroxide. After 1 hour gas-liquid chromatographic analysis of the product indicated it was about 29 percent benzyl chloride, 21 percent 4-chloro-5-(2,2-dimethylindan-1-yl)pyrimidine, and 26 percent desired product. An additional 100 mL of dichloromethane and 100 mL of water were added. The organic phase was recovered, washed with 100 mL of water, dried over sodium sulfate, and concentrated by evaporation under reduced pressure. The residual oil was dissolved in a minimum amount of dichloromethane and chromatographed on dry flask grade silica gel, eluting initially with a 50:50 by volume mixture of dichloromethane and hexane and then with dichloromethane in 150 mL fractions. Fractions 15–25 were combined and concentrated by evaporation under reduced pressure. The solid residue was extracted with hexane and then rechromatographed on silica gel eluting with a 20:80 by volume mixture of ethyl acetate and hexane. The resulting white solid was impure title compound melting at 152°–160° C.

Elemental Analysis $C_{16}H_{19}N_3O_2S$ Calc.: %C, 60.5; %H, 6.03; %N, 13.2 Found: %C, 59.1; %H, 5.87; %N, 12.8.

$^1$H NMR (CDCl$_3$): 9.14(s, 1H); 8.39(s, 1H); 7.42–7.14(m, 4H); 5.45(m, 1H); 5.17(s, 1H); 3.09(d,3H); 3.0(q, 2H); 1.43(s, 3H); 1.0(s, 3H).

39. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 8 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture. A highest application rate of 4.48 Kg/Ha is achieved when 50 mg of test compound is employed.

The treated pots and control pots were placed in a greenhouse with an approximately 15 hr photoperiod which was maintained at about 23°–29° C. during the day and 22°–28° C. during the night. Nutrients and water were added on a regular basis and supplemental lighting was provided with overhead metal halide 1000 Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are presented in Table 3.

TABLE 3

PREEMERGENCE HERBICIDAL ACTIVITY

| Cpd. No. | Rate, Kg/Ha | Lambs-quarters | Morning-glory | Pig-weed | Black-grass | Barn-yard Grass | Crab-grass | Giant fox-tail | Rox Orange Sorghum |
|---|---|---|---|---|---|---|---|---|---|
| 1 | 0.56 | 100 | 50 | 100 | 10 | 100 | 100 | 99 | 99 |
| 3 | 0.56 | — | 10 | 80 | 80 | 100 | 100 | 98 | 100 |
| 5 | 0.56 | 100 | 75 | 100 | 20 | 78 | 100 | 98 | 20 |
| 6 | 0.56 | 90 | — | 80 | 80 | 100 | 100 | 100 | 100 |
| 7 | 1.18 | — | 90 | 85 | 50 | 100 | 100 | 98 | 100 |
| 8 | 1.12 | 100 | 78 | 80 | 90 | 100 | 100 | 100 | 100 |
| 9 | 1.12 | 100 | 80 | 100 | 70 | 100 | 100 | 100 | 95 |
| 10 | 1.12 | — | 30 | 95 | 90 | 100 | 100 | 100 | 95 |
| 13 | 1.12 | 90 | 75 | 85 | 50 | 100 | 100 | 95 | 98 |
| 14 | 2.24 | 78 | 50 | 85 | 50 | 100 | 100 | 98 | 0 |
| 16 | 1.18 | — | 60 | 80 | 60 | 100 | 100 | 98 | 95 |
| 18 | 0.56 | 100 | 90 | 75 | 90 | 100 | 95 | 100 | 100 |
| 19 | 1.12 | 80 | 60 | 70 | 90 | 100 | 95 | 70 | 70 |
| 21 | 1.12 | 80 | 50 | 78 | 20 | 100 | 100 | 55 | 50 |
| 22 | 1.12 | 90 | 90 | 90 | 75 | 30 | 100 | 95 | 100 |
| 23 | 4.48 | 0 | 50 | 50 | 20 | 0 | 100 | 70 | 20 |
| 24 | 1.12 | 40 | 20 | 75 | 20 | 100 | 100 | 75 | 30 |
| 26 | 1.12 | 90 | 65 | 90 | 70 | 100 | 100 | 100 | 98 |
| 27 | 2.24 | — | 60 | 65 | 0 | 78 | 100 | 98 | 0 |
| 28 | 1.12 | 80 | 75 | 95 | 80 | 100 | 100 | 95 | 100 |
| 29 | 1.12 | 45 | 45 | 80 | 80 | 100 | 95 | 90 | 80 |
| 30 | 1.12 | 80 | 65 | 85 | 30 | 95 | 100 | 100 | 60 |
| 31 | 4.48 | 70 | 50 | 90 | 45 | 90 | 95 | 95 | 80 |
| 32 | 0.56 | 80 | 60 | 80 | 60 | 100 | 100 | 55 | 100 |
| 34 | 1.12 | 60 | 20 | 78 | 35 | 100 | 100 | 100 | 70 |
| 35 | 2.24 | 60 | 60 | 50 | 60 | 70 | 100 | 80 | 65 |
| 36 | 2.24 | 100 | 65 | 60 | 75 | 70 | 78 | 100 | 75 |
| 38 | 1.12 | 70 | 75 | 75 | 55 | 100 | 100 | 100 | 95 |
| 39 | 2.24 | 60 | 45 | 85 | 20 | 100 | 100 | 95 | 50 |
| 40 | 1.12 | 80 | 75 | 85 | 50 | 78 | 100 | 95 | 95 |
| 42 | 1.12 | — | 90 | 90 | 40 | 98 | 100 | 98 | 100 |
| 43 | 1.12 | 80 | 55 | 85 | 78 | 95 | 95 | 90 | 70 |
| 44 | 0.59 | 95 | 78 | 80 | 78 | 100 | 98 | 95 | 100 |
| 45 | 0.59 | 80 | 70 | 80 | 78 | 100 | 100 | 98 | 95 |
| 46 | 0.28 | 95 | 55 | 78 | 60 | 100 | 100 | 80 | 85 |
| 47 | 0.56 | 78 | 30 | 80 | 78 | 100 | 90 | 90 | 55 |
| 48 | 1.12 | 90 | 0 | 95 | 45 | 100 | 100 | 100 | 100 |
| 50 | 0.56 | 80 | 78 | 85 | 78 | 100 | 100 | 90 | 65 |
| 51 | 0.28 | 78 | 50 | 85 | 80 | 95 | 100 | 100 | 90 |
| 52 | 1.12 | 80 | 50 | 80 | 78 | 100 | 100 | 100 | 100 |
| 53 | 2.24 | 55 | 50 | 80 | 35 | 80 | 95 | 70 | 78 |
| 54 | 1.12 | 95 | 78 | 95 | 70 | 100 | 100 | 100 | 100 |
| 55 | 1.12 | 78 | 45 | 95 | 90 | 100 | 100 | 100 | 100 |
| 58 | 2.24 | 85 | 60 | 85 | 80 | 100 | 100 | 100 | 100 |
| 59 | 2.24 | 90 | 0 | 80 | 90 | 78 | 95 | 90 | 80 |
| 60 | 1.87 | — | 75 | 95 | 70 | 95 | 100 | 100 | 100 |
| 62 | 1.12 | 90 | 45 | 90 | 65 | 100 | 90 | 90 | 90 |
| 63 | 1.12 | 75 | 75 | 80 | 40 | 100 | 100 | 100 | 50 |
| 66 | 1.12 | 90 | 65 | 95 | 80 | 60 | 100 | 100 | 65 |
| 67 | 2.24 | 90 | 90 | 90 | 90 | 95 | 100 | 100 | 90 |
| 69 | 0.56 | 85 | 80 | 70 | 95 | 75 | 90 | 85 | 70 |
| 76 | 1.12 | 95 | 65 | 60 | 60 | 100 | 99 | 99 | 20 |
| 78 | 0.56 | 100 | 95 | 95 | 95 | 80 | 100 | 95 | 85 |
| 79 | 1.12 | 80 | 90 | 80 | 90 | 95 | 100 | 100 | 95 |
| 83 | 1.12 | 70 | 90 | 85 | — | 100 | 100 | 100 | 70 |
| 86 | 0.56 | 100 | 35 | 99 | 90 | 98 | 100 | 100 | 40 |
| 87 | 2.24 | 95 | 85 | 80 | 90 | 50 | 70 | 80 | 75 |
| 90 | 2.24 | — | 20 | 80 | 50 | 90 | 98 | 83 | 90 |
| 92 | 0.56 | 90 | 0 | 60 | 30 | 100 | 95 | 98 | 95 |
| 93 | 2.24 | — | 0 | 85 | 100 | 50 | 80 | 90 | 30 |
| 94 | 0.56 | 100 | 0 | 90 | 80 | 80 | 98 | 95 | 95 |
| 99 | 0.56 | 90 | 50 | 80 | 35 | 98 | 98 | 98 | 95 |
| 100 | 0.14 | 100 | 50 | 78 | 20 | 80 | 98 | 95 | 50 |
| 102 | 0.28 | 85 | 80 | 95 | 70 | 100 | 98 | 98 | 90 |
| 103 | 1.12 | 98 | 80 | 70 | 90 | 100 | 98 | 100 | 95 |
| 104 | 1.12 | 98 | 90 | 50 | 95 | 80 | 100 | 100 | 40 |
| 107 | 2.24 | 90 | 80 | 70 | 50 | 100 | 98 | 98 | 95 |
| 108 | 2.24 | — | 50 | 70 | 45 | 50 | 98 | 78 | 20 |
| 109 | 2.24 | 75 | 0 | 70 | 50 | 95 | 100 | 98 | 95 |
| 111 | 2.24 | — | 0 | 90 | 90 | 78 | 100 | 98 | 55 |
| 113 | 0.56 | 40 | 0 | 75 | — | 100 | 98 | 100 | 20 |
| 118 | 2.24 | 100 | 55 | 55 | 75 | 100 | 95 | 50 | 50 |
| 119 | 2.24 | 75 | 75 | 55 | 80 | 95 | 100 | 95 | 60 |

TABLE 3-continued

PREEMERGENCE HERBICIDAL ACTIVITY

| Cpd. No. | Rate, Kg/Ha | Lambs-quarters | Morning-glory | Pig-weed | Black-grass | Barn-yard Grass | Crab-grass | Giant fox-tail | Rox Orange Sorghum |
|---|---|---|---|---|---|---|---|---|---|
| 121 | 1.12 | 70 | 60 | 75 | 90 | 100 | 78 | 100 | 60 |
| 122 | 1.12 | — | 78 | 70 | 70 | 100 | 100 | 98 | 95 |
| 123 | 0.56 | 75 | 35 | 40 | 20 | 100 | 100 | 75 | 20 |
| 125 | 0.57 | 78 | 70 | 75 | 78 | 100 | 95 | 100 | 55 |
| 127 | 2.24 | 70 | 40 | 75 | 20 | 35 | 100 | 80 | 10 |
| 130 | 1.12 | 80 | 90 | 90 | 55 | 100 | 100 | 70 | 100 |
| 131 | 1.12 | 78 | 55 | 85 | 45 | 100 | 75 | 100 | 55 |
| 133 | 4.48 | 70 | 50 | 78 | 45 | 55 | 65 | 75 | 20 |
| 134 | 1.12 | 95 | 20 | 60 | 90 | 0 | 100 | 90 | 95 |
| 136 | 2.24 | 100 | 50 | 70 | 70 | 50 | 100 | 100 | 40 |
| 138 | 1.12 | 78 | 75 | 100 | 78 | 100 | 100 | 100 | 100 |
| 139 | 0.56 | 75 | 78 | 95 | 78 | 100 | 100 | 100 | 100 |
| 141 | 2.24 | 50 | 50 | 60 | 65 | 50 | 100 | 50 | 0 |
| 142 | 1.12 | 80 | 70 | 65 | 90 | 100 | 100 | 95 | 95 |
| 143 | 1.12 | 65 | 0 | 90 | 70 | 90 | 100 | 95 | 50 |
| 145 | 2.24 | 55 | 20 | 90 | 40 | 100 | 100 | 95 | 30 |
| 146 | 2.24 | 50 | 0 | 95 | 50 | 78 | 100 | 100 | 50 |
| 147 | 2.24 | 30 | 50 | 78 | 0 | 20 | 100 | 100 | 20 |
| 148 | 1.12 | 45 | 70 | 80 | 55 | 100 | 100 | 100 | 78 |
| 149 | 2.24 | 75 | 30 | 95 | 75 | 100 | 100 | 95 | 78 |
| 151 | 2.24 | 30 | 0 | 75 | 78 | 70 | 0 | 100 | 50 |
| 152 | 4.48 | 70 | 0 | 85 | 90 | 78 | 95 | 95 | 40 |
| 154 | 2.24 | 30 | 40 | 95 | 40 | 50 | 100 | 100 | 20 |
| 156 | 0.56 | 90 | 20 | 95 | 78 | 100 | 100 | 100 | 40 |
| 159 | 1.12 | 80 | 90 | 90 | 65 | 100 | 95 | 100 | 100 |
| 161 | 2.24 | 90 | 80 | 90 | 60 | 100 | 100 | 100 | 60 |
| 164 | 2.24 | 95 | 95 | 95 | 95 | 100 | 100 | 100 | 100 |
| 165 | 1.12 | 90 | 70 | 78 | 70 | 100 | 100 | 100 | 100 |
| 166 | 1.12 | 65 | 50 | 95 | 60 | 100 | 100 | 100 | 100 |
| 167 | 0.36 | 60 | 50 | 80 | 40 | 100 | 100 | 100 | 70 |
| 168 | 2.24 | 5. | 20 | 65 | 50 | 20 | 100 | 90 | 60 |
| 170 | 1.12 | 75 | 60 | 90 | 80 | 90 | 100 | 100 | 50 |
| 174 | 1.12 | 95 | 0 | 95 | 60 | 100 | 100 | 100 | 100 |
| 175 | 0.56 | 85 | 0 | 95 | 70 | 100 | 100 | 95 | 100 |
| 177 | 0.28 | 80 | 45 | 85 | 78 | 100 | 100 | 100 | 70 |
| 178 | 1.12 | 78 | 50 | 90 | 90 | 100 | 90 | 100 | 100 |
| 181 | 2.24 | 80 | 78 | 85 | 65 | 80 | 95 | 80 | 78 |
| 182 | 0.56 | 78 | 20 | 80 | 40 | 100 | 100 | 98 | 100 |
| 184 | 0.28 | 90 | 95 | 90 | 80 | 100 | 100 | 100 | 80 |
| 186 | 0.28 | 78 | 55 | 85 | 85 | 100 | 100 | 100 | 75 |
| 187 | 0.28 | 70 | 20 | 90 | 55 | 100 | 95 | 75 | 55 |
| 188 | 2.24 | 75 | 90 | 95 | 20 | 100 | 100 | 100 | 100 |
| 189 | 0.56 | 95 | 20 | 20 | 30 | 100 | 100 | 100 | 20 |
| 191 | 0.56 | 80 | 65 | 85 | 70 | 100 | 100 | 70 | 60 |
| 192 | 0.56 | 30 | 40 | 90 | 90 | 78 | 100 | 100 | 90 |
| 193 | 1.12 | 50 | 50 | 50 | 90 | 100 | 100 | 95 | 60 |
| 194 | 0.28 | 75 | 90 | 95 | 90 | 50 | 100 | 100 | 100 |
| 199 | 1.12 | 70 | 20 | 95 | 50 | 100 | 100 | 90 | 60 |
| 201 | 2.24 | 40 | 83 | 70 | 70 | 100 | 100 | 100 | 40 |
| 203 | 0.28 | 100 | 20 | 85 | 80 | 50 | 100 | 75 | 100 |
| 204 | 1.12 | 75 | 30 | 85 | 70 | 100 | 100 | 95 | 100 |
| 209 | 0.56 | 20 | 80 | 30 | 85 | 100 | 100 | 100 | 0 |
| 210 | 2.24 | 70 | 30 | 100 | 70 | 90 | 100 | 100 | 100 |
| 212 | 1.12 | 60 | 55 | 60 | 70 | 100 | 100 | 50 | 60 |
| 231 | 0.28 | 80 | 50 | 40 | 95 | 100 | 95 | 100 | 100 |
| 232 | 0.56 | 80 | 50 | 85 | 78 | 100 | 100 | 100 | 95 |
| 233 | 0.56 | 65 | 30 | 70 | 80 | 60 | 30 | 30 | 30 | lambsquarters = *Chenopodium album*
morningglory = *Ipomoea hederacea*
pigweed = *Amaranthus retroflexus*
blackgrass = *Alopecurus myosuroides*
barnyardgrass = *Echinochloa crus-galli*
crabgrass = *Digitaria sanguinalis*
giant foxtail = *Setaria faberi*
Rox orange sorghum = *Sorghum bicolor*

40. Evaluation of Herbicidal Activity in Rice

The test plant species were planted in a mud matrix prepared by mixing with water a soil composed of about 35–50 percent sand, 25–35 percent silt, and 25–30 percent clay and having a pH of about 7.4–7.7, the amount of sand being the minimum necessary to give the mud the desired consistency for optimum growth of each species of plant (thickest for barnyard grass and thinnest for rice. The consistency of the mud was measured by its ability to spread on a flat surface. Separate containers were used for rice (ORYSA, *Orysa sativa*), pickerelweed (MOOVA, *monochoria vaginalis*), and the combination of barnyard grass (ECHCG, *Echinochloa crus-galli*) and Taiwan bulrush (SCPJU, *Scirpus juncoides*). An amount of 17:6:10 NPK slow release fertilizer appropriate for each plant species was placed in the bottom of a 16 oz (ounce)(470 mL) (for the weeds) or 32 oz (940 mL) (for the rice) plastic container having a diameter of 10.5 cm (surface area of 86.6 cm$^2$) and slurried mud was added leaving space at the top for 3 cm of flood water.

In one 16 oz container sufficient MOOVA seeds to achieve a plant stand of 30–50 plants were planted on the surface of the mud. The seeds were covered with 5–8 g of river sand, water was added to achieve a 3 cm flood, and the containers were covered, when required, to retard evaporation and to retain heat. The containers were placed in a controlled environment greenhouse and held for approximately 8 days under flooded conditions at which time the plants were in the cotyledon plus one leaf stage. In a second 16 oz container enough ECHCG seed to achieve a stand of 10–20 plants was pressed into the mud in half of the container. Sufficient presoaked (3–4 weeks at about 4° C.) SCPJU seeds to achieve a 20–30 plant stand were mixed with a small amount of sifted soil and placed in the other half of the container. After about 3 hours the containers were covered with plastic wrap and placed in a greenhouse with a 16 hour daylight cycle at 24° C. The containers were held for about 3 days at which time the plastic wrap was removed. The ECHCG plants were in the one leaf stage and the SCPJU plants were in the cotyledon plus one leaf stage. A small amount of washed gravel was then added and water was added to achieve a 1 cm flood. The flood was increased to 3 cm on the day of treatment. ORYSA seedlings in the 2–3 leaf stage that had been grown in a 200 cell plastic plug tray using a soil-less medium consisting of peat moss, vermiculite, and fir bark were transplanted into the 32 oz containers. Before transplanting, the bottom ¼ of each plug was removed and the growing medium was washed off. Two sets of three plants (clusters or hills) were planted in each container at a depth of about 2 cm (distance between the seed hull and the surface of the mud). Water was added to achieve a flood of 3 cm and the plants were placed in a greenhouse for about 5 days during which time the plants added 0.5 to 1 new leaves.

Forty mL of test solution (sufficient to treat 15 containers (3 replications of 5 serial dilution rates) were prepared by dissolving in 20 mL of acetone an appropriate weighed amount of chemical (9.0 mg for a test rate of 1000 g/Ha (1000 g/Ha×8.7×10$^{-7}$ Ha)) and then adding 20 mL of water containing 0.1 percent Tween™ surfactant. Four mL of this stock solution were then injected into the flood water by means of an Eppendorf positive displacement pipettor to achieve the highest application rates and appropriate smaller amounts were injected for lower application rates.

The treated plants were placed in a greenhouse with a 16 hour daylight cycle and a daytime demand temperature of 29° C. and a nighttime demand temperature of 28° C. No water was added for 48 hours after application and then a flood of 3 cm was maintained by the addition of water twice daily. The condition of each of the plants was observed 3 weeks after application of the test compounds and scores for each container were recorded using a scale of 0 to 100 in which 0 is no injury and 100 is complete kill. Some of the results obtained are presented in Table 4.

TABLE 4

| | | PADDY RICE HERBICIDAL ACTIVITY | | | |
|---|---|---|---|---|---|
| Cpd. No. | Rate, g/Ha | ORYSA | ECHCG | MOOVA | SCPJU |
| 1 | 31 | <5 | 100 | 100 | 85 |
| 2 | 31 | 5 | 55 | 100 | 30 |
| 3 | 63 | <5 | 100 | 99 | 85 |
| 5 | 250 | 0 | 95 | 95 | 85 |
| 6 | 125 | 0 | 100 | 100 | 92 |
| 7 | 31 | 0 | 100 | 90 | 100 |
| 8 | 31 | 30 | 65 | 75 | 30 |
| 9 | 63 | 0 | 100 | 90 | 100 |
| 10 | 63 | 0 | 100 | 20 | 90 |
| 11 | 125 | 0 | 100 | 30 | 90 |
| 13 | 31 | 0 | 100 | 100 | 75 |
| 14 | 10 | 60 | 98 | 25 | 16 |
| 15 | 250 | 0 | 100 | 100 | 78 |
| 16 | 63 | 5 | 100 | 99 | 75 |
| 17 | 125 | 30 | 100 | 90 | 90 |
| 18 | 31 | 0 | 100 | 100 | 30 |
| 19 | 63 | 10 | 75 | 90 | 90 |
| 20 | 31 | 0 | 100 | 90 | 50 |
| 21 | 63 | 0 | 100 | >95 | 0 |
| 22 | 31 | 0 | 100 | 20 | 0 |
| 23 | 125 | 10 | <5 | 70 | 30 |
| 26 | 63 | 0 | 100 | 98 | 90 |
| 27 | 125 | 40 | 35 | 100 | 30 |
| 28 | 16 | 0 | 100 | 98 | 65 |
| 29 | 63 | 0 | 60 | 100 | 75 |
| 30 | 500 | 0 | 100 | 30 | 100 |
| 31 | 250 | 20 | 5 | 100 | 60 |
| 32 | 63 | 0 | >95 | 75 | 100 |
| 33 | 63 | 0 | 100 | 99 | 70 |
| 35 | 125 | 30 | 10 | 100 | 70 |
| 36 | 250 | 0 | 0 | 100 | 75 |
| 37 | 250 | 30 | 60 | 50 | 70 |
| 38 | 63 | 0 | 95 | 85 | 90 |
| 39 | 63 | 15 | 10 | 80 | 90 |
| 39 | 63 | 15 | 10 | 80 | 90 |
| 40 | 125 | 5 | 75 | 85 | 100 |
| 41 | 250 | 10 | 20 | 100 | 90 |
| 42 | 16 | <5 | 80 | 90 | 90 |
| 43 | 63 | 5 | 40 | 100 | 30 |
| 44 | 63 | 0 | 100 | 98 | 90 |
| 45 | 63 | 0 | 100 | 85 | 100 |
| 46 | 31 | 0 | 100 | 100 | 25 |
| 47 | 250 | 15 | 100 | 100 | 80 |
| 48 | 125 | 10 | 95 | 100 | 50 |
| 49 | 500 | 20 | 30 | 95 | 60 |
| 50 | 63 | 0 | 100 | 90 | 100 |
| 50 | 63 | 0 | 100 | 90 | 100 |
| 51 | 63 | 20 | 95 | 60 | 100 |
| 52 | 0 | 100 | 100 | 70 | 141 |
| 53 | 125 | 25 | 60 | 30 | 30 |
| 54 | 63 | 0 | 100 | >95 | 75 |
| 58 | 250 | 5 | 100 | 75 | 60 |
| 60 | 500 | 0 | 100 | 80 | 90 |
| 60 | 500 | 0 | 100 | 80 | 90 |
| 62 | 1000 | 0 | 100 | 100 | 70 |
| 63 | 1000 | 0 | 10 | 50 | 20 |
| 64 | 1000 | 5 | 10 | 100 | 35 |
| 65 | 1000 | 10 | 20 | 80 | 10 |
| 66 | 63 | 35 | 20 | 99 | 60 |
| 68 | 16 | <5 | 95 | 100 | 60 |
| 69 | 63 | 35 | 10 | 98 | 40 |
| 70 | 125 | 10 | >95 | 90 | 90 |
| 71 | 63 | 5 | <5 | 99 | 35 |
| 72 | 63 | 0 | 95 | 98 | 35 |
| 73 | 63 | 10 | 20 | 90 | 90 |
| 74 | 125 | 0 | 100 | 100 | 45 |
| 75 | 63 | <5 | 30 | 98 | 20 |
| 76 | 125 | 10 | 70 | 90 | 85 |
| 77 | 31 | 15 | 0 | 98 | 65 |
| 78 | 63 | 10 | 0 | 100 | 0 |
| 79 | 125 | 15 | 0 | 85 | 65 |
| 80 | 125 | 0 | 90 | 55 | 0 |
| 81 | 31 | 35 | 0 | 75 | 25 |
| 82 | 31 | 5 | 70 | 100 | 20 |

TABLE 4-continued

PADDY RICE HERBICIDAL ACTIVITY

| Cpd. No. | Rate, g/Ha | ORYSA | ECHCG | MOOVA | SCPJU |
|---|---|---|---|---|---|
| 84 | 31 | 0 | 60 | 100 | 90 |
| 85 | 125 | 15 | 0 | 100 | 75 |
| 86 | 125 | 5 | 60 | 90 | 50 |
| 88 | 63 | 5 | 100 | 95 | 75 |
| 90 | 250 | 10 | 50 | 10 | 25 |
| 92 | 250 | 10 | 100 | 10 | 25 |
| 94 | 125 | 5 | 50 | 100 | 90 |
| 95 | 125 | 15 | 0 | 90 | 70 |
| 96 | 63 | 0 | 98 | 100 | 65 |
| 97 | 250 | 15 | 55 | 90 | 60 |
| 98 | 31 | 5 | 50 | 100 | 90 |
| 100 | 16 | 0 | 75 | 95 | 90 |
| 101 | 63 | 55 | 0 | 99 | 90 |
| 102 | 31 | 10 | 100 | 90 | 90 |
| 103 | 63 | 0 | 100 | 90 | 40 |
| 104 | 63 | 35 | 35 | 100 | 35 |
| 105 | 125 | 0 | 100 | 95 | 75 |
| 106 | 250 | 60 | 70 | 60 | 70 |
| 107 | 125 | 0 | 100 | 95 | 50 |
| 108 | 125 | 0 | 20 | 70 | 0 |
| 109 | 250 | 0 | 95 | 90 | 90 |
| 110 | 500 | 15 | 50 | 90 | 0 |
| 111 | 250 | 10 | 60 | 0 | 0 |
| 113 | 250 | 0 | 100 | 90 | 45 |
| 117 | 250 | 5 | 35 | 65 | 0 |
| 118 | 63 | 5 | 40 | 30 | 50 |
| 120 | 63 | 5 | 100 | 95 | 70 |
| 121 | 250 | 20 | 60 | 95 | 75 |
| 122 | 7.8 | 10 | 80 | 50 | 60 |
| 123 | 250 | 45 | 30 | 70 | 90 |
| 124 | 16 | 35 | 70 | 98 | 90 |
| 125 | 125 | 5 | 75 | 85 | 100 |
| 126 | 31 | 0 | 100 | 100 | 75 |
| 127 | 125 | 15 | 98 | 99 | 60 |
| 129 | 31 | 0 | 100 | 100 | 80 |
| 130 | 63 | 5 | 100 | 100 | 90 |
| 131 | 63 | 40 | 50 | 90 | 100 |
| 132 | 31 | 0 | 100 | 100 | 70 |
| 134 | 125 | 0 | 30 | 30 | 20 |
| 136 | 125 | 5 | 60 | 65 | 20 |
| 137 | 125 | 0 | 100 | 90 | 100 |
| 138 | 125 | 5 | 100 | 98 | 90 |
| 139 | 16 | 0 | 100 | 100 | 70 |
| 140 | 31 | 0 | 99 | 98 | 60 |
| 141 | 250 | 45 | 70 | 100 | 40 |
| 142 | 125 | 30 | 100 | 100 | 60 |
| 143 | 1000 | 10 | 100 | 90 | 20 |
| 144 | 500 | 0 | 100 | 50 | 20 |
| 145 | 1000 | 5 | 100 | 95 | 60 |
| 146 | 1000 | 5 | 90 | 60 | 0 |
| 147 | 1000 | 15 | 70 | 50 | 20 |
| 148 | 500 | 5 | 100 | 60 | 20 |
| 149 | 250 | 0 | 100 | 10 | 0 |
| 150 | 2000 | 0 | 10 | 70 | 0 |
| 151 | 2000 | 0 | 70 | 50 | 0 |
| 152 | 1000 | 5 | 50 | 100 | 20 |
| 154 | 1000 | 20 | 80 | 25 | 10 |
| 156 | 125 | 5 | 75 | 100 | 90 |
| 157 | 31 | 10 | 85 | 60 | 60 |
| 158 | 63 | 0 | 100 | 100 | 65 |
| 159 | 250 | 0 | 100 | 50 | 50 |
| 161 | 125 | 5 | 73 | 100 | 75 |
| 163 | 1000 | 5 | 0 | 0 | 90 |
| 164 | 250 | 0 | 100 | 100 | 85 |
| 165 | 250 | 0 | 80 | 100 | 90 |
| 166 | 125 | 15 | 100 | 100 | 70 |
| 169 | 500 | 5 | 100 | 30 | 90 |
| 172 | 125 | 0 | 0 | 100 | 20 |
| 173 | 125 | 0 | 0 | 100 | 30 |
| 174 | 500 | 0 | 75 | 50 | 60 |
| 175 | 250 | 0 | 100 | 100 | 90 |
| 176 | 250 | 0 | 100 | 100 | 90 |
| 177 | 63 | 0 | 100 | >95 | 85 |
| 178 | 125 | 10 | 70 | 60 | 60 |
| 179 | 1000 | 5 | 80 | 50 | 40 |
| 180 | 2000 | 0 | 25 | 100 | 10 |
| 181 | 250 | 30 | 75 | 100 | 40 |
| 182 | 63 | 0 | 100 | 80 | 35 |
| 183 | 500 | 0 | 75 | 10 | 20 |
| 184 | 16 | 5 | 65 | 70 | 60 |
| 185 | 250 | 10 | 100 | 100 | 90 |
| 186 | 16 | 10 | 60 | 100 | 10 |
| 187 | 63 | 10 | 100 | 100 | 90 |
| 188 | 125 | 10 | 80 | 30 | 30 |
| 189 | 125 | 0 | 100 | 100 | 90 |
| 190 | 7.8 | 20 | 10 | 90 | 0 |
| 191 | 31 | 0 | 100 | 100 | 75 |
| 192 | 500 | 0 | 100 | 100 | 50 |
| 193 | 125 | 0 | 100 | 100 | 10 |
| 194 | 7.8 | 5 | 25 | 80 | 30 |
| 195 | 125 | 10 | 20 | 50 | 20 |
| 196 | 31 | 10 | 70 | 100 | 70 |
| 197 | 31 | 5 | 100 | 100 | 70 |
| 198 | 250 | 0 | 0 | 90 | 0 |
| 199 | 250 | 5 | 100 | 100 | 90 |
| 201 | 125 | 0 | 0 | 90 | 50 |
| 203 | 125 | 5 | 100 | 100 | 85 |
| 204 | 500 | 0 | 100 | 100 | 80 |
| 209 | 125 | 5 | 85 | 100 | 70 |
| 210 | 250 | 5 | 25 | 100 | 80 |
| 212 | 1000 | 5 | 85 | 0 | 50 |
| 213 | 125 | 25 | 100 | 80 | 80 |
| 214 | 125 | 0 | 85 | 80 | 60 |
| 219 | 125 | 10 | 100 | 100 | 75 |
| 228 | 1000 | 20 | 80 | 100 | 70 |
| 229 | 1000 | 0 | 25 | 80 | 65 |
| 231 | 31 | 30 | 90 | 85 | 90 |
| 232 | 63 | 15 | 85 | 50 | 80 |

ORYSA = *Orysa sativa*; ECHCG = *Echinochloa crus-galli*; MOOVA = *Monochoria vaginalis*; SCPJU = *Scirpus juncoides*

What is claimed is:

1. A 5-polycyclylpyrimidine compound of the formula:

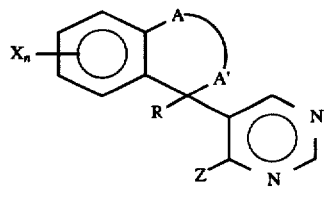

wherein the moiety

represents a 2 or 3 unit chain having a maximum of 3 chain atoms, the units of which are selected from —CR'$_2$— (which may contain up to 3 units) and —CR'=CR'—, —O—, —S—, —NH—, —N($C_1$–$C_4$ alkyl)-, —C(O)—, or —S(O)$_2$— (which may contain up to 1 unit) or represents a chain of the formula:

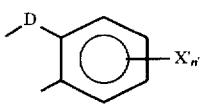

wherein D represents —O—CR'$_2$—O— or —CR'$_2$—CR'$_2$—;

each R' independently represents H, C$_1$–C$_3$ alkyl or phenyl or two R' located on the same carbon atom or on adjacent carbons together represent —(CH$_2$) (2-5)-;

R represents H, OH, F, Cl, Br, C$_1$–C$_3$ alkyl, or C$_1$–C$_3$ alkoxy;

Z represents L(C$_1$–C$_4$ alkyl) optionally substituted with one or two substituents selected from Cl, Br, CN, OH, O(C$_1$–C$_3$ alkyl), SO$_m$(C$_1$–C$_3$ alkyl), N(C$_1$–C$_3$ alkyl)$_2$, CO$_2$(C$_1$–C$_4$ alkyl), CO$_2$H, or with up to the maximum possible number of F, or with a phenyl or pyridinyl moiety each optionally substituted with up to 3 compatible substituents selected from F, Cl, Br, NO$_2$, CF$_3$, CH$_3$, OCH$_3$, SO$_m$CH$_3$, CN, and CO$_2$(C$_1$–C$_4$ alkyl); L(C$_3$–C$_4$ alkenyl) optionally substituted with one or two substituents selected from Cl, Br, CN, O(C$_1$–C$_3$ alkyl), SO$_m$(C$_1$–C$_3$ alkyl), CO$_2$(C$_1$–C$_4$ alkyl), CO$_2$H, and phenyl or with up to the maximum possible number of F; L(C$_3$–C$_4$ alkynyl) optionally mono-substituted with CO$_2$(C$_1$–C$_4$ alkyl) or C$_6$H$_5$; L(phenyl) optionally substituted with up to 3 compatible substituents selected from F, Cl, Br, NO$_2$, CF$_3$, CH$_3$, OCH$_3$, SO$_m$CH$_3$, CN, and CO$_2$(C$_1$–C$_4$ alkyl); CN, CO$_2$(C$_1$–C$_4$ alkyl), CONH$_2$, CONH(C$_1$–C$_4$ alkyl), CON(C$_1$–C$_4$ alkyl)$_2$, CO$_2$H, NH$_2$, NHSO$_2$(C$_1$–C$_4$ alkyl), N(C$_1$–C$_4$ alkyl)-SO$_2$(C$_1$–C$_4$ alkyl), SH, F, Cl, or Br;

L represents -, O, SO$_m$, SO$_2$NH, SO$_2$N(C$_1$–C$_4$ alkyl), NH, or N(C$_1$–C$_4$ alkyl);

X and X' each independently represents F, Cl, Br, CN, CO$_2$(C$_1$–C$_4$ alkyl), NO$_2$, NH(C$_1$–C$_3$ alkyl), N(C$_1$–C$_3$ alkyl)$_2$, NH$_2$, NHCO(C$_1$–C$_3$ alkyl), NHSO$_2$(C$_1$–C$_3$ alkyl), or N(SO$_2$(C$_1$–C$_3$ alkyl))$_2$; or represents C$_1$–C$_3$ alkyl, O(C$_1$–C$_3$ alkyl), SO$_m$(C$_1$–C$_3$ alkyl), or CO(C$_1$–C$_3$ alkyl) each alkyl of which is optionally singly to completely fluorinated; or two adjacent X or X' together represent —OCH$_2$O— optionally substituted with one or two fluorine atoms;

n and n' each independently represents 0, 1, 2, or 3; and each m independently represents 0, 1, or 2; or an N-oxide derivative thereof.

2. A compound of claim 1 wherein the moiety

represents —CH$_2$C(CH$_3$)$_2$—.

3. A compound of claim 1 wherein the moiety

represents —CH$_2$CH$_2$C(CH$_3$)$_2$—.

4. A compound of claim 1 wherein the moiety

represents —OCH$_2$C(CH$_3$)$_2$—.

5. A compound of claim 1 wherein Z represents methoxy, methylthio, ethylthio, monofluoromethylthio, or allylthio.

6. A compound of claim 5 wherein Z represents methylthio.

7. A compound of claim 5 wherein Z represents monofluoromethylthio.

8. A compound of claim 1 wherein R represents H.

9. A compound of claim 1 wherein the benzene ring(s) independently are either unsubstituted or are substituted with one or two substituents selected from fluoro, chloro, and methyl.

10. The compound of claim 1 which is 5-(2,2-dimethylindan-1-yl)-4-methylthiopyrimidine.

11. The compound of claim 1 which is 5-(2,2-dimethylindan-1-yl)-4-monofluoromethylthiopyrimidine.

12. The compound of claim 1 which is 5-(2,2-dimethyltetralin-1-yl)-4-methylthiopyrimidine.

13. The compound of claim 1 which is 5-(2,2,7-trimethyltetralin-1-yl)-4-methylthiopyrimidine.

14. An herbicidal composition comprising an agriculturally acceptable adjuvant or carrier in admixture with an herbicidally effective amount of a 5-polycyclylpyrimidine compound of the formula:

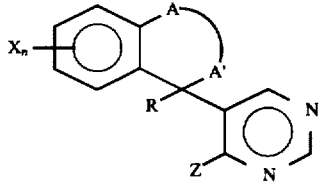

wherein
the moiety

represents a 2 or 3 unit chain having a maximum of 3 chain atoms, the units of which are selected from —CR'$_2$— (which may contain up to 3 units) and —CR'=CR'—, —O—, —S—, —NH—, —N(C$_1$–C$_4$ alkyl)-, —C(O)—, or —S(O)$_2$— (which may contain up to 1 unit) or represents a chain of the formula:

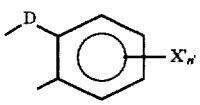

wherein D represents —O—CR'$_2$—O— or —CR'$_2$—CR'$_2$—;

each R' independently represents H, C$_1$–C$_3$ alkyl or phenyl or two R' located on the same carbon atom or on adjacent carbons together represent —(CH$_2$) (2-5)-;

R represents H, OH, F, Cl, Br, C$_1$–C$_3$ alkyl, or C$_1$–C$_3$ alkoxy;

Z represents L($C_1$–$C_4$ alkyl) optionally substituted with one or two substituents selected from Cl, Br, CN, OH, O($C_1$–$C_3$ alkyl), $SO_m$($C_1$–$C_3$ alkyl), N($C_1$–$C_3$ alkyl)$_2$, $CO_2$($C_1$–$C_4$ alkyl), $CO_2H$, or with up to the maximum possible number of F, or with a phenyl or pyridinyl moiety each optionally substituted with up to 3 compatible substituents selected from F, Cl, Br, $NO_2$, $CF_3$, $CH_3$, $OCH_3$, $SO_mCH_3$, CN, and $CO_2$($C_1$–$C_4$ alkyl); L($C_3$–$C_4$ alkenyl) optionally substituted with one or two substituents selected from Cl, Br, CN, O($C_1$–$C_3$ alkyl), $SO_m$($C_1$–$C_3$ alkyl), $CO_2$($C_1$–$C_4$ alkyl), $CO_2H$, and phenyl or with up to the maximum possible number of F; L($C_3$–$C_4$ alkynyl) optionally mono-substituted with $CO_2$($C_1$–$C_4$ alkyl) or $C_6H_5$; L(phenyl) optionally substituted with up to 3 compatible substituents selected from F, Cl, Br, $NO_2$, $CF_3$, $CH_3$, $OCH_3$, $SO_mCH_3$, CN, and $CO_2$($C_1$–$C_4$ alkyl); CN, $CO_2$($C_1$–$C_4$ alkyl), $CONH_2$, CONH($C_1$–$C_4$ alkyl), CON($C_1$–$C_4$ alkyl)$_2$, $CO_2H$, $NH_2$, $NHSO_2$($C_1$–$C_4$ alkyl), N($C_1$–$C_4$ alkyl)-$SO_2$($C_1$–$C_4$ alkyl), SH, F, Cl, or Br;

L represents -, O, $SO_m$, $SO_2NH$, $SO_2N$($C_1$–$C_4$ alkyl), NH, or N($C_1$–$C_4$ alkyl);

X and X' each independently represents F, Cl, Br, CN, $CO_2$($C_1$–$C_4$ alkyl), $NO_2$, NH($C_1$–$C_3$ alkyl), N($C_1$–$C_3$ alkyl)$_2$, $NH_2$, NHCO($C_1$–$C_3$ alkyl), $NHSO_2$($C_1$–$C_3$ alkyl), or N($SO_2$($C_1$–$C_3$ alkyl))$_2$; or represents $C_1$–$C_3$ alkyl, O($C_1$–$C_3$ alkyl), $SO_m$($C_1$–$C_3$ alkyl), or CO($C_1$–$C_3$ alkyl) each alkyl of which is optionally singly to completely fluorinated; or two adjacent X or X' together represent —$OCH_2O$— optionally substituted with one or two fluorine atoms;

n and n' each independently represents 0, 1, 2, or 3; and each m independently represents 0, 1, or 2; or an N-oxide derivative thereof.

15. A composition of claim 14 wherein the moiety represents —$CH_2C(CH_3)_2$—.

16. A composition of claim 14 wherein the moiety represents —$CH_2CH_2C(CH_3)_2$—.

17. A composition of claim 14 wherein the moiety represents —$OCH_2C(CH_3)_2$—.

18. A composition of claim 14 wherein Z represents methoxy, methylthio, ethylthio, monofluoromethylthio, or allylthio.

19. A composition of claim 18 wherein Z represents methylthio.

20. A composition of claim 18 wherein Z represents monofluoromethylthio.

21. A composition of claim 14 wherein R represents H.

22. A composition of claim 14 wherein the benzene ring(s) independently are either unsubstituted or are substituted with one or two substituents selected from fluoro, chloro, and methyl.

23. A composition of claim 14 wherein the compound is 5-(2,2-dimethylindan-1-yl)-4-methylthiopyrimidine.

24. A composition of claim 14 wherein the compound is 5-(2,2-dimethylindan-1-yl)-4-monofluoromethylthiopyrimidine.

25. A composition of claim 14 wherein the compound is 5-(2,2-dimethyltetralin-1-yl)-4-methylthiopyrimidine.

26. A composition of claim 14 wherein the compound is 5-(2,2,7-trimethyltetralin-1-yl)-4-methylthiopyrimidine.

27. A composition of claim 14 further comprising an herbicidally effective amount of an auxin herbicide selected from (2,4-dichlorophenoxy)acetic acid, 2-(2,4-dichlorophenoxy)propionic acid, (4-chloro-2-methylphenoxy)acetic acid, 2-(4-chloro-2-methylphenoxy)propionic acid, ((3,4,6-trichloro-2-pyridinyl)oxy)acetic acid, ((4-amino-3,5-dichloro-6-fluoro-2-pyridinyl)oxy)acetic acid, 4-amino-3,5,6-trichloro-2-pyridinecarboxylic acid, 3,6-dichloro-2-pyridinecarboxylic acid, and 2-methoxy-3,6-dichlorobenzoic acid in the form of the acid or an agriculturally acceptable salt or ester.

28. A composition according to claim 27 wherein the auxin herbicide is (2,4-dichlorophenoxy)acetic acid.

29. A composition according to claim 27 wherein the auxin herbicide is ((3,4,6-trichloro-2-pyridinyl)oxy)acetic acid.

30. A method of controlling undesirable vegetation which comprises applying to the vegetation or to the locus thereof an herbicidally effective amount of a 5-polycyclylpyrimidine compound of the formula:

wherein the moiety represents a 2 or 3 unit chain having a maximum of 3 chain atoms, the units of which are selected from —CR'$_2$— (which may contain up to 3 units) and —CR'=CR'—, —O—, —S—, —NH—, —N($C_1$–$C_4$ alkyl)-, —C(O)—, or —S(O)$_2$— (which may contain up to 1 unit) or represents a chain of the formula:

wherein D represents —O—CR'$_2$—O— or —CR'$_2$—CR'$_2$—;

each R' independently represents H, $C_1$–$C_3$ alkyl or phenyl or two R' located on the same carbon atom or on adjacent carbons together represent —($CH_2$) (2-5)-;

R represents H, OH, F, Cl, Br, $C_1$–$C_3$ alkyl, or $C_1$—$C_3$ alkoxy;

Z represents L(C$_1$–C$_4$ alkyl) optionally substituted with one or two substituents selected from Cl, Br, CN, OH, O(C$_1$–C$_3$ alkyl), SO$_m$(C$_1$–C$_3$ alkyl), N(C$_1$–C$_3$ alkyl)$_2$, CO$_2$(C$_1$–C$_4$ alkyl), CO$_2$H, or with up to the maximum possible number of F, or with a phenyl or pyridinyl moiety each optionally substituted with up to 3 compatible substituents selected from F, Cl, Br, NO$_2$, CF$_3$, CH$_3$, OCH$_3$, SO$_m$CH$_3$, CN, and CO$_2$(C$_1$–C$_4$ alkyl); L(C$_3$–C$_4$ alkenyl) optionally substituted with one or two substituents selected from Cl, Br, CN, O(C$_1$–C$_3$ alkyl), SO$_m$(C$_1$–C$_3$ alkyl), CO$_2$(C$_1$–C$_4$ alkyl), CO$_2$H, and phenyl or with up to the maximum possible number of F; L(C$_3$–C$_4$ alkynyl) optionally mono-substituted with CO$_2$(C$_1$–C$_4$ alkyl) or C$_6$H$_5$; L(phenyl) optionally substituted with up to 3 compatible substituents selected from F, Cl, Br, NO$_2$, CF$_3$, CH$_3$, OCH$_3$, SO$_m$CH$_3$, CN, and CO$_2$(C$_1$–C$_4$ alkyl); CN, CO$_2$(C$_1$–C$_4$ alkyl), CONH$_2$, CONH(C$_1$–C$_4$ alkyl), CON(C$_1$–C$_4$ alkyl)$_2$, CO$_2$H, NH$_2$, NHSO$_2$(C$_1$–C$_4$ alkyl), N(C$_1$–C$_4$ alkyl)-SO$_2$(C$_1$–C$_4$ alkyl), SH, F, Cl, or Br;

L represents -, O, SO$_m$, SO$_2$NH, SO$_2$N(C$_1$–C$_4$ alkyl), NH, or N(C$_1$–C$_4$ alkyl);

X and X' each independently represents F, Cl, Br, CN, CO$_2$(C$_1$–C$_4$ alkyl), NO$_2$, NH(C$_1$–C$_3$ alkyl), N(C$_1$–C$_3$ alkyl)$_2$, NH$_2$, NHCO(C$_1$–C$_3$ alkyl), NHSO$_2$(C$_1$–C$_3$ alkyl), or N(SO$_2$(C$_1$–C$_3$ alkyl))$_2$; or represents C$_1$–C$_3$ alkyl, O(C$_1$–C$_3$ alkyl), SO$_m$(C$_1$–C$_3$ alkyl), or CO(C$_1$–C$_3$ alkyl) each alkyl of which is optionally singly to completely fluorinated; or two adjacent X or X' together represent —OCH$_2$O— optionally substituted with one or two fluorine atoms;

n and n' each independently represents 0, 1, 2, or 3; and each m independently represents 0, 1, or 2; or an N-oxide derivative thereof.

31. A method of claim 30 wherein the moiety

represents —CH$_2$C(CH$_3$)$_2$—.

32. A method of claim 30 wherein the moiety

represents —CH$_2$CH$_2$C(CH$_3$)$_2$—.

33. A method of claim 30 wherein the moiety

represents —OCH$_2$C(CH$_3$)$_2$—.

34. A method of claim 30 wherein Z represents methoxy, methylthio, ethylthio, monofluoromethylthio, or allylthio.

35. A method of claim 34 wherein Z represents methylthio.

36. A method of claim 34 wherein Z represents monomethylthio.

37. A method of claim 30 wherein R represents H.

38. A method of claim 30 wherein the benzene ring(s) independently are either unsubstituted or are substituted with one or two substituents selected from fluoro, chloro, and methyl.

39. A method of claim 30 wherein the compound is 5-(2,2-dimethylindan-1-yl)-4-methylthiopyrimidine.

40. A method of claim 30 wherein the compound is 5-(2,2-dimethylindan-1-yl)-4-monofluoromethylthiopyrimidine.

41. A method of claim 30 wherein the compound is 5-(2,2-dimethyltetralin-1-yl)-4-methylthiopyrimidine.

42. A method of claim 30 wherein the compound is 5-(2,2,7-trimethyltetralin-1-yl)-4-methylthiopyrimidine.

43. A method of claim 30 wherein the undesirable vegetation is selectively controlled in the presence of a rice crop.

44. A method of claim 30 wherein the compound is applied preemergently.

45. A method of claim 30 wherein the compound is applied in combination with an auxin herbicide selected from (2,4-dichlorophenoxy)acetic acid, 2-(2,4-dichlorophenoxy)propionic acid, (4-chloro-2-methylphenoxy)acetic acid, 2-(4-chloro-2-methylphenoxy)propionic acid, ((3,4,6-trichloro-2-pyridinyl)oxy)acetic acid, ((4-amino-3,5-dichloro-6-fluoro-2-pyridinyl)oxy)acetic acid, 4-amino-3,5,6-trichloro-2-pyridinecarboxylic acid, 3,6-dichloro-2-pyridinecarboxylic acid, and 2-methoxy-3,6-dichlorobenzoic acid in the form of the acid or an agriculturally acceptable salt or ester.

46. A method according to claim 45 wherein the auxin herbicide is (2,4-dichlorophenoxy)acetic acid.

47. A method according to claim 45 wherein the auxin herbicide is ((3,4,6-trichloro-2-pyridinyl)oxy)acetic acid.

* * * * *